US005750105A

United States Patent [19]
Newman et al.

[11] Patent Number: 5,750,105
[45] Date of Patent: May 12, 1998

[54] RECOMBINANT ANTIBODIES FOR HUMAN THERAPY

[75] Inventors: Roland A. Newman, San Diego; Nabil Hanna, Olivenhain; Ronald W. Raab, San Diego, all of Calif.

[73] Assignee: IDEC Pharmaceuticals Corporation, San Diego, Calif.

[21] Appl. No.: 476,349

[22] Filed: Jun. 7, 1995

Related U.S. Application Data

[62] Division of Ser. No. 379,072, Dec. 5, 1995, which is a continuation of Ser. No. 912,292, Jul. 10, 1992, abandoned, which is a continuation-in-part of Ser. No. 856,281, Mar. 23, 1992, abandoned, which is a continuation-in-part of Ser. No. 735,064, Jul. 25, 1991, abandoned.

[51] Int. Cl.$^6$ .................... A61K 39/395; A61K 39/40; A61K 39/42; C12P 21/08
[52] U.S. Cl. .................... 424/133.1; 424/177.1; 424/137.1; 424/138.1; 530/387.3
[58] Field of Search ................ 424/130.1, 133.1, 424/177.1, 137.1, 138.1; 530/387.3

[56] References Cited

U.S. PATENT DOCUMENTS

| | | | |
|---|---|---|---|
| 4,816,397 | 3/1989 | Boss et al. | 435/68 |
| 4,816,567 | 3/1989 | Cabilly et al. | 530/387.3 |
| 4,973,745 | 11/1990 | Schoemaker et al. | 530/387.3 |
| 4,975,369 | 12/1990 | Beavers et al. | 435/69.6 |

FOREIGN PATENT DOCUMENTS

| | | |
|---|---|---|
| 0451216 B1 | 10/1991 | European Pat. Off. . |
| 523949A1 | 1/1993 | European Pat. Off. . |
| 0682040 A1 | 11/1995 | European Pat. Off. . |
| 9008198 | 7/1990 | WIPO . |

OTHER PUBLICATIONS

Rosenberg, M. et al., *Biotheraphy*, "Soluble Recombinant CD4—A Potential Therapeutic Agent for HIV Infector", 2:107, (1990).
Riechmann, L. et al., *Nature*, "Reshaping Human Antibodies for Therapy", 332:323–327, (1988).
Houghton, A.N. et al., *Seminars in Oncology*, "Monoclonal Antibodies Potential Applications to the Treatment of Cance", 13:165, (1986).
Watanabe, M. et al., *Proceedings of the National Academy of Sciences*, 88:4616–4620, (1991).
Letvin, et al., Effect of Recombinant Soluble CD4 in Rhesus Monkeys Infected with Simian Immunodeficient Virus of Macagues Abstracts from the V. Int. Conf. on AIDS, p. 535, (1989).
BS Heteromycloma line, abstract.
Herpes Transformation, abstract.
Morrison, *Science vol.* 229, pp. 1202 (1985).
Queen et al., *NAS8610029* (1989).
Waldmann, *Science Vol.*, 252, pp. 1657 (1991).
Sharp, RM et al., 126 *J. Imm. Methods* 287 (1990).
Ehrlich, PH et al., 28 *Mol. Immun.* 319 (1991).
Groves, DJ & Tucker, EM 23 Vet. *Immuno. and Imunopath.* 1 (1989).
Stanley, HA & Reese, RT 82 PNAS 6272 (1985).
VOPR Virusol, vol. 30, No. 5, issued Oct. 1985, Markova et al., "Monkey B lymphocyte subpopulations transformed by baboon herpes virus in vivo and in tissue cultures", 549–553.
Harris et al., T.B Tech., vol. 11, p. 42 (1993).
Truneh et al., "Humoral Response of Cynomolgus Macaques to Human Soluble CD4: Antibody Reactivity Restricted to Xeno–Human Determinants", *Cellular Immunology*, vol. 131, No. 1, pp. 98–108 (Nov. 1990).
Van Meurs et al., "Production of Primate Monoclonal Antibodies", *Journal Or Immunological Methods*, 1986, vol. 95, pp. 123–128.
Schroeder et al., "Early Restriction of the Human Antibody Repertoire", *Science*, vol. 238, pp. 791–793, (Nov. 6, 1987).
Combriato et al., "V Lambda and J Lambda–C Lambda Gene Segments of the Human Immunoglobulin Lambda Light Chain Locus are Separated by 14 KB and Rearrange by a Deletion Mechanism", *European Journal Or Immunology*, vol. 21, pp. 1513–1522 (Jun. 1991).
Hughes–Jones et al., "Nucleotide Sequences and Three–Dimensional Modelling of the VH and VL Domains of Two Human Monoclonal Antibodies Specific for the D Antigen of the Human RH–Blood Group System", *The Biochemical Journal*, vol. 268, No. 1, pp. 135–140 (May 15, 1990).
Stephens et al., "Antibodies are Produced to the Variable Regions of the External Envelope Glycoprotein of Human Immunodeficiency Virus Type 1 in Chimpanzees Infected with the Virus and Baboons Immunized with a Candidate Recombinant Vaccine", *The Journal Of General Virology*, vol. 73, No. 5, pp. 1099–1106 (May 1992).
Amoroso et al., *J. Immun.*, Herpes Transformation, abstract, 145:3155 (1990).
Huse et al., *Science*, BS Heteromycloma Line, abstract 246:1275 (1989).
Ehrlich et al., Hum. Antibod. Hybridomas, vol. 1, No. 1 (1990).
Ehrlich et al., Hybridoma, vol. 7, No. 4, pp. 385–395 (1988).
Ehrlich et al., Hybridoma, vol. 6, No. 2, pp. 151–160 (1987).
Ehrlich et al., *Clin. Chem.*, 34:1681 (1988).
Van Meel et al., *J. Immunological Methods*, 80:267 (1985).
Persson et al., Proc. Natl. Acad. Sci. USA, 88:2432 (1991).
Meek et al., J. Immun., 146:2434 (1991).
Allison et al., *J. Immunological Methods*, 95:157 (1986).
Nishimura, Y. et al., *Cancer Research*, 47:999 (1987).
Ward, E.S. et al., *Nature*, 341:544 (1989).
McClure, M.O. et al., *Nature*, 330:487 (1987).
Truneh, A. et al., *Cell Immun.*, 131:98 (1990).
Camerini, D. and Seed, B., Abstract No. T.C.P. 125, V International Conference on AIDS, pp. 587 (1989).
Camerini, D. and Seed, B., *Cell*, 60:747 (1990).
Jones, P.T., et al., *Nature*, 321:522 (1986).

*Primary Examiner*—Lila Feisee
*Assistant Examiner*—Geetha P. Bansal
*Attorney, Agent, or Firm*—Burns, Doane, Swecker & Mathis LLP

[57] ABSTRACT

Chimeric antibodies including an Old World monkey portion and a human portion, nucleic acid encoding such antibodies, Old World monkey monoclonal antibodies, and methods for their production and use.

10 Claims, 26 Drawing Sheets

FIG. 1

| | -20 | -19 | -18 | -17 | -16 | -15 | -14 | -13 | -12 | -11 | -10 | -9 | -8 | -7 | -6 | -5 | -4 | -3 | -2 | -1 | |
|---|---|---|---|---|---|---|---|---|---|---|---|---|---|---|---|---|---|---|---|---|---|
| MONKEY | | | | | | | | | | | | | | | | | | | | | |
| | ATG | GAC | TGG | ACC | TGG | AGG | CTC | CTC | TTT | ... | GTG | GTG | GCA | GCA | GCT | ACA | GGT | GCC | AAG | TCC | VH1 |
| | | | | | TGT | TCC | ACG | CTC | CTG | ... | CTG | CTG | ACC | GTC | CCG | TCC | TGG | GTT | TTG | TCC | VH2 |
| | | | | | | | | | TTG | ... | CTA | CTG | ACC | GTC | CCG | TCC | TGG | GTC | TTG | TCC | " |
| | | | | | TGT | TCC | ACA | CTC | TTG | ... | CTA | CTG | ACC | GTC | CCG | TCC | TGG | GTC | TTG | TCC | " |
| | ATG | GAG | TTT | GGG | CTG | CTG | AGC | TGG | GTT | ... | CTT | GTT | GCT | ATT | TTC | AAA | GGT | GTC | CAG | TGT | VH3 |
| | ATG | GAG | TTT | GGG | CTG | CTG | AGC | TGG | GTT | ... | CTT | GTT | GCT | CTT | TTA | AAG | GGC | GTC | CAG | TGT | " |
| | ATG | GAG | TTT | GGG | CTG | CTG | AGC | TGG | GTT | ... | CTT | GTT | GCT | ATT | TTA | AGA | GGC | GTC | CAG | TGT | " |
| | ATG | AAA | CAC | CTG | TGG | TTC | TTC | CTC | CTC | ... | CTG | GTG | GCG | GCT | CCC | AGA | TGG | GTC | CTG | TCC | VH4 |
| | ATG | AAA | CAC | CTG | TGG | TTC | TTC | TTC | CTC | ... | CTG | CTG | GCA | GCT | CCC | AGA | TGG | GTC | CTG | TCC | " |
| | | | | | | | | | | | TG | GCT | GTT | CTC | CAA | GGA | GTC | TGT | TCC | VH5 |
| HUMAN | | | | | | | | | | | | | | | | | | | | | |
| | ATG | GAC | TGG | ACC | TGG | AGG | GTC | TTC | TGC | ... | TTG | CTG | GCT | GTA | GCA | CCA | GGT | GCC | CAC | TCC | VH1 |
| | ATG | GAC | TGG | ACC | TGG | ... | ATC | CTC | TTC | ... | TTG | GTG | GCA | GCA | GCC | ACG | CGA | GTC | CAC | TCC | " |
| | ATG | GAC | TGG | ATA | CTT | TGT | TCC | ACG | CTG | ... | CTA | CTG | ACT | GTC | CCG | TCC | TGG | GTC | TTA | TCC | VH2 |
| | ATG | GAG | TTT | GGG | CTG | AGC | TGG | CTT | TTT | ... | CTT | GTG | GCT | ATT | TTA | AAA | GGT | GTC | CAG | TGT | VH3 |
| | ATG | GAG | TTT | GGG | CTG | AGC | TGG | CTG | TTC | ... | CTT | GTT | GCT | GTT | TTA | AAA | GGT | GTC | CAG | TGT | " |
| | ATG | GAG | TTT | GGG | CTG | AGC | TGG | CTG | TTC | ... | CTT | GTT | GCT | ATT | TTA | AAA | GGT | GTC | CAG | TGT | " |
| | ATG | GAG | TTT | GGG | CTG | AGC | TGG | CTG | TTC | ... | CTT | GTT | GCT | CTT | TTA | AAA | GGT | GTC | CAG | TGT | " |
| | ATG | AAA | CAC | CTG | TGG | TTC | TTC | CTC | CTC | ... | TGT | CAG | GCA | GAT | GTG | AGG | TGG | GTC | CTG | TCC | VH4 |
| | ATG | AAA | CA. | CTG | TGG | TTC | TTC | CTT | CTC | TGG | CTG | GTG | GCA | GCT | CCC | AGA | TGG | GTC | CTG | TCC | " |

Underlined = Primer sequence

5' 'Sense' Primers

A. Human or Monkey heavy chain early leader sequence primers with SalI site

V<sub>H</sub>1    5' ACTAA<u>GTCGAC</u>ATGGACTGGACCTGG 3'

V<sub>H</sub>2    5' ACTAA<u>GTCGAC</u>ATGGACATACTTTGTTCCAC 3'

V<sub>H</sub>3    5' ACTAA<u>GTCGAC</u>ATGGAGTTTGGGCTGAGC 3'

V<sub>H</sub>4    5' ACTAA<u>GTCGAC</u>ATGAAACACCTGTGGTTCTT 3'

V<sub>H</sub>5    5' ACTAA<u>GTCGAC</u>ATGGGGTCAACCGCCATCCT 3'

V<sub>H</sub>6    5' ACTAA<u>GTCGAC</u>ATGTCTGTCTCCTTCCTCAT 3'

B. Human or Monkey heavy chain late leader sequence primers with Mlu I site

V<sub>H</sub>1    5' G GCA GCA GC(CT) <u>ACG CGT</u> GCC CAC TCC GAG GT 3'   (+1 above ACG CGT)

V<sub>H</sub>2    5' G ACC GTC CCG <u>ACG CGT</u> GT(TC) TTG TCC CAG GT 3'   (+1 above ACG CGT)

V<sub>H</sub>3    5' GCT ATT TTC <u>ACG CGT</u> GTC CAG TGT GAG 3'   (+1 above ACG CGT)

V<sub>H</sub>4    5' GCG GCT CCC <u>ACG CGT</u> GTC CTG TCC CAG 3'   (+1 above ACG CGT)

V<sub>H</sub>5    5' G GCT GTT CTC <u>ACG CGT</u> GTC TGT GCC GAG GT 3'   (+1 above ACG CGT)

FIG. 7A

C. Human or Monkey framework 1 sequence primers with Xho I site $V_H$1,3a,5  CAGGTGCAGCTG<u>CTCGAG</u>TCTGG  (+1)

$V_H$2  CAGGTCAACTTA<u>CTCGAG</u>TCTGG  (+1)

$V_H$3b  GAGGTGCAGCTG<u>CTCGAG</u>TCTGG  (+1)

$V_H$4  CAGGTGCAGCTG<u>CTCGAG</u>TCGGG  (+1)

$V_H$6  CAGGTACAGCTG<u>CTCGAG</u>TCAGG  (+1)

3' 'Anti-Sense' Primers.

A. Human or Monkey Heavy Chain Constant Region Primers Anti-Sense Strand with Nhe 1 site $IgG_{1-4}$  5' GGC GGA TGC <u>GCT AGC</u> TGA GGA GAC GG 3'
  (+118)                        (+110)
             Nhe 1

FIG. 7B

5' 'Sense' Primers

A. Human or Monkey kappa light chain early leader primers with *Bgl II* site 1. 5'ATCAC<u>AGATCT</u>CTCACCATGGTGTTGCAGACCCAGGTC 3'
2. 5'ATCAC<u>AGATCT</u>CTCACCATGG(GA)G(AT)CCCC(TA)GC(TG)CAGCT 3'
3. 5'ATCAC<u>AGATCT</u>CTCACCATGGACATGAGGGTCCCCGCTCAG 3'
4. 5'ATCAC<u>AGATCT</u>CTCACCATGGACAC(GAC)AGGGCCCCCACTCAG 3'

B. Human or Monkey lambda light chain early leader primers with *Bgl II* site 1. 5'ATCAC<u>AGATCT</u>CTCACCATGGCCTGGGCTCTGCTGCTCC 3'
2. 5'ATCAC<u>AGATCT</u>CTCACCATGGCCTGGGCTCCACTACTTC 3'
3. 5'ATCAC<u>AGATCT</u>CTCACCATGACCTGCTCCCCTCTCCTCC 3'
4. 5'ATCAC<u>AGATCT</u>CTCACCATGGCCTGGACTCCTCTCTTTC 3'
5. 5'ATCAC<u>AGATCT</u>CTCACCATGACTTGGACCCCACTCCTC 3'

FIG. 7C

3' 'Anti-Sense' Primers

A. Human or Monkey kappa light chain constant region primer anti-sense strand with Kpn 1 and BsiW1 sites $C_{kappa}$

```
        +108                                      +97
5' CCG TTT GAT TTC CAG CTT GGT ACC TCC ACC GAA CGT 3'
                             Kpn 1
        +112                              +103
5' TGC AGC ATC CGT ACG TTT GAT TTC CAG CTT 3'
                BsiW1
```

B. Human or Monkey lambda light chain constant region primer anti-sense strand with Kpn 1, Hind III and Avr II sites $C_{Lambda}$

```
    +107                                  +99
5' ACC TAG GAC GGT AAG CTT GGT ACC TCC GCC 3'
                  Hind III    Kpn 1

+107                                          +97
5' ACC TAG GAC GGT CA(C/G) (C/G)TT GGT ACC TCC GCC GAA CAC 3'
                                  Kpn 1

+110                          +102
5' CTT GGG CTG ACC TAG GAC GGT CAG CCG 3'
                  Avr II
```

FIG. 7D

A. Heavy Chain Variable Region:

| VH1 | 5' | CCATGGACTGGACCTGG 3' |
|---|---|---|
| VH2 | 5' | ATGGACATACTTTGTTCCAC 3' |
| VH3 | 5' | CCATGGAGTTTGGGCTGAGC 3' |
| VH4 | 5' | ATGAAACACCTGTGGTTCTT 3' |
| VH5 | 5' | ATGGGGTCAACCGCCATCCT 3' |
| VH6 | 5' | ATGTCTGTCTCCTTCCTCAT 3' |

B. Heavy Chain Constant Region Anti-Sense Strand:

| | | +119　　　　　+115 |
|---|---|---|
| IgM | 5' | T TGG GGC GGA TGC ACT 3' |

| | | +119　　　　　+115 |
|---|---|---|
| IgG$_{1-4}$ | 5' | GA TGG GCC CTT GGT GGA 3' |

C. Light Chain Variable Region:

| | | +4　　　　　　　　　　+10 |
|---|---|---|
| Kappa | 5' | G ATG ACC CAG TCT CCA (G/T)CC TC 3' |

| | | -9　　　　　　　　　　-3 |
|---|---|---|
| Lambda | 5' | CTC A(C/T)T (T/C)(G/A)C TGC (A/C)CA GGG TCC 3' |

D. Light Chain Constant Region Anti-Sense Strands:

| | | +115　　　　　+110 |
|---|---|---|
| Kappa | 5' | AA GAC AGA TGG TGC AGC CA 3' |

| | | +118　　　　　+112 |
|---|---|---|
| Lambda | 5' | G GAA CAG AGT GAC CGA GGG G 3' |

FIG. 8

```
                    S
              A  KL    G                              Q
  Q           E  RI    T                              R   M
                                                      K   V
XVQLVQSGAEVKKPGXSVXVSCKASGYTFS DYXIH WVRQAPGXGLEWXG
------------------------------FN-G NYAIS ---------------
---Q----------T--------------T SYYIN --------V---S-

T
                         M  P
                       V R S TS
                       I LKA FT
XINPSXGXTNYAPXFQG      RVTXTDXSXNTAYMELSSLRSEDTAVYYCAR
WINTDTGNPTYAQGFKE      ---F-M---------KI-L K---------
WINPSNGNTGYAQKFQG      ---------------N-------------

V                    Homology
                         G
XYGFYSNDYXXXXXYTXDY WGQGTLVTVSS    Human  VH1  consensus
VVGTTYAEYFEF        ----A------    Monkey clone 1-2   88%
MYSWKGT             FDY  ---------- Monkey clone 1-14  94%
```

FIG. 9A

```
              G
       Q      A                                      I                        G
   Q   K     T         Q              F     F                                 A
   XVTLRESGPXLVKPTETLTLTCTVSGFSLS    TXGMXVG   WIRQPPGKXLEWLA
   -------------------------------   TSGTGYS   ----------------
   -------------------------------   ASGTGVA   ----S--------T
   -------------------------------   TSETGVG   ----------------

TM      A
                                     RLTNM   V
                                     NVSSV   G
   RINXWDDDKYYSTSLRS    RLTISKDTSKNQVVLXXXXXDPXDTATYYCAR
   RID WDNDRYYSTSLKN    ---------------------L----------
   SIF WTGVKYYNTSLKN    -----S----D----A------I-------G-
   SIY WNDVKYYITFLKS    -----R--------------------------

Homology
                    L
   RXPRXXXGDXGXYXXAFDV  WGQGTTVTVSS
   GGSI                 DY   ----V------      Human   VH2 consensus
   GVYWSGYS             FDY  ----A------      Monkey  clone 2-3    98%
   IPGTAGTVPYYTL        DS   ----AV-----      Monkey  clone 2-13   91%
                                              Monkey  clone 2-10   97%
```

FIG. 9B

```
                                                           G
          I              S         N                       S
          A              V         S                       A
    EVQLVESGGGLVQPGGSLRLSCAASGFTFS  DYAMH   WVRQAPGKGLEWVX
    ----E---------F---------------  TYDMT   --------------
    ------------------------------  EYSIH   -----Q----R---
    ------------------------------  SYDMN   --------------
    ------------------S-----------  NYNMD   ----S---------

MV    S   KT
                        NA SAF   D  EP     L  F    T
    HIEEKXNGSATYYADSVKG  RFTISRDDSKNTLYLQMNSLRAEDTAVYYCAR
    RISW NSGTIYYASSVKG   --------------------R------------
    LAGKKADRYKTEYATAVKG  -----------S------T--------------
    YISS ASGYIYYADSVKG   -------F-----S-------------------
    RVIRK GARTKYAASVKG   ---------------------------------

Homology

DPEVESLXXXFXYXXFFDS  WGQGTLVTVSS     Human VH3 consensus
    GTALCSDSGCSS    DV   -----------     Monkey clone 3-34  96%
    PVLGDRWF        FDL  -----PI----     Monkey clone 3-36  93%
    GQPVLQFLEWLLPTTGSDV  --P-V------     Monkey clone 3-40  95%
    DVAAAGT              G---V------     Monkey clone 3-9   95%
```

FIG.9C

```
                        T   Y V                 S   R
QVQLQESGPGLVKPSETLSLTCAVSGGSIS SSYYWS WIRQPPGKGLEWIG
-M---------------------------- SSYDWT -------M-----A
------------------------------ SGYYWG ----T---------
--H--------------------S------ SSGYYWG --------------
------------------------------  GYYWG ----T---------
-------A---------------S------ GDYYWF --------------

M P KK  H Y   N
YIYY  SGSTYYNPSL  KSRVTISVDTSKNQFSLKLSSVTAADTAVYYCAR
VISGN SGSADYNPSL  -N---------N------MT---------I-----
SLQGR GGNKYLNLCL  -----L-A--------------------------
SIHGS GGSNSLNPSL  -----L-----G-K-----------------F---
SLQGR GGNKYLNLSL  -----L-A--------------------------
YIYGS GGGTNYNPSL  NN--S--I-----L-----R-------------S
```

```
                                                    Homology
.................                Human VH4 consensus
GDVTSGWYRGY   FDS  WGQGCLVTVSSG  Monkey clone 4-13    90%
VGDNR         FDV  WGPGVLVTVSSG  Monkey clone 4-14    96%
ELYSSSPY      YFDF WGQGVRVTVSSG  Monkey clone 4-16    92%
GDNR          FDV  WGPGVLVTVSS   Monkey clone SC CHIM 96%
NILKYLHWLLY        WGQGVLVTVSS   Monkey anti-CD4 CHIM 88%
```

FIG. 9D

```
                               R
EVQLVQSGAEVKKPGESLKISCKGSGYSF  TSYWIG   WVRQMPGKGLEW
--------G---R-----R----TC-F--  TGFWIS   ----V--Q----

MGIIYPGDSDTRYSPSFQGH  VTISADKSISTAYLQWSSLKASDTAMYYCAR..
VGRVSPGDSITRYNPSFQGH  ---------T-TF---N-------------Q

Homology
..........     ...  ............     Human  VH5  consensus
RAGNGNYYQD     FYY  WGHGVLVTVSSG     Monkey clone 5-11    84%
```

FIG. 9E

```
                             V
DIQMTQSPSSLSASVGDRVTITC RASQSVXXSDISSYLN WYQQKP
DIQMTQSPAS-------K----- RASQ       SFSSSLA ------
DIQMTQSPAS------------- QASQ       SVSNLLA ------
DIQMTQSPAS----------V-- RASQ       GINQELS ------
DIQMTQSPAS------------- RASQ       GISSYLN ------

R
                       G     I
GKAPKLLIYXASSLES GVPSRFSGSGSGTDFTLTISSLQPEDFATYYC
--------DSASSLQS --------K--------------------S---
-----P---KASSLES ------TR-----------N--E-------F-
----T----AASSLQT ------------------S--PE---V--ED-
--------L

Homology
QQYNSLPXXYD  YT FGQGTKVEIK    Human   VK1    consensus
QQYYSYPR     LT ----------    Monkey  clone  K1-7    94%
QQGNSYP      LT --G-------    Monkey  clone  K1-3    90%
LQDYMSP      WT ----------    Monkey  clone  K1-14   90%
```

FIG. 9F

```
                                                    R
DIVMTQSPLSLPVTPGEPASISC RSSQSLVHSNGNTYLN WYLQKP
DIVMTQSPAS----L-G------ TSTQSLLSGNGYSYLN ------
-LA-P---A--A----Q------ RASESV SFFGVNLIH  ------

GQSPQLLIY KVSNRFS GVPDRFSGSGSGTDFTLKISRVEAEDVGVYYC
----H---- YDSYRAS ---T----------------------------
--P------ QASNKDT ---A--------------FNP---D-A-D---

V
               L   R                            Homology
MQALQSP YT FGQGTKNEIK         Human  VK2  consensus
MQTLQSP FT --P----D--         Monkey clone K2-8   91%
LQSKNSPR T  --G-----          Monkey SC  CHIM     81%
```

FIG. 9G

```
                          S
SYELTQPPSVSVSPGQTARITC  SGDALGQKYVY  WYQQKP
----S--R-------------GF--  GGDNVGRKSVQ  ------

M
                                            T  G
                                  N        AQ  E
GQAPVLVIY  EDSKRPS  GIPERFSGSNSGTTATLTISGVEAXDEADYYC
P--------  ADSERPS  ---A-----------------------------

QAWDSXTXXVV  FGGGTKLTVLG        Human λ III  consensus
QVWDSTADHWV  -----R-----        Monkey Anti-CD4   91%
```

FIG. 9H

```
                               S                                    G
                               V                                    S
            I                                                       A
EVQLVESGGGLVQPGGSLRLSCAASGFTFS    DYAMH    WVRQAPGKGLEWVX
Q----------V----R------------    SYGMH    --------------
Q----------V-G--R-----------S--   SYGMH    ----C---------
Q----------V---SR--------------   SYAMH    ---G----------
----L-----------------V---N---    SCTMT    --------------
--------------R-----------N-G     DYSMT    --------------
--------------R---------------    SYAMS    --------------
--R-------D--E------V--EV---I--   KAWMN    ---------Q----
-M-------AF-------K--------N--    DSTIH    -----S--S-----
------------------------------    SYDMN    --------------
-----------A------S---V-------    NYNMD    ----S---------
----E--------F----------------    TYDMT    --------------
-----------------------------S--  EYSIH    -----Q----R---
X-T-R---PX--K-TET-T-T-TV---SL-    TXGMXVG  -I--P---X---L-

MV     S  KT
                           NA     SAF    D  EP     L F  T
HIEEKXNGSATYYADSVKG    RFTISRDDSKNTLYLQMNSLRAEDTAVYYCAR
VIS   YDGSNEYFADSVKG   ----------N----MG------------------
VIS   DDGSNKYYADSVKG   --------------K----------D----------K
VIS   YDGSNKYYADSVKG   --------------S---------------------
TIS   ASGYATYYADSVKG   -I--------------------A------N
SIRSKDYGGTTEYAASVKG    -----------SI------------------S-
AISG  SGGSTYYADSVKG    --------------------------------K
QIKNKVDGGTIDYAAPVKG    --I-------S---------KI---------VG
HIENKTKNYATIYRASVKG    ------------AF---D---PD---L----P
YIS   SASGYIYYADSVKG   -------FA--S-S---S------------
RVI   RKGARTKYAASVKG   -----------------S--KT----------
RIS   WNSGTIYYASSVKG   -------------------R-----------
LAGKKADRYKTEYATAVKG    ----------S--------T-----------
RIN   XWDDDKYYSTSLRS   -L---K-T---QVV-XXXXXDPX---T-----

DPEVESLXXXFXYXX FFDS WGQGTLVTVSS       Hum VH3
DRVAVYASVFFID       SFDI -----G--      RF TS2       92%
GVYCSSSSCYSYYYYHYMDV --K--T--          RF SJ1       87%
GRFCSGQSCYSYYYYYYMDV -K--T-----        RF SJ2       91%
NISETL              DS  ----------     BE           93%
NNTSPY              FDY --E--------     CHERRI       92%
GQVLYYGSGSYHW       FDP ----------     18/2         98%
NYTGTV              DY  ----------     K6H6         84%
PPEVESLRS               --R--------    1B11         83%
GQPVLQFLEWLLPTTGS   DV  --P-V------    monkey #40   92%
DVAAAGT                 G---V------    monkey #9    90%
GTALCSDSGCSS        DV  -----------    monkey #34   95%
PVLGDRWFF           DL  -----PI-I--    monkey #36   91%
RXPRXXXGDXGXYXXA    FDV -----T-----    Hum VH2      60%
```

FIG. 10

```
              M   K   H   L   W   F   F   L   L   L   V   A   A   P   R
         GAC ATG AAA CAC CTG TGG TTC TTC CTC CTC CTG GTG GCA GCC CCC AGA

+1                              10
          W   V   L   S   Q   V   Q   L   Q   E   A   G   P   G   L   V
         TGG GTC TTG TCC CAG GTG CAG CTG CAG GAG GCG GGC CCA GGA CTG GTG

20
          K   P   S   E   T   L   S   L   T   C   S   V   S   G   G   S
         AAG CCT TCG GAG ACC CTG TCC CTC ACC TGC AGT GTC TCT GGT GGC TCC 30                                          40
          I   S   G   D   Y   Y   W   F   W   I   R   Q   S   P   G   K
         ATC AGC GGT GAC TAT TAT TGG TTC TGG ATC CGC CAG TCC CCA GGG AAG 50                                          60
          G   L   E   W   I   G   Y   I   Y   G   S   G   G   T   N
         GGA CTG GAG TGG ATC GGC TAC ATC TAT GGC AGT GGT GGG GGC ACC AAT

70
          Y   N   P   S   L   N   N   R   V   S   I   S   I   D   T   S
         TAC AAT CCC TCC CTC AAC AAT CGA GTC TCC ATT TCA ATA GAC ACG TCC 80                                          90
          K   N   L   F   S   L   K   L   R   S   V   T   A   A   D   T
         AAG AAC CTC TTC TCC CTG AAA CTG AGG TCT GTG ACC GCC GCG GAC ACG

100
          A   V   Y   Y   C   A   S   N   I   L   K   Y   L   H   W   L
         GCC GTC TAT TAC TGT GCG AGT AAT ATA TTG AAA TAT CTT CAC TGG TTA 110                                         120
          L   Y   W   G   Q   G   V   L   V   T   S   S
         TTA TAC TGG GGC CAG GGA GTC CTG GTC ACC GTC TCC
```

FIG. 13

```
        M   A   W   A   L   L   L   L   G   L   L   A   H   F   T
ACC ATG GCC TGG GCT CTG CTG CTC CTC GGC CTC CTT GCT CAC TTT ACA

+1                                      10
    D   S   A   A   S   Y   E   L   S   Q   P   R   S   V   S   V
GAC TCT GCG GCC TCC TAT GAG TTG AGT CAG CCT CGC TCA GTG TCC GTG

20
    S   P   G   Q   T   A   G   F   T   C   G   G   D   N   V   G
TCC CCA GGA CAG ACG GCC GGG TTC ACC TGT GGG GGA GAC AAC GTT GGA 30                                      40
    R   K   S   V   Q   W   Y   Q   Q   K   P   P   Q   A   P   V
AGG AAA AGT GTA CAG TGG TAC CAG CAG AAG CCA CCG CAG GCC CCT GTG 50                                      60
    L   V   I   Y   A   D   S   E   R   P   S   G   I   P   A   R
CTG GTC ATC TAT GCT GAC AGC GAA CGG CCC TCA GGG ATC CCT GCG CGA

70
    F   S   G   S   N   S   G   N   T   A   T   L   T   I   S   G
TTC TCT GGC TCC AAC TCA GGG AAC ACC GCC ACC CTG ACC ATC AGC GGG 80                                          90
    V   E   A   G   D   E   A   D   Y   Y   C   Q   V   W   D   S
GTC GAG GCC GGG GAT GAG GCT GAC TAT TAC TGT CAG GTG TGG GAC AGT

100
    T   A   D   H   W   V   F   G   G   G   T   R   L   T   V   L
ACT GCT GAT CAT TGG GTC TTC GGC GGA GGG ACC CGG CTG ACC GTC CTA

109
    G
GGT
```

FIG. 14

RECOMBINANT ANTIBODIES FOR HUMAN THERAPY

FIELD OF THE INVENTION

This application is a divisional of application Ser. No. 08/379,072, filed Jan. 25, 1995, which is a continuation of application Ser. No. 07/912,292, filed Jul. 10, 1992, (now abandoned) which is a continuation-in-part of Newman et al., U.S. patent application Ser. No. 07/856,281, filed Mar. 23, 1992 (now abandoned), which is a continuation-in-part of U.S. patent application Ser. No. 07/735,064, filed Jul. 25, 1991 (now abandoned), the whole of which, including drawings, are both hereby incorporated by reference. This invention relates to recombinant antibodies useful for human therapy, and to methods for production of such antibodies.

BACKGROUND OF THE INVENTION

Murine monoclonal antibodies are used in diagnosis of human disease, and in solving basic biological research problems. These reagents are also used in clinical trials as therapeutics for both acute and chronic human diseases, including leukemias, lymphomas, solid tumors (e.g., colon, breast, hepatic), AIDS and autoimmune diseases.

Mouse/human chimeric antibodies have been created, and shown to exhibit the binding characteristics of the parental mouse antibody, and effector functions associated with the human constant region. See e.g., Cabilly et al., U.S. Pat. No. 4,816,567; Shoemaker et al., U.S. Pat. No. 4,978,745; Beavers et al., U.S. Pat. No. 4,975,369; and Boss et al., U.S. Pat. No. 4,816,397 all of which are incorporated by reference herein. Generally these chimeric antibodies are constructed by preparing a genomic gene library from DNA extracted from pre-existing murine hybridomas. Nishimura et al., 47 *Cancer Research* 999, 1987. The library is then screened for variable region genes from both heavy and light chains exhibiting the correct antibody fragment rearrangement patterns. The cloned variable region genes are then ligated into an expression vector containing cloned cassettes of the appropriate heavy or light chain human constant region gene. The chimeric genes are then expressed in a cell line of choice, usually a murine myeloma line.

Such chimeric antibodies have been used in human therapy. Antibodies to these chimeric antibodies, however, have been produced by the human recipient in a number of cases. Such anti-chimeric antibody antibodies are detrimental to continued therapy with the chimeric antibody.

Erlich et al., 34 *Clinical Chemistry* 1681, 1988, Erlich et al., 7 *Hybridoma* 385, 1988, Erlich et al., 6 *Hybridoma* 151, 1987, and Erlich et al., 1 *Human Antibody Hybridomas* 23, 1990 (not admitted to be prior art to the present application) state that human monoclonal antibodies are expected to be an improvement over mouse monoclonal antibodies for in vivo human therapy. They also postulate that non-human primate antibodies, e.g., chimpanzee monoclonal antibodies, to be tolerated in humans because they are structurally similar to human antibodies. Since human antibodies are non-immunogenic in Rhesus monkeys (i.e., do not induce an antibody response), they predict that primate antibodies will be non-immunogenic in humans. They indicate that the testing of antibodies in humans is unnecessary if a primate antibody has a constant region structure identical to that of a human immunoglobulin or, at least, a structure no more different from a human immunoglobulin than the different human antibodies differ from each other. Thus, they suggest that chimpanzee antibodies may be useful in human therapy.

SUMMARY OF THE INVENTION

The present invention concerns methods for the amplification and cloning of old World monkey (referred to herein as "monkey," e.g. baboon or macaque) antigen-binding portions of immunoglobulin variable region-encoding genes, the fusion of these genes to cloned human, chimpanzee or other monkey constant region-encoding genes (and human, chimpanzee or other monkey framework-encoding genes if required), and their expression as human/monkey recombinant antibodies, or wholly monkey recombinant antibodies. Furthermore, the invention concerns use of such recombinant antibodies (which term includes antibodies produced by fusion of DNA from two different antibody genes, even from the same species, e.g., two different monkey antibody genes, for example, Rhesus and cynomolgus monkeys, to give a monkey-monkey recombinant antibody) as immunotherapeutic agents for the treatment of human disease. The invention is based upon the discovery that evolutionary distant monkeys (e.g., baboon or macaque monkeys (including cynomologus, and Rhesus monkeys)), unlike the Chimpanzee, are not only sufficiently different from humans to allow antibodies against human antigens to be raised in these monkeys, even to relatively conserved human antigens, e.g., CD4 and CD54, but are sufficiently similar to humans to have antibodies similar to human antibodies, so that there is no host anti-antibody immune response when such monkey antibodies, or recombinant antibodies derived therefrom, are introduced into a human.

Unlike some prior antibodies used for human therapy, the antibodies of the present invention do not suffer from several drawbacks, e.g., 1) immunogenicity and induction of human anti-antibody (HAA) response upon repeated administration necessary to treat chronic conditions, 2) relatively short half-life compared to human antibodies, and 3) lack of effector functions with human cells or complement. The lack of these drawbacks is a significant advantage for human therapy with antibodies made by the present invention. For example, in the case of chronic human diseases, including auto-immune diseases, or any disease where prolonged administration of an antibody is necessary, one of the major obstacles to repetitive antibody therapy is the host response to the therapeutic antibody. HAA responses are often unpredictable from one patient to another. Such responses are predominantly, though not exclusively, directed against the constant region of the antibody molecule, and once they occur they often preclude, or reduce the effectiveness of, any further therapy with that antibody, or another antibody of the same isotype.

Potentially, the problems of HAA could be circumvented by the use of human monoclonal antibodies. This approach, however, suffers from the ethical, clinical, and immunological limitations on immunization of human subjects with many antigens of choice (e.g., human antigens, which phrase includes antigenic or immunogenic portions of any proteins, polypeptides or their equivalent present in a human) for antibody generation. Applicants' approach to circumvent this problem includes generation of antibodies of the appropriate specificity and desired effector function, and their use in production of recombinant antibodies. These recombinant antibodies generally include an appropriate portion of the variable region of an antibody derived from an immunized monkey, and the constant region of an antibody from a human or chimpanzee. Thus, the specificities and high affinities of monoclonal antibodies are retained, and the appropriate human or chimpanzee constant region displaying the desired effector functions can be readily chosen.

The present invention is further based on a method for amplification of monkey immunoglobulin genes, e.g., by the polymerase chain reaction (PCR), from RNA extracted from monkey lymphocytes using synthetic oligonucleotide primers specific for heavy and light chain variable region gene families. The amplified genes or appropriate portions (e.g., complementarity determining region (CDR)-coding regions; see Winter, British Patent Application No. GB2188638A, hereby incorporated by reference herein) are cloned into an expression vector containing a human or chimpanzee constant region gene for the production of a monkey/human recombinant antibody, or a vector containing a monkey constant region gene for the production of wholly monkey recombinant antibody of the desired isotype. These antibodies represent immunotherapeutic agents capable of localizing and/or killing appropriate target cells (e.g., tumor cells) after in vivo administration.

Thus, in a first aspect the invention features a method for cloning an antigen-recognizing portion of the variable region of a monkey antibody gene. This method includes providing nucleic acid, e.g., RNA from the monkey, forming cDNA to the RNA (using reverse transcriptase), providing a primer complementary to the cDNA sequence encoding a 5' leader sequence of the antibody gene, contacting that cDNA and the primer to form a hybrid complex and amplifying the cDNA to produce nucleic acid encoding the variable region of the monkey antibody gene.

By "antigen-recognizing portion" is meant one or more portions of a variable region of a monkey antibody which are responsible for binding and/or recognizing the target antigen (or epitope or idiotype) of the antibody. For example, it includes the CDR regions (see below) or the whole variable region, or any combination of these two regions including any changes in coding regions that may be induced to make the region more human-like rather than monkey-like, without altering the specific binding properties of the antibody. If only a portion of the whole variable region is used then the remaining portions, e.g., the so-called "framework", are provided from another antibody, preferably a human or chimpanzee antibody (see below) and in the art cited above and incorporated herein by reference.

The phrases "variable region", "leader sequence", "constant region" and "framework" are used in their common art recognized manner, examples of which are provided below and in the art cited above and incorporated herein by reference.

In preferred embodiments, the leader sequence is a human, chimpanzee or monkey leader sequence of approximately 60 bases, examples of which are provided in FIG. 1 (SEQ ID NOS: 1-19).

Applicant has discovered that the monkey, chimpanzee and human variable region leader sequences are sufficiently similar that primers constructed to one are suitable for amplification of the other. In the method, the RNA is amplified sufficiently to produce enough nucleic acid to place that nucleic acid within a vector for later cloning.

In a second aspect, the invention features a method for producing an antibody to a human antigen, which antibody is not immunogenic in humans. The method involves raising in a monkey a monkey antibody to the human antigen, and isolating monkey nucleic acid encoding an antigen-recognizing portion of a variable region of the monkey antibody. Human nucleic acid encoding a human constant region of an antibody is provided, and ligated to the monkey nucleic acid to form recombinant nucleic acid. This recombinant nucleic acid is then expressed to produce the desired antibody. Alternatively, chimpanzee or monkey constant region-encoding nucleic acid can be used to form the recombinant antibody. There are few, if any, differences in the amino acid sequence of human and chimpanzee constant regions (i.e., they are homologous), and those differences present between human and monkey can be readily altered by standard techniques if the nucleic acid encoding the monkey constant region is used to form a recombinant antibody. All that is critical in the invention is that an antibody be produced that is less immunogenic than the monkey constant region so that no significant immune response ensues when the recombinant antibody is introduced into a human. (Such antibody regions are herein referred to as homologous regions.) Thus, the recombinant antibody is engineered to be functionally the same as a human antibody in its amino acid sequence, i.e., it has a constant region homologous to a human or chimpanzee antibody constant region. In summary, the antibody is as human an antibody as is necessary to reduce the chance of an undesired immunological response to the antibody, and contains an antigen-binding portion of a monkey antibody.

By "not immunogenic" is meant that the antibody does not raise an antibody response of sufficient magnitude to reduce the effectiveness of continued administration of the antibody in the majority of humans for sufficient time to achieve therapeutic efficacy, e.g., as compared to a murine or murine-human chimeric antibody. Preferably, no antibody response is observed.

In preferred embodiments, the method includes immortalizing a cell of the monkey which is responsible for producing the monkey antibody, e.g., by hybridoma fusion, viral transformation with *Herpes papio*, single B-cell cloning (also termed "transient immortalization"), and production of a library of recombinant immunoglobulins. In other preferred embodiments, the method includes selecting a B-cell from the monkey from either a peripheral blood leukocyte, the spleen, bone marrow or a lymph node; selecting a clone which produces the appropriate antibody; rescuing the immunoglobulin genes encoding that antibody from the immortalized cell line; and reexpressing the genes in a producer cell line (i.e., a cell line which causes sufficient production of the antibody to be useful for human therapy).

In a third aspect, the invention features a recombinant antibody formed from either a human or chimpanzee constant region and an antigen recognizing portion of a monkey variable region, or a first monkey constant region and a second, different monkey antigen recognizing portion of a variable region.

In a related aspect, the invention features a monoclonal antibody, or an Fab, (Fab)$_2$, a light chain or heavy chain dimer, or any minimal recombinant fragment thereof, such as an Fv or a SCA (single chain antibody) or other immunologically active fragment thereof (e.g., a CDR-region), to a human antigen formed by an immortalized monkey B-cell. Such fragments are useful as immunosuppressive agents. Alternatively, the antibody of the invention may have attached to it an effector or reporter molecule. For instance, an antibody of the invention may have a macrocycle, for chelating a heavy metal atom, or a toxin, such as ricin, attached to it by a covalent bridging structure. In addition, the Fc fragment or CH3 domain of a complete antibody molecule may be replaced by an enzyme or toxin molecule, and a part of the immunoglobulin chain may be bonded with a polypeptide effector or reporter molecule. Bispecific antibodies can also be constructed by standard procedure.

In another aspect, the invention features pharmaceutical compositions in which antibodies of the present invention are provided for therapeutic or prophylactic uses. Such antibodies can also be provided as immunotoxins, i.e., molecules which are characterized by two components and are particularly useful for killing selected cells in vitro or in vivo. One component is a cytotoxic agent which is usually fatal to a cell when attached or absorbed. The second component, known as the "delivery vehicle" provides a means for delivering the toxic agent to a particular cell type, such as carcinoma cells. The two components are commonly chemically bonded together by any of a variety of well-known chemical or genetic procedures. For example, when the cytotoxic agent is a protein and the second component is an intact immunoglobulin, the linkage may be by way of heterobifunctional crosslinkers, e.g., carbodiimide, glutaraldehyde, and the like. Production of various immunotoxins is well-known in the art.

In another related aspect, the invention features nucleic acid encoding a human/monkey recombinant antibody. In preferred embodiments, the nucleic acid encodes a human or chimpanzee constant region and an antigen recognizing portion of monkey variable region; and the nucleic acid is purified, i.e., separated from biological components with which it naturally occurs, or more preferably, is provided as a homogeneous solution.

In yet another aspect, the invention features a CDR-grafted antibody formed from at least one of the complementarity determining regions (CDRs), that is, amino acid residues (using the standard amino acid labeling system of Kabat) 31-35 (CDR 1), 50-65 (CDR 2) and 95-102 (CDR 3) of the specified heavy chain, and amino acid residues 24-34 (CDR 1), 50-56 (CDR 2) and 89-97 (CDR 3) of the specified light chain of an Old World monkey variable region, and an immunoglobulin variable region framework from a second species. The CDR-grafted antibody is able to bind to the same antigen as the original monkey antibody. The antibody constant region is derived from a human or chimpanzee immunoglobulin. The methodology for performing this aspect is generally described by Jones et al., 321 *Nature* 522, 1986. Such CDR grafts can be altered if desired to ensure that they appear more human-like so that the probability of instigation of adverse reaction to the antibody is lessened.

In preferred embodiments, the method includes immortalization or selection of a cell from a macaque, which is responsible for producing a macaque antibody, and rescuing the immunoglobulin genes from the cell; cloning and sequencing the antibody genes responsible for the production of antibody; selecting a human variable region framework sequence (preferably with the closest homology to the macaque variable region framework); and substituting macaque CDR sequences for human CDR sequences and minor modifications in the human framework region may be included to maintain affinity of the antibody for its antigen.

By "minor modifications" is meant that less than a total of about 6 amino acids in the framework may be substituted by other amino acids. Usually such substitutions or modifications are made only when those amino acids are involved in conformational interactions that hold the framework in an appropriate form so that the desired antigen is recognized by the antibody. Such modifications will generally reflect those differing amino acids present in a monkey antibody, compared to a human antibody. For example, the amino acid sequence of a human antibody just prior to heavy chain CDR 3, 92-94 is generally cysteine-alanine-arginine (arginine is known to be replaced in a minority of antibodies with serine or threonine); in some antibodies in the monkey the sequence is cysteine-alanine-serine; thus, in this example, it may be preferred to use serine at amino acid 94 (SEQ ID NOS: 75-80) (see FIG. 9D).

In a further aspect, the invention features a method for treating a human having a particular antigen, e.g., one associated with disease. The method includes administering a therapeutically effective amount of a recombinant antibody specific for the particular antigen, wherein the recombinant antibody is one having either a human or chimpanzee constant region and an antigen recognizing portion of a monkey variable region, or a first monkey constant region and an antigen-recognizing portion of a second, different monkey variable region.

In preferred embodiments of the above aspects, the antigen is a tumor antigen, an antigen involved in an immune disorder, an antigen involved in an autoimmune response, a receptor expressed on a host cell, or an antigen selected from the human antigens CD58, VLA4 ($\alpha 4\beta 1$ integrin), CD2, LFA3, ELAM, LAM, CD25, CD4, CD19, CD20, human T-cell receptor, CD3, CD8, CD23, CD41, CD44, CD45, CD71, TNF$\alpha$, TNF$\beta$, Tn antigen, IL-1, IL-8, C5a, adhesion molecules, e.g., VCAM, CD54, CD28, CD11a, CD11c, CD18, and CD11b, the neu oncogene product, MDR-1 (P-glycoprotein), TGFA and its receptor, and PDGF; and the recombinant antibody is active to either deplete (kill or eliminate) undesired cells (e.g., anti-CD4) by acting with complement, or killer cells, or is active as a cytotoxic agent or to cause Fc-receptor binding by a phagocyte. Alternatively, the antibody blocks or stimulates receptor functions, or neutralizes active soluble products, such as one or more of the interleukins, TNF and C5a.

In other aspects, the invention features pharmaceutical compositions of the above antibodies or fragments thereof. Compositions or products according to the invention may conveniently be provided in the form of solutions suitable for parenteral or nasal or oral administration. Appropriate preparations of antibody may be mixed with appropriate preparations of other agents, resulting in increased clinical utility.

Other features and advantages of the invention will be apparent from the following description of the preferred embodiments thereof, and from the claims.

DESCRIPTION OF THE PREFERRED EMBODIMENTS

The drawings will first briefly be described.

Drawings FIG. 1 is a tabular representation of 20 codons in nine different Ig heavy chain leader sequences and ten monkey Ig heavy chain leader sequences (SEQ ID NOS: 1–19);

FIGS. 7A, 7B, 7C and 7D and 8 show the nucleic acid sequence of various leader sequence primers useful in the invention (SEQ ID NOS: 20–62);

FIGS. 9A through 9H are comparisons of human and monkey regions in the VH1, VH2, VH3, VH4, and VH5 sequences. and VKI and VKII. and VlambdaIII sequences. respectively (SEQ ID NOS: 63–92);

Figure 11:
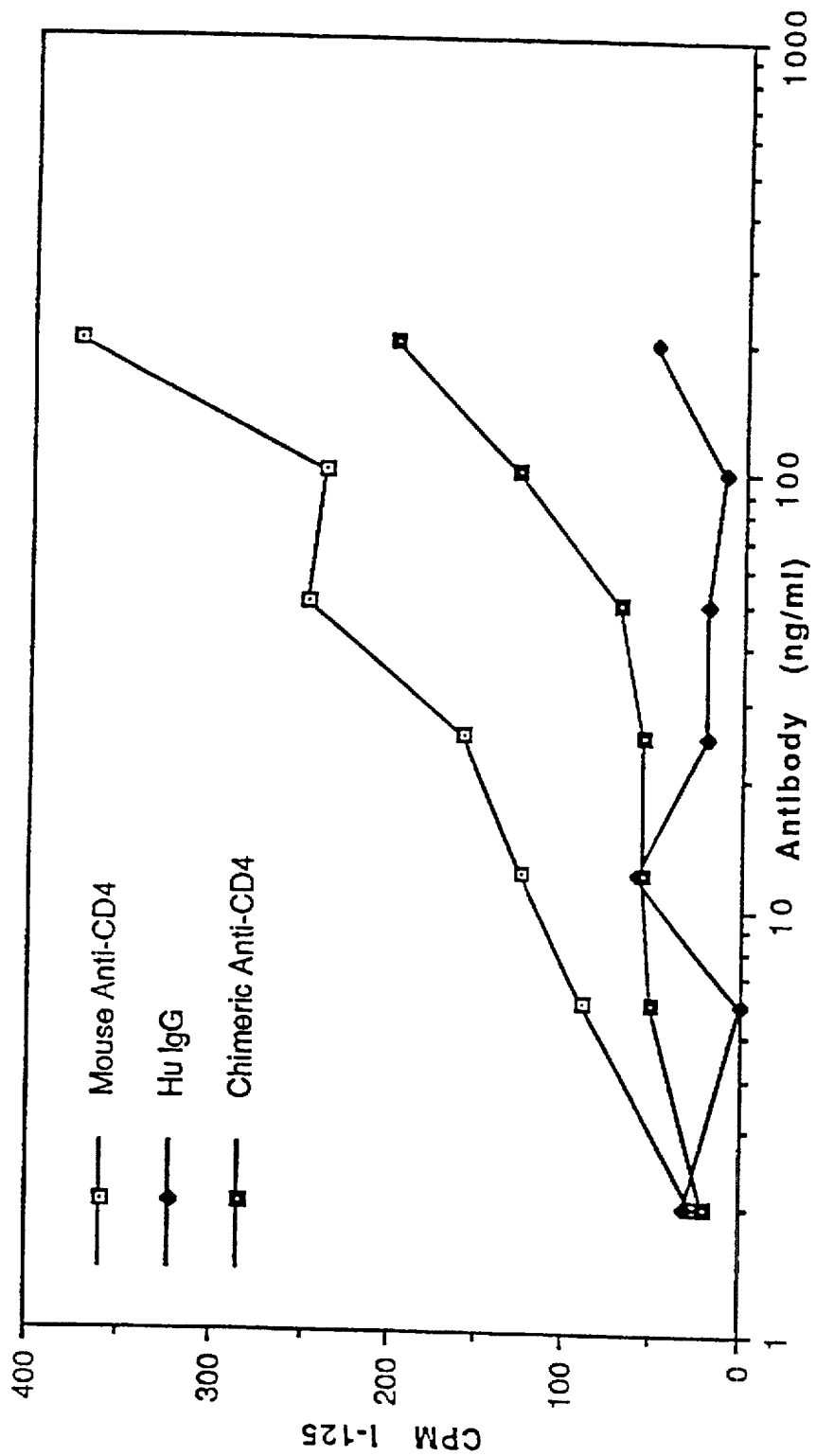
Figure 12:
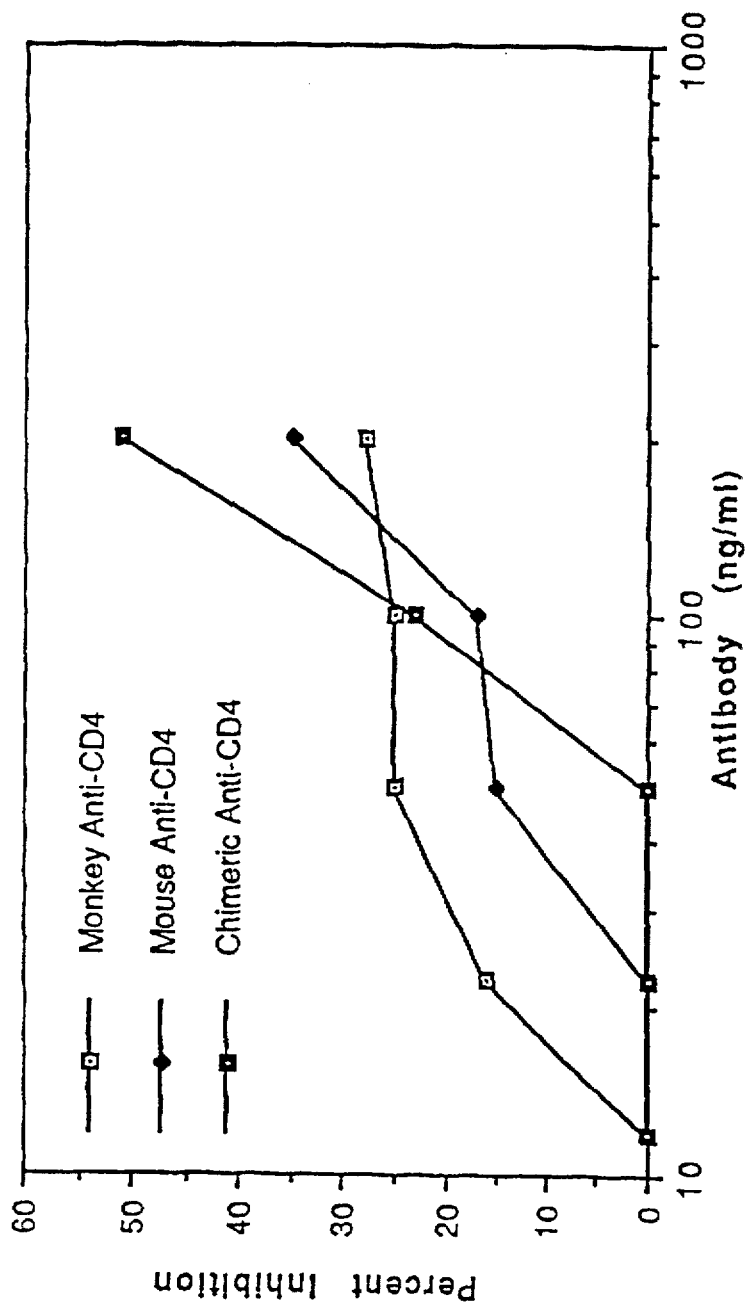
Figure 15:
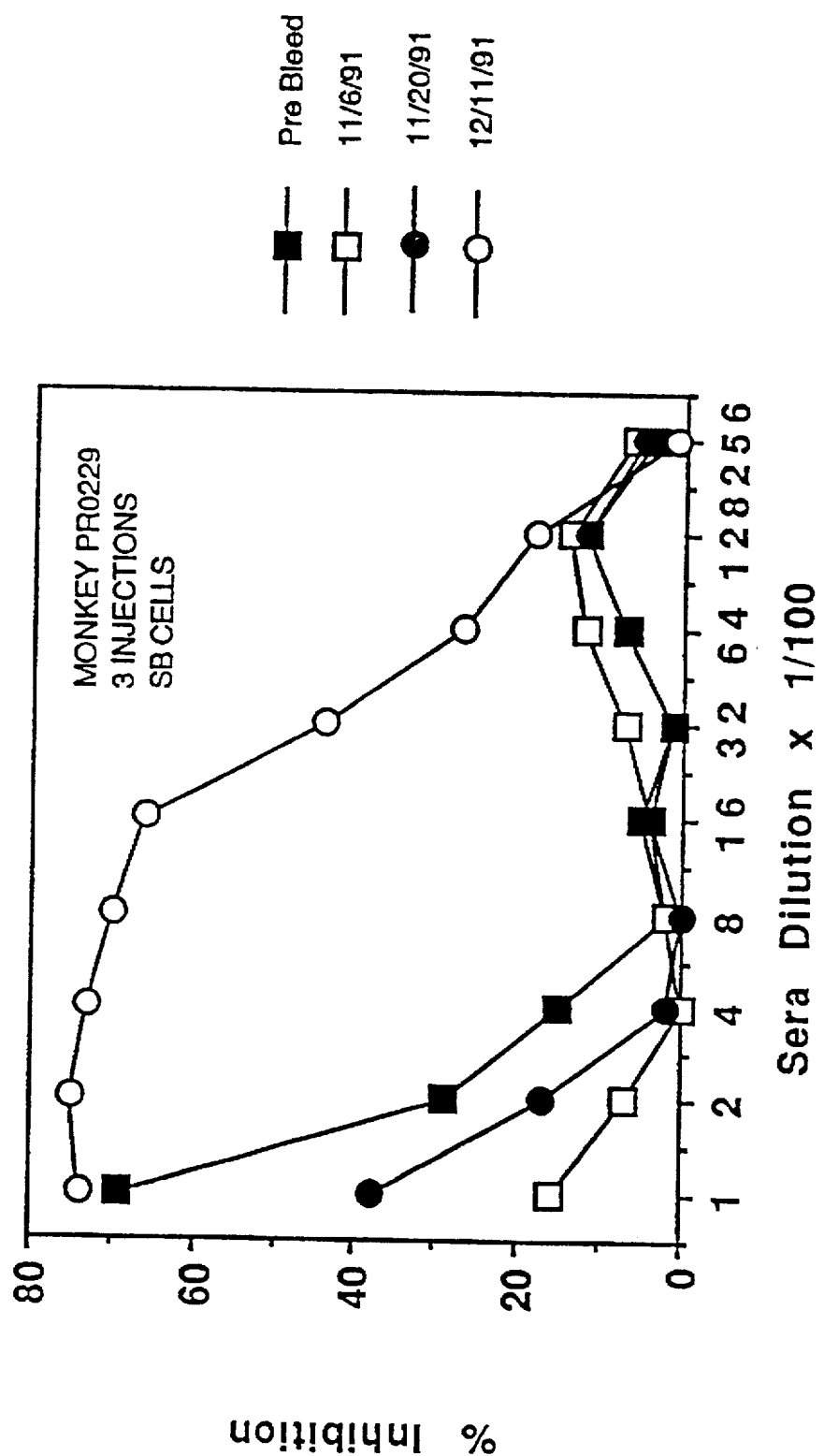

FIG. 10 is a comparison of human and monkey VH3 sequences. with one comparison to the human VH2 sequence (SEQ ID NOS: 93–106);

FIG. 11 is a graphical representation of the binding of an antibody of the invention to a human CD4 antigen;

FIG. 12 is a graphical representation of the inhibition of binding of 1F3 by the antibody shown in FIG. 10;

FIGS. 13 and 14 are portions of the nucleotide sequences of anti-CD4 VH. and VL regions respectively (SEQ ID NOS: 107–110);

FIG. 15 is a graph showing anti-CD54 activity; and

Figure 16:
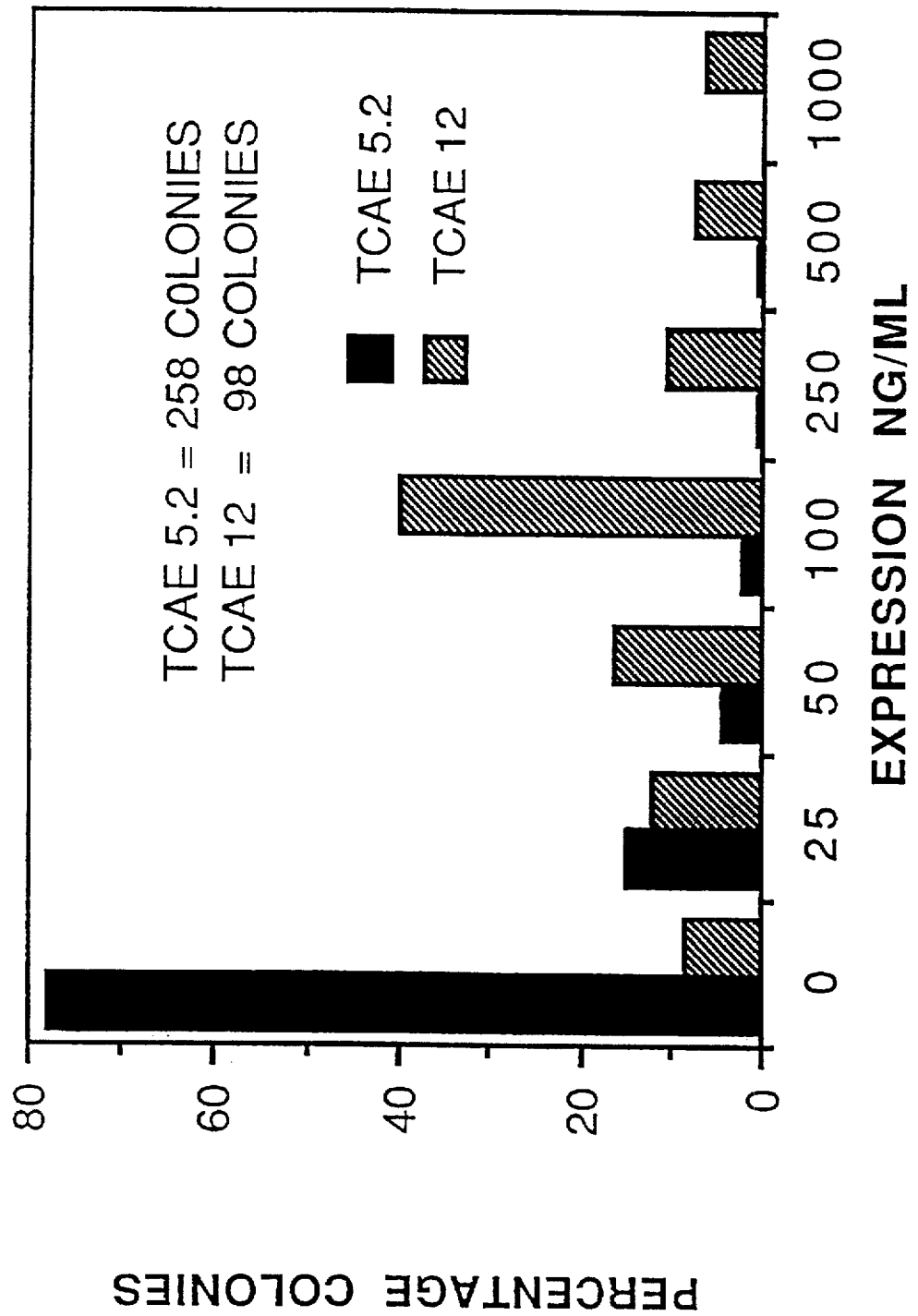

FIG. 16 is a histogram comparing plasmid expression features.

Monkey Antibodies

Old World monkeys include those referred to as baboon and macaque monkeys (including Rhesus monkey and cynomolgus monkey). This invention provides details of use of the claimed invention with various monkey genes. These examples are not limiting in the invention and may be readily applied to other Old World Monkeys.

Figure 2:
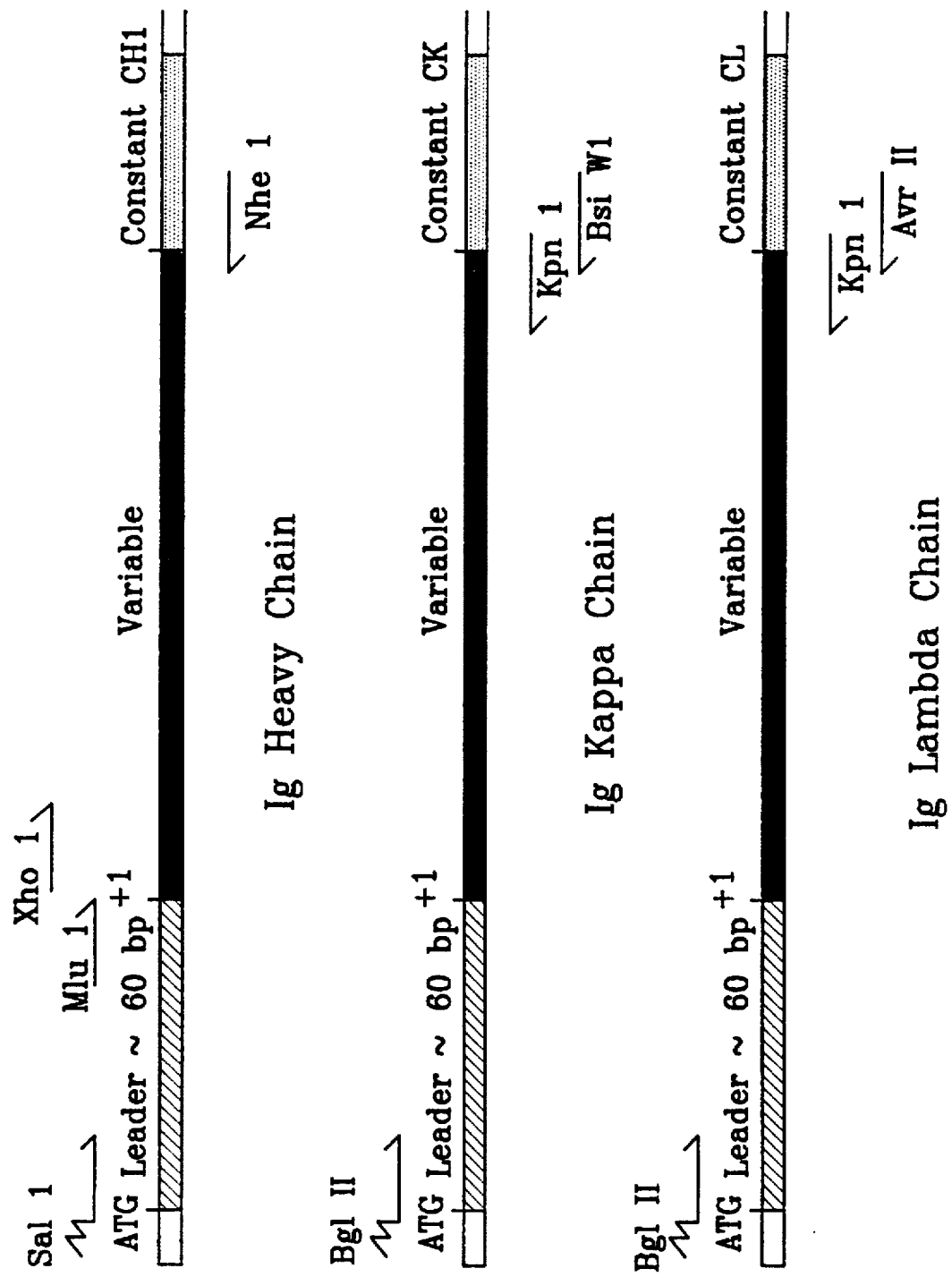
FIG. 2 is a diagrammatic representation of the structure of various Ig chains showing the relative position of leader, variable, and constant regions with the positions of restriction sites and primers used for amplification.

Referring to FIG. 2. there is shown in diagrammatic form the general structure of genes encoding immunoglobulin heavy. kappa light. and lambda light chains. Each of these chains is formed with an ATG start codon followed by a leader sequence of approximately 60 bases, a region encoding a variable region of the immunoglobulin. and a constant region of that immunoglobulin. Examples of different leader sequences. or signal peptides. of heavy chains are shown in FIG. 1. These sequences, and their equivalent in monkey, can be determined by standard techniques well known to those of ordinary skill in the art, and as described below.

The sequences shown in the lower portion of FIG. 1 are human leader sequences (SEQ ID NOS: 1–19). Applicants have discovered that construction of primers complementary to these leader regions allows amplification of Ig genes from monkeys.

Similarly. primers homologous to monkey leader sequences (see e.g.. upper portion of FIG. 1) can be used in amplification of monkey immunoglobulin genes. and also for amplification of human immunoglobulin genes.

By use of such primers in standard amplification procedures. genes encoding various monkey immunoglobulin genes. can be readily isolated, and the sequences encoding the variable regions of the antibodies determined.

Examples of such procedures are provided below. The results of the analysis provided below are presented in FIGS. 9A through 9H. and in FIG. 10 (SEQ ID NOS: 63–106). Surprisingly. applicant found that. despite the ability to produce antibodies to relatively conserved human antigens in the monkeys. the variable regional framework sequences of the antibodies so produced were indistinguishable from those of human antibodies. That is. the amount of variability in immunoglobulin sequence observed for the monkeys was similar to that observed for humans. and it was impossible to determine which antibody was derived from a human or monkey without analysis of the source itself.

Thus. for example. referring to FIG. 10 (SEQ ID NOS: 93–106). the amino acid sequence of the VH3 region of human was compared with monkey. The human antibodies showed a range of homology among themselves from 83–98%. while those of the monkey were from 90–95% homologous with the human VH3 region. In contrast. the human VH2 region was homologous to the human VH3 by 60%. [In this drawing. as in the other drawings. the presence of the same amino acid at any location is shown by a dash. while the presence of a different amino acid is shown by the standard one letter code. Positions to which no consensus amino acid can be assigned are shown as an X.] Similarly. homology for VH1. VH2. VH3. VH4. and VH5. and for VKI and VKII and Vlambda III is shown in FIGS. 9A–9H. respectively (SEQ ID NOS: 63–92). Again. significant homology between the monkey immunoglobulin region and that of the human was observed in each variable region including immunoglobulin J regions sequences. Such high homology is similar to that observed among human antibodies.

The methodology by which the sequences were determined is presented below in the examples. Those of ordinary skill in the art will recognize that these examples are not limiting in this invention and equivalent results and monoclonal and chimeric antibodies can be obtained by similar procedures well known to those of ordinary skill in the art. See e.g.. U.S. Pat. Nos. 4.816.567; 4.978.745; 4.975.369; 4.816.397. supra. For example. after cloning a gene encoding a monkey variable region. such a gene is readily ligated to one encoding a monkey or human constant region. and the fused genes expressed in a producer cell line to produce the desired antibody. Below are provided examples of such procedures.

In the following examples. the first step in the method involves the isolation of total RNA from monkey peripheral blood or spleen cells. B cells from immunized monkeys may be obtained from peripheral blood or lymph nodes and used directly or. they may be preferentially expanded. Expansion may involve Herpes papio virus transformation. fusion to a heterologous myeloma cell with subsequent selection. or cloning of single B cells under limiting dilution in the presence of stimulated human T cells.

Total RNA is then converted to single stranded (ss) cDNA by reverse transcriptase using non-specific (oligo-dT or random hexamers) or specific (immunoglobulin CH1 or CK or Clambda constant region) oligonucleotide primers. Single-stranded cDNA produced by this reaction is amplified using the polymerase chain reaction in which ss cDNA. together with deoxynucleotide triphosphates. a DNA polymerase (e.g.. a thermostable polymerase) and specific primers. are used to amplify heavy or light chain variable region immunoglobulin genes. The primers used are single stranded synthetic oligonucleotides ranging from 20 to 40 bases. containing some degenerate bases which bind to the immunoglobulin 5' leader sequences. Six different 5' leader sequence primers (see. FIG. 7-1 incorporating a restriction enzyme site (e.g.. SalI) have been designed for amplification of monkey heavy chain variable region families based on their similarity to human heavy chain variable region gene families. With each of the six 5' leader sequence primers. a 3' primer specific for the constant region domain of the relevant isotype (e.g.. IgG. IgM. IgA or IgE) also incorporating a restriction enzyme site (e.g.. NheI) is used. Similarly. for monkey kappa and lambda light chains. other pairs of primers are used for amplification of the appropriate light chain variable region (FIG. 7-2).

Other sets of primers can be used in order to incorporate different. unique restriction sites to allow directional cloning of PCR-amplified DNA into an appropriate expression vector possessing the same restriction site. A set of primers binding to the 3' end of the antibody heavy chain leader sequence incorporating a MluI site. or a set of primers binding to the first 23 bases of framework one incorporating a XhoI site can also be used and are described in FIG. 7-1.

The monkey immunoglobulin heavy and light chain variable region genes may be cloned into a shuttle vector directly after PCR amplification to allow further molecular manipulations if necessary or, cloned directly into an expression vector that contains human heavy or light chain constant region genes. The molecular configuration of the immunoglobulin genes in the expression vector may be genomic, in which immunoglobulin promoter/enhancer and other regulatory regions are present as well as splice donor/acceptor sequences at the intron/exon junctions. Alternatively, chimeric immunoglobulin genes can be inserted in a cDNA configuration using heterologous viral promoter/enhancer sequences.

EXAMPLE 1

Sequence of Monkey Antibodies

FIGS. 7 and 8 (SEQ ID NOS: 20-62) show the primers with or without restriction sites respectively, used in the PCR amplification of immunoglobulin genes from monkey and/or human cDNAs. Details of the procedures used are provided below. RNA was isolated from the spleen, peripheral blood and lymph node cells of monkeys using the standard guanidinium isothiocyanate method. The total RNA fraction isolated by this method was then used as a template for subsequent amplification reactions. An aliquot of the RNA was incubated in the presence of 200 units of Moloney murine leukemia virus reverse transcriptase and non-specific (oligo-dT or random hexamers) or specific (immunoglobulin IgG CH1 region or kappa chain constant region CK) oligonucleotide primers (50-100 picomoles) to generate a non-coding sense single cDNA strand. Single stranded cDNA produced by this reaction was then amplified using the polymerase chain reaction (PCR). An aliquot of single stranded cDNA was incubated together with deoxynucleotide tri-phosphates (20 µM), a thermostable DNA polymerase (2-5 units) and human-derived synthetic oligonucleotide primers (50 picomoles), to amplify either heavy or light chain variable region immunoglobulin genes.

Using pairs of primers shown in FIG. 8, several representative cynomolgus immunoglobulin heavy and light chain variable region sequences from a number of gene families were amplified. These amplified sequences were cloned into the EcoRV site of the plasmid vector p-Bluescript (pBS, available from Stratagene, CA) and used for DNA sequencing. DNA sequencing was performed using the plasmid DNA containing the cloned insert as a double stranded DNA template and the standard chain termination sequencing method.

Representative cynomolgus monkey immunoglobulin sequences are shown in FIGS. 9A-9H (SEQ ID NOS: 63-92). Included in FIGS. 9A-9H are the consensus amino acid sequence for human variable region genes representing each of the major variable region gene families. The percentage homology of each monkey sequence with the human consensus sequence, excluding the constant domain regions and the CDR regions, is shown. The level of homology between human and monkey sequences for a given family is as high as between two human sequences within that family. It is impossible therefore to distinguish between variable region immunoglobulin sequences originating from Old World monkeys, and those originating from humans based on sequence comparisons alone.

Isolation of RNA

Monkey antigen-specific B cells were obtained in several ways: by fusion of immunized monkey lymph node cells to the human/mouse heteromyeloma fusion partner cell line K5H6/B5, and subsequent screening of the hybridoma lines, by virally transformed B cells, or by in vitro single B cell cloning techniques. In the latter case growth of a single monkey B cell was supported in vitro by co-cultivation with human T cells that were stimulated by antibody. A single B cell was placed in each well of a 96 well tissue culture plate together with approximately 150,000 anti-CD3-stimulated mytomycin C-treated human T cells. After a two week incubation period the single B cell expanded to at least 200 differentiated plasma cells. Culture supernatant from these wells were assayed for the presence of immunoglobulin by ELISA technique using a capture antibody of goat anti-monkey immunoglobulin.

Cells either from antigen-specific virally transformed cells or hybridomas were grown up in sufficient numbers for extraction of RNA. Wells from the in vitro single B cell cloning technique that were positive for immunoglobulin were removed, washed twice with cold phosphate buffered saline pH 7.5 and centrifuged (1000×g 10 min). The washed cells were suspended in 100 µl of lysis solution (4M guanidinium isothiocyanate, 25 mM sodium citrate pH 7.0, 0.5% sodium sarcosine, 0.1M 2-mercaptoethanol). 10 µl of 2M sodium acetate, pH 4.0, was added and mixed. Protein was removed by adding 100 µl water saturated phenol, mixing and adding 20 µl of chloroform/isoamyl alcohol (49:1). After vortexing and incubation on ice for 15 min, the samples were centrifuged at 10,000×g for 20 minutes. The aqueous phase was transferred to a new tube, mixed with an equal volume of isopropanol and incubated for 1 hr at −20° C. The precipitate was collected by centrifugation at 10,000×g for 15 minutes, washed with 70% ethanol, recentrifuged and the pellet dried in a Speedivac (Savant). The dried RNA was redissolved a second time in 100 µl of lysis buffer. An equal volume is isopropanol was added and incubated at −20° C. for one hour. The precipitate was collected by centrifugation at 10,000×g for 15 minutes and washed with 70% ethanol. The pellet was dried in a Speedivac (Savant) and stored at −20° C. in 70% ethanol until use.

Synthesis of single stranded cDNA

The total RNA extracted from the cells originating from a single well was dissolved in 32 µl of double distilled water to which is added 1 µl (50-100 picomoles) of primer (either random hexamers, oligo dT or 3' immunoglobulin-specific primers) and 10 µl of 5X reverse transcriptase buffer (0.25 Tris-HCl pH 8.3, 0.375M KCl, 15 mM $MgCl_2$, 50 mM dithiothreitol). The mixture was heated at 65° C. for 5 minutes after which it was placed in ice for 2 minutes. After heating, 1 µl RNAsin (Promega), 5 µl of 5 mM deoxynucleotide triphosphates, and 1 µl (200 units) of Moloney murine leukemia virus reverse transcriptase (BRL) was added, and the mixture incubated at 37° C. for 1.5 hours. After completion of the reverse transcriptase reaction, the single stranded cDNA/RNA mixture was extracted with phenol/chloroform and passed through a 1 ml G-25 SEPHADEX spin column. The material passing through this column was used as template ss cDNA for PCR amplification.

Amplification of ss cDNA 3-10 µl of the ss cDNA was mixed with 10 µl 10X PCR buffer (500 mM KCl, 100 mM Tris-HCl pH 8.3, 15 mM $MgCl_2$), 1.6 µl of 1.25 mM deoxynucleotide triphosphates, 50 picomoles of specific immunoglobulin 5' primer, 50 picomoles of specific immunoglobulin 3' primer, and 2-5 units of thermostable DNA polymerase (Synthetic Genetics). The reaction volume was brought to 100 µl with water and overlaid with 100 μl of mineral oil. The reaction mixture was incubated at the following temperatures for the specified times.

94° C. for 1 minute
48° C. for 2 minutes
72° C. for 2 minutes

This cycle was repeated 30–35 times. The amplified products were examined by agarose gel electrophoresis using a 1.2% agarose gel and molecular weight standards. The amplified immunoglobulin variable region genes ran approximately between 350–500 bp markers. The PCR amplified products were then used for cloning into the appropriate plasmid vector.

EXAMPLE 2

Cloning Monkey Antibody Genes

Since monkey variable region gene sequences, at the cDNA level, are indistinguishable from human members of the equivalent gene family, immune responses to monkey/human chimeric antibodies, if any, are unlikely to be any different than those mounted against human antibody molecules.

Figure 6:
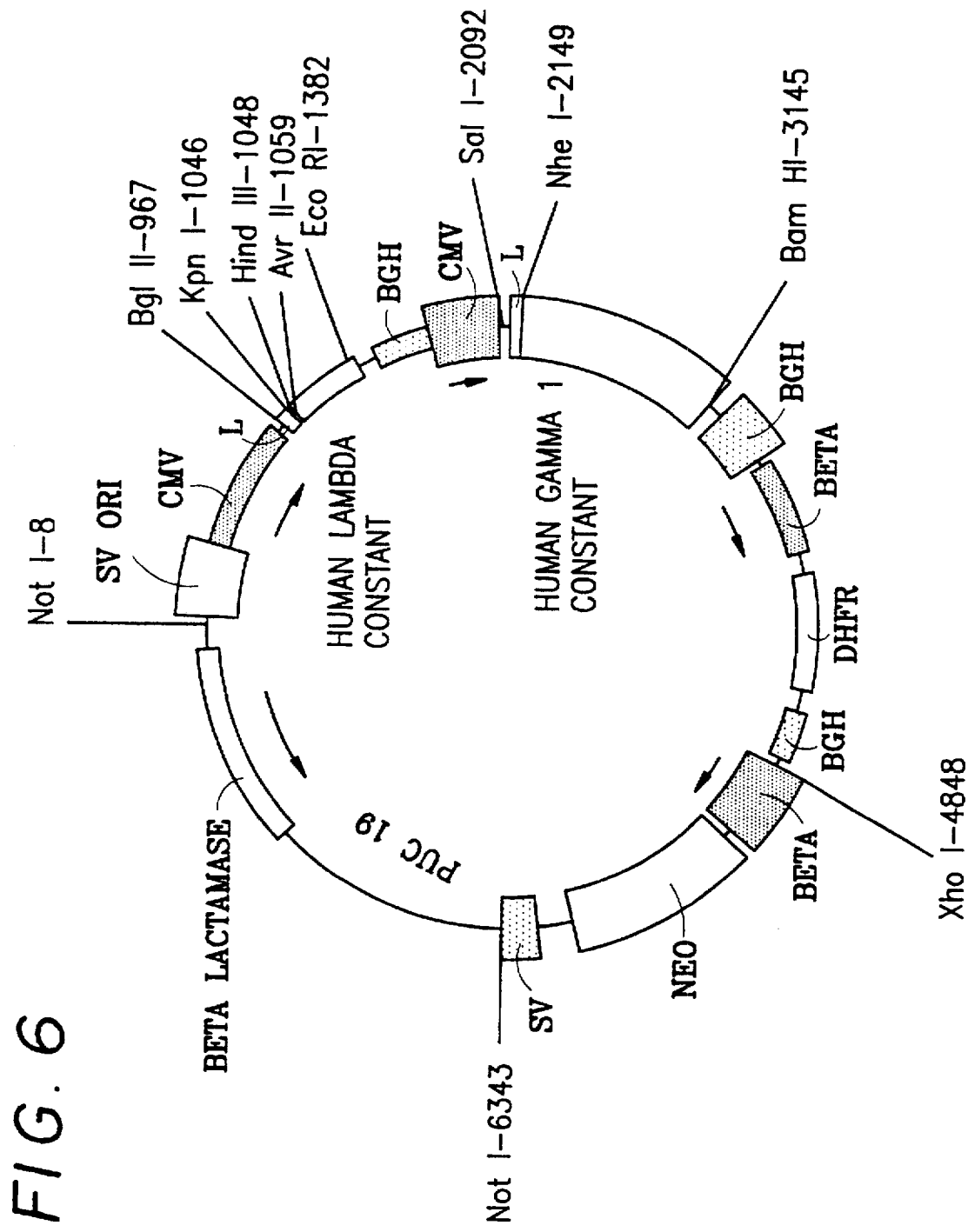

PCR technology can be used to introduce specific restriction enzyme sites, including (but not limited to) SalI, BglII, KpnI and NheI, into the Old World variable region sequences during the PCR amplification reaction using primers based on those in FIG. 6. Pre-existing cloned genes were amplified from their specific vector using these primers to introduce the specific restriction site which was subsequently used to clone the gene into an expression vector. Alternatively, these primers were used to amplify directly from cellular RNA.

Expression vectors which have been constructed are of two types. The first (see FIGS. 3 and 4) allows cloned cDNA immunoglobulin variable regions from monkeys to be inserted into a cassette vector, using unique restriction sites, in which the immunoglobulin gene elements are arranged in a genomic configuration. This type of vector incorporates an immunoglobulin promoter, the two exons making up the immunoglobulin leader sequence, two cloning sites SpeI and NheI, downstream splice donor sequences, an immunoglobulin enhancer region, a human constant region gene (heavy or light chain) and downstream polyadenylation signals. In addition, they include a bacterial origin of replication, a beta-lactamase gene for bacterial selection, and a neomycin phosphotransferase gene for G418 selection, or a xanthine-guanine phosphoribosyl transferase (gpt) gene for mycophenolic acid selection in mammalian cells. The heavy and light chain expression vectors use neomycin phosphotransferase (Neo) and xanthine-guanine phosphoribosyl transferase (Gpt) genes respectively as the selectable marker.

The second type of expression system (see FIGS. 5 and 6) uses immunoglobulin genes in a cDNA configuration. That is, no introns or splice sites are present between the 5' leader sequence and the 3' constant region sequences. This type of vector utilizes heterologous viral promoter/enhancer sequences, driving immunoglobulin heavy and light chain genes arranged in a tandem fashion, polyadenylation sequences and a selectable mammalian cell marker (Neo). The Neo gene can be modified to weaken its translation, e.g., by changing the codon upstream and adjacent the start site of the gene from ACC to TCT. In addition, a dihydrofolate reductase (dhfr) gene is present for subsequent gene amplification with methotrexate. Monkey immunoglobulin variable region genes to be cloned into cDNA configured expression vectors were amplified either from pre-existing cloned sequences in the shuttle vector (PBS), or directly from RNA with primers containing either the restriction sites SalI or MluI and NheI, for heavy chain, or BglII and KpnI or BsiWI for kappa or lambda light chains. Other potential unique restriction sites however are not excluded.

Chimeric heavy and light chain immunoglobulin genes were introduced separately or sequentially (for genomically configured constructs), or on the same vector (for cDNA configured constructs), by electroporation into a producer cell line. Electroporation was used to introduce linearized DNA constructs into either Chinese hamster ovary (CHO) cells, or mouse myeloma cells, followed by single cell cloning of the transfectants into 96 well tissue culture plates. Electroporation conditions using a BTX-100 (BTX, San Diego) electroporation device and a 1 ml disposable plastic cuvette gave optimal numbers of transfectants from a given amount of vector DNA. CHO cells that were adapted to grow in suspension in serum-free medium (CHO-S SFM II minus hypoxanthine and thymidine, Gibco) were used in constructs containing viral regulatory elements.

Subcloning Ig variable region genes

The products of the PCR reaction were extracted with phenol/chloroform and passed through a 1 ml SEPHADEX G-25 spin column. If the DNA fragment was to be blunt end cloned into a plasmid 1 μl 1M MgCl$_2$, 0.5 ml of 1.25 mM deoxynucleotide triphosphates and 1 μl of Klenow DNA polymerase (5 units) was added to the total PCR reaction mixture (100 μl) and incubated at 37° C. for 15 minutes to fill in any 5' overhangs. Before blunt end cloning into a plasmid, the 5' ends were phosphorylated as follows; 5 μl of 10 mM ATP, 1 μl of T4 polynucleotide kinase (10 units) were added to the total reaction mix and incubated at 37° C. for 30 minutes. Amplified fragments that contained internal restriction sites were first cut with the appropriate restriction enzyme and used directly for ligation without phosphorylation. In both cases the fragment to be cloned was extracted with phenol/chloroform before ligating into the appropriate vector.

For the ligation reaction 10% of the phosphorylated or restriction enzyme cut-PCR amplified fragment was mixed with approximately 2 ng of appropriate vector (total volume 8 μl), previously digested with the restriction enzyme(s). For blunt end-cloning pBluescript digested with EcoRV was used. For sticky end cloning the vector TCAE 5.2 or 6.0 or pGenex-H or pGenexL, cut with appropriate restriction enzymes was used. 1 μl of 10X ligation buffer (500 mM Tri-HCl pH 7.6, 100 mM MgCl$_2$, 10 mM ATP, 10 mM dithiothreitol), 1 μl T4 DNA ligase (1 unit) was added and the reaction allowed to proceed at 14° C. overnight. The ligated material was used to transform competent E. coli HB101 cells using the standard calcium chloride method of transformation. The transformed bacteria were selected by growth on LB ampicillin-containing agar plates. Individual colonies were selected and grown up overnight in LB medium containing ampicillin and plasmid DNA extracted using the standard alkaline lysis method. After restriction analysis to determine which clones contained immunoglobulin inserts, the DNA was prepared for sequencing.

Sequencing cloned genes

Cloned immunoglobulin variable region genes were sequenced using a standard chain termination method. Double stranded plasmid DNA containing the cloned insert was used as the sequencing template. Before sequencing, the double stranded DNA was chemically denatured. DNA was sequenced using T7 DNA polymerase SEQUENASE (United States Biochemical Corporation, Cleveland, Ohio), radiolabeled alpha deoxyATP, and the following sequencing primers (SEQ ID NOS: 111–112): (5' CAGAGCTGGG-TACGTCCTCA 3') and (5' GCCCCCAGAGGTGCTCT-TGG 3') for immunoglobulin G heavy chain variable region in 5' to 3' and 3' to 5' directions respectively. (5' CAGAGCTGGGTACGTGAACC 3') and (5' GGCT-TGAAGCTCCTCAGAGG 3') for immunoglobulin lambda light chain variable region in 5' to 3' and 3' to 5' directions, respectively (SEQ ID NOS: 113–114). Reaction products were separated on 6% polyacrylamide gels and read.

The results of sequencing a number of Old World monkey immunoglobulin heavy and light variable region genes are summarized in FIGS. 9A–9H (SEQ ID NOS: 63–92). Cloning and sequencing cynomolgus immunoglobulin genes has not been previously described in the literature. Nor, therefore, has the degree of homology between human and cynomolgus V region genes been possible to define. The homology between a single chimpanzee variable lambda gene and its human genomic counterpart has been described showing only a 2% difference in the framework regions.

Transfection and selection

Figure 3:
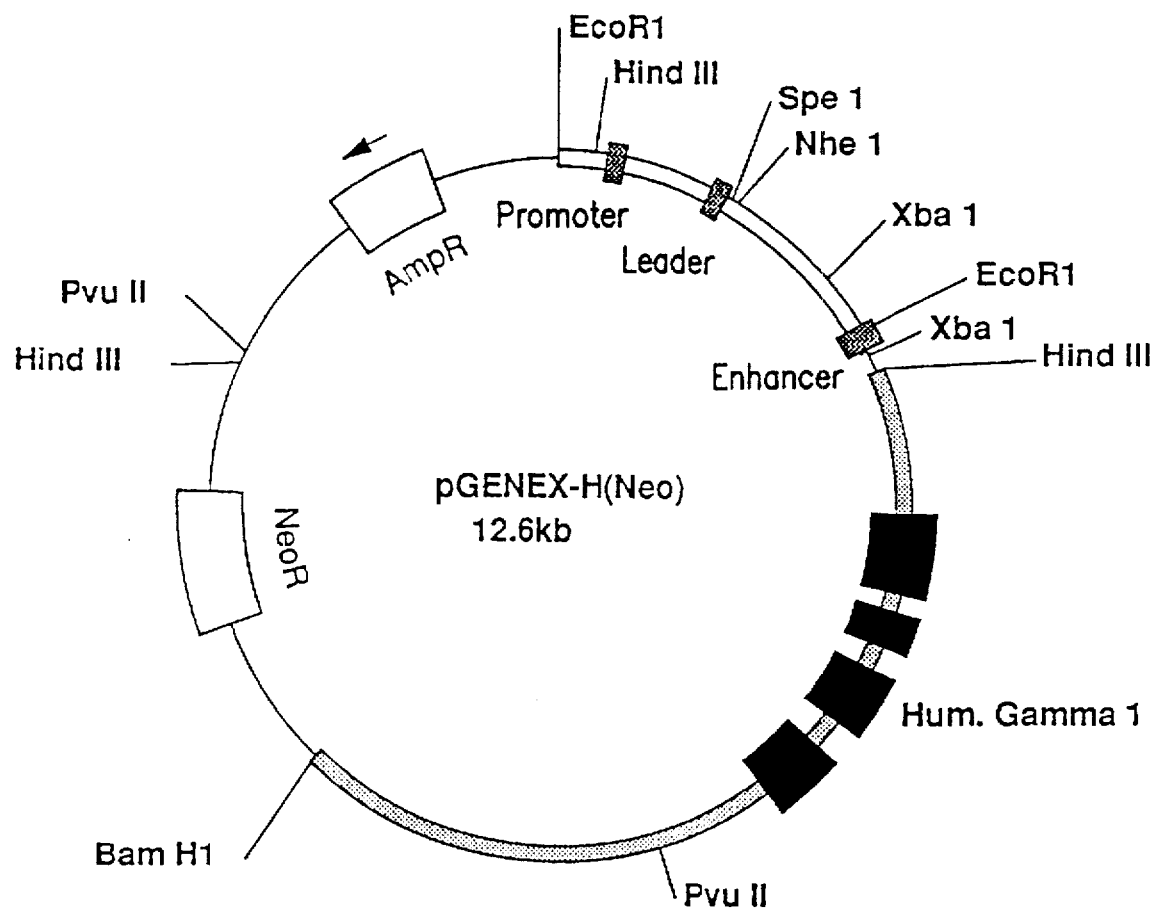
FIG. 3 is a diagrammatic representation of a heavy chain cassette vector for expression of human or chimeric antibodies.
Figure 4:
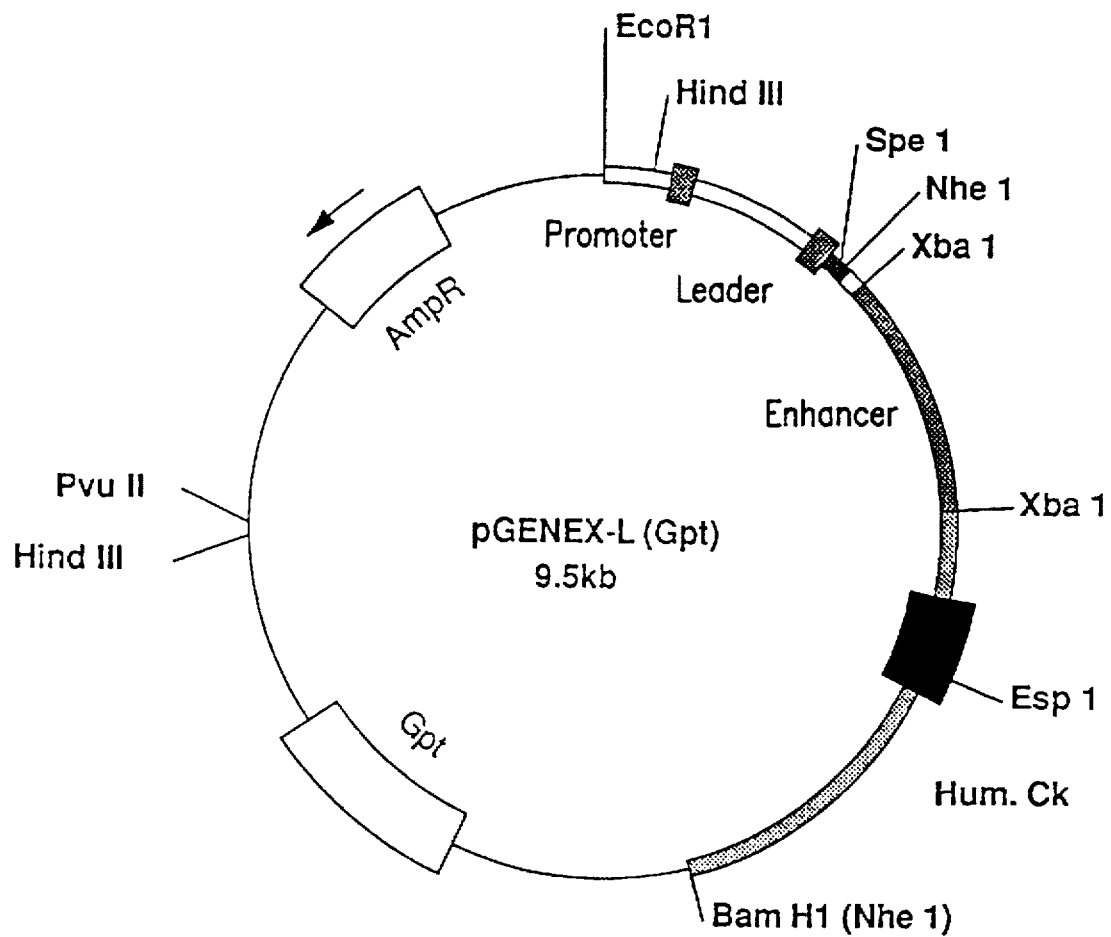
FIG. 4 is a diagrammatic representation of a light chain cassette vector designed for expression of human or chimeric antibodies.
Figure 5:
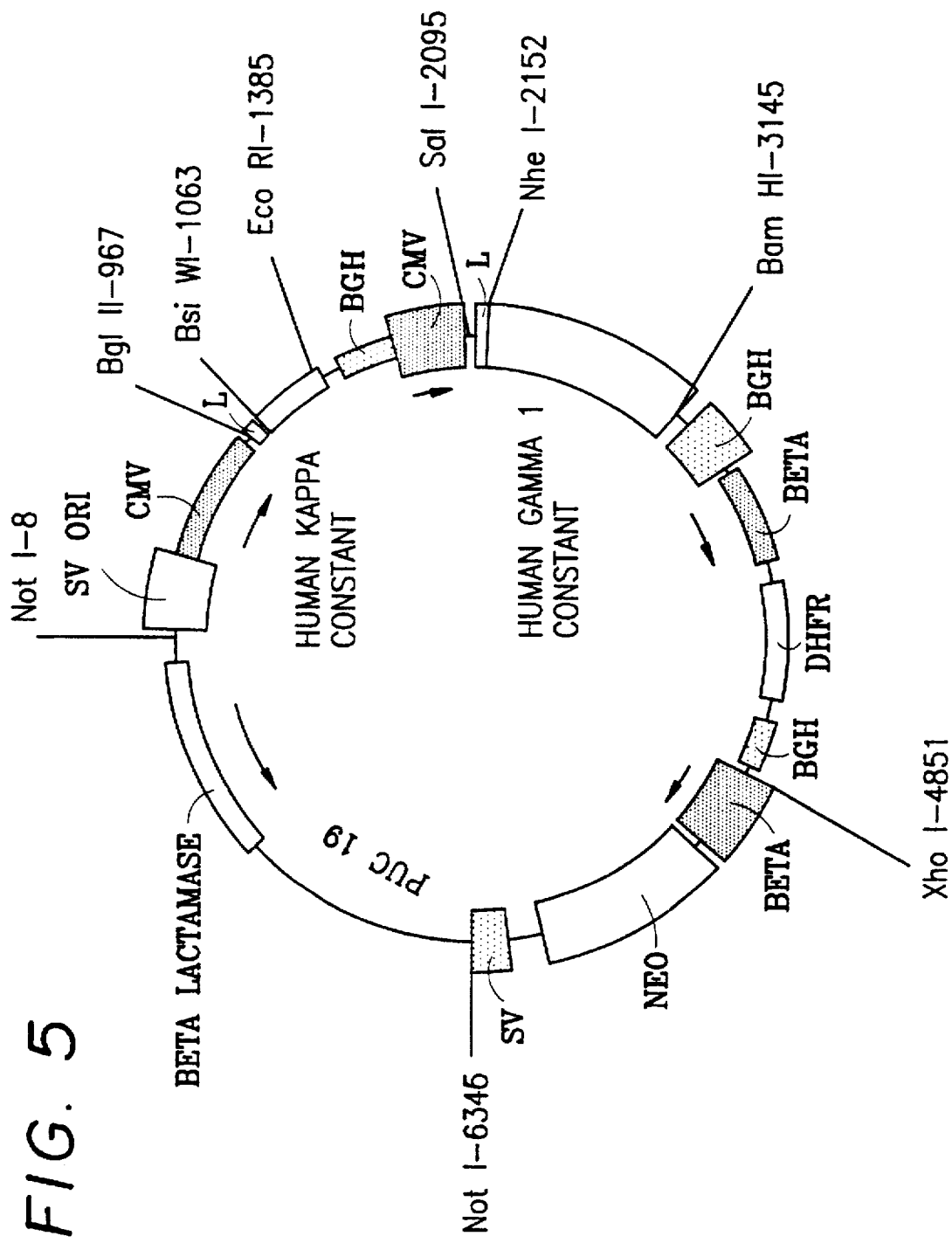
FIGS. 5 and 6 are diagrammatic representations of vectors designed for expression of immunoglobulin from kappa or lambda light chain cDNA, respectively. In these vectors, the immunoglobulin genes are arranged in a tandem configuration using neomycin phosphotransferase as the selectable marker.

After sequencing cloned heavy and light chain variable region genes, they were sub-cloned into appropriate vectors for expression. These may be vectors constructed with immunoglobulin regulatory elements in a genomic configuration (as shown in FIGS. 3 and 4), or with viral regulatory elements using a cDNA configuration (FIGS. 5 and 6). Appropriate restriction sites (SpeI and NheI) can be designed into the PCR amplification primers during the initial amplification step, or conversely amplification primers containing restriction sites can be used to amplify immunoglobulin genes from the shuttle vectors into which they have been cloned. Alternatively, immunoglobulin variable region genes may be cloned directly into expression vectors after PCR amplification from RNA, so that subcloning is unnecessary.

Electroporation

Electroporation was used to either co-transfect heavy and light chain genomic constructs or sequentially transfect heavy and light chain genomic constructs into Sp2/0 cells. In sequential transfections electroporation of the chimeric light chain construct was followed by selection in mycophenolic acid. Screening culture supernatants from clones, grown in 96 well plates, for light chain production with antisera against human light chain constant region using an ELISA technique, allowed selection of the highest light chain expressing clones. Subsequent electroporation of light chain transfectants with a vector containing the monkey/human chimeric heavy chain immunoglobulin construct allowed the selection of transfectomas expressing chimeric antibody of the desired specificity and isotype.

The light chain construct pGENEX-L (FIGS. 3 and 4) was transfected into the murine myeloma cell line Sp2/0 by electroporation as follows. SP2/0 cells at a concentration of $1\times10^7$/ml in transfection buffer (272 mM sucrose, 7 mM sodium phosphate pH 7.4, 1 mM MgCl$_2$) were mixed with 50 ug of pGENEX-L containing the appropriate cloned light chain gene, which had previously been linearized by digestion with the restriction enzyme PvuII. The cells were placed into a 1 ml disposable plastic spectrophotometry cuvette and plate electrodes 3.5 mm apart inserted into the cuvette. Using a BTX-100 (BTX, Inc.) transfection apparatus the cells were given a pulse of current for 500 microseconds such that approximately 50% cell death occurred. This value was determined prior to the transfection by pulsing the cells, in the absence of DNA, with increasing voltages and measuring the numbers of cells surviving 24 hours later. The voltage versus cell viability was plotted graphically and the voltage corresponding to 50% cell death used for all subsequent electroporation experiments. Using the BTX-100 apparatus, the optimal value was found to be a pulse at an amplitude of 200 for 500 microseconds. After pulsing the cells, they were allowed to recover on ice for 15 minutes before being transferred to 96-well tissue culture plates in Dulbecco's modified Eagle's medium (DMEM) containing 5% fetal calf serum and 10% Sp2/0 conditioned medium. Cells were plated at a concentration at which cell growth was seen in approximately 1 in 3 of the wells after selection with the appropriate drug. This parameter was determined for each electroporation experiment by plating varying numbers of electroporated cells per well (1000–10,000) and selecting for cells which have incorporated the plasmid. The number of wells on each plate which showed cell growth was counted after 2–3 weeks of selection. Thus, the appropriate number of cells that gave 1 out of 3 positive wells with a given concentration of a particular plasmid was determined for use in future experiments.

Directly after electroporation cells were placed in medium without drug. Fresh medium was added two days after electroporation containing either G418 or mycophenolic acid for cells exhibiting neomycin phosphotransferase or guanasyl phosphotransferase activity respectively. Cells were fed every 2 days for the first week and then twice a week thereafter. The concentration of drug to use was determined by incubating cells in the presence of increasing concentrations of drug and monitoring cell viability. The concentration of drug used was twice that which gave 100% killing. For Sp2/0 approximately 1 μg mycophenolic acid/ml was required and for G418 approximately 800 μg/ml.

Cells were electroporated in several ways, either heavy and light chain genomic vectors (pGenex-H and pGenex-L) were co-electroporated, or the light chain was electroporated alone. In the latter case, clones were screened for high level expression of chimeric immunoglobulin light chain using an ELISA technique. These clones were then grown up and electroporated with heavy chain containing vector. If cDNA tandem gene constructs were used, the expression vector (TCAE5.2 or TCAE6) was first linearized by digestion with the restriction enzyme NotI. A single electroporation was sufficient to achieve integration of both heavy and light chain genes. After 2–3 weeks supernatants from wells which continue to grow in the presence of appropriate drug were assayed for the secretion of chimeric immunoglobulin light chain or whole immunoglobulin using an ELISA technique. Immunoglobulin genes in a cDNA configuration were electroporated into either Sp2/0 cells, as described above, or into Chinese Hamster Ovary (CHO) cells adapted to grow in suspension in serum-free medium. CHO cells were electroporated using a BTX 600 electroporation apparatus, set at conditions for achieving maximal numbers of G418 resistant colonies. These were 210 volts, 400 μF and 13 ohms. After electroporation, cells were counted, washed in transfection buffer, resuspended in the same buffer and placed on ice for 15 minutes. Cells were adjusted to $1\times10^7$ live cells/ml and 400 μl of cell suspension placed in a 0.4 ml sterile disposable cuvette (BTX Inc.). 25 μg of Not 1 linearized TCAE 5.2 or TCAE 6 vector DNA, containing cloned macaque immunoglobulin variable region genes, were resuspended in TE buffer (10 mM Tris, 1 mM EDTA, pH 8.0) at 1 μg/ml and added to the cell suspension. Electroporation was carried out by discharging the apparatus using the automatic charge and pulse button. The cuvette was placed on ice for 15 minutes, the cells diluted into 120 mls of serum-free medium and placed into six 96-well plates (200 µl per well containing approximately 6,667 electroporated or 3,333 live cells per well). Independent electroporation parameters were established for this cell line and selection by G418 was at 400 µg/ml.

Screening for production of antibody

The presence of human, monkey or chimeric antibody secreted by transfectants was assayed by an ELISA technique as follows: 96-well flat bottom plates (Dynatech) were coated with goat anti-human IgG or kappa at 200 ng/well in Coating Buffer (sodium carbonate 0.8 mg/ml, sodium bicarbonate 1.55 mg/ml, pH 9.6) and incubated for at least 16 hr at 4° C. The coating buffer was removed and the wells blocked with 120 µl of Blocking Buffer (1% bovine serum albumin in phosphate buffered saline containing 0.2% sodium azide) and incubated at 37° C. for 1 hr. Up to 125 µl of cell culture supernatant was added to the wells containing blocking buffer and incubated 2 hrs at 37° C. The plates were then washed five times with PBS. 100 µl of horse radish peroxidase-labeled goat anti-human IgG (or kappa) diluted 1:1000–1:5000 in Dilution Buffer (1% bovine serum albumin, 0.05% Tween-20, 0.02% sodium azide in PBS) was added. Plates were incubated at 37° C. for 1 hr then washed five times with PBS. Chimeric antibody was detected with 100 µl of hydrogen peroxide and the substrate, 3,3',5,5'-tetramethylbenzidine (1:1 v/v) per well. The color reaction was terminated after 2 to 5 min. with 100 µl of 2M sulfuric acid per well.

Those of ordinary skill in the art can readily perform equivalent methodologies to those described above. Examples of such technology include immortalization of selected B-cells by hybridoma fusion, as described above, with the cell line K5H6/B5 described by Carroll et al., 164 *J. Experimental Medicine* 1566, 1986, or an equivalent cell line, such as SPAZ4 (available from Sandoz, see, Ehrlich et al., 34 *Clin. Chem.* 1681, 1988). Similar cell lines can be readily constructed by standard techniques using publically available methodology. Alternatively, immunoglobulin genes may be cloned from: (a) cells immortalized by viral transformation with *Herpes papio*, as described by Markova et al., 30 *Vopr Virusol* 549, 1985, or with an equivalent virus, (b) by single B-cell cloning to provide a transient immortalization, as described by Amaroso and Lipske 145 *J. Immunology* 3155, 1990, or (c) by use of a recombinant immunoglobulin bacteriophage libraries, as described by Huse et al., 246 *Science* 1275, 1989 and McCafferty et al., 348 *Nature* 552, 1990. Screening for appropriate antibody containing clones can be performed by those techniques described above, or equivalent techniques well known to those of ordinary skill in the art, and the desired immunoglobulin gene rescued from the immortalized cell line. In addition, the antibody produced by isolated monkey B cells can be used in human therapy, without manipulation to form a chimeric antibody.

The human constant region may be obtained by standard techniques, with any desired isotype well known to those of ordinary skill in the art, and the variable region of a monkey antibody ligated with that human constant region. Particularly useful chimeric antibodies against specific cell surface receptors which can be used in immunotherapy of humans include CD4, ICAMs, CD19, CD20, CD8, CD11a, CD11b, CD28, CD18, CD45, CD71, and TCR.

EXAMPLE 3

Cloning and Expressing a Monkey/Human
Chimeric Antibody with Specificity for CD4

The following is a specific example of the methods and antibodies of this invention.

Generation of Monkey Immortalized B-cell Lines

An adult cynomolgus monkey (White Sands New Mexico Primate Center) was immunized intramuscularly, at multiple sites, with 150–300 µg of soluble CD4 (sCD4) or cell membranes ($1\times10^8$ cells) from the CD4 positive cell line supT1 using a standard adjuvant. Immunization was repeated every 2–3 weeks a total of six times. The monkey was boosted by injection of 100 µg of sCD4 into the inguinal region of one thigh and one week later the draining lymph node from the same thigh surgically removed. Lymphocytes were removed from the lymph node by slicing the tissue and rinsing with sterile DMEM medium. The cell suspension was passed through a nylon gauze and collected by centrifugation at 1000×g for 10 minutes.

Approximately $1\times10^8$ lymphocytes were suspended in Tris-ammonium chloride buffer (16 mM, pH 7.5) and warmed to 37° C. for 5 minutes to lyse the erythrocytes. Lymphocytes were collected by centrifugation and resuspended in L-leucine methyl ester (LME) and incubated at 37° C. for 45 minutes. The LME treated cells were filtered through a nylon screen and centrifuged. 1 ml of fetal calf serum was added, the cells suspended and washed twice in serum-free RPMI. The cells were counted and mixed into a single 50 ml conical centrifuge tube together with an equal number of K6H6/B5 heteromyeloma cells, prewashed twice in serum free medium. Cells were gently suspended in 1 ml of 50% PEG (polyethylene glycol) added slowly with gentle stirring over a 1 minute period. The cells were then resuspended by the addition of 20 ml of serum-free medium over a 5 minute period, with gentle mixing to dilute out the PEG. After washing twice with serum-free medium cells were resuspended at a concentration of $5\times10^5/0.1$ ml in RPMI medium, containing 20% fetal calf serum and gentamycin and placed into 96 well micro tissue culture plates at 0.1 ml per well. An equal volume of HAT medium (0.1 ml) was added to each well and the hybrids allowed to grow for 14–17 days before screening.

Screening of Fused Cell Hybrids for the Production of Anti-CD4

The assay to determine anti-CD4 specificity was as follows: ELISA plates were coated with recombinant sCD4 at a concentration of 100 µg per well and blocked with 1% bovine serum albumin in PBS. 50 µl aliquots of hybridoma supernatant were removed from each well and allowed to incubate with the sCD4 coated plates for 60 minutes. Binding was detected by incubation with $^{125}$I labeled goat anti-human or goat anti-monkey Ig for 60 minutes. After washing four times with distilled water, the wells were counted in a gamma counter. Positive wells were re-assayed in duplicate and the hybridoma cells from those wells subcloned three times, first at 5 cells per well then twice at 1 cell per well. At this stage anti-sCD4 positives were screened for the ability to bind to cell surface CD4. This was done by inhibition of binding of an anti-CD4 murine monoclonal, termed 1F3, to the CD4 positive cell line supT1. Briefly this was done by co-incubating different amounts of monkey anti-CD4 and long of $^{125}$I-labeled 1F3 with $3\times10^5$ supT1 cells/well in a 96 well plate. After incubation for 1 hour at room temperature (about 20°–25° C.) cells were removed by vacuum onto glass fiber filters. After extensive washing with PBS the filters were counted in a gamma counter to determine the inhibition of 1F3 binding to supT1 cells by the monkey hybridoma supernatants.

A candidate clone was chosen which produced an antibody that showed strong inhibition against 1F3. The clone we chose was isotyped using human isotyping reagents and found to be an IgG2 possessing a lambda light chain. This cell line was grown up to larger numbers for cloning of its immunoglobulin genes.

Cloning of Heavy and Light Chain Variable Region Genes from Monkey Immortalized B-cells Total RNA was isolated from 1×10⁷ monkey immortalized B-cells using the guanidinium isothiocyanate method described above. One tenth of the total RNA was used to make single stranded cDNA using an oligo-dT oligonucleotide primer and reverse transcriptase, also as described above. One tenth of the amount of ss cDNA was used to set up PCR reactions. The six PCR reactions each included one of six 5' $V_H$ family specific oligonucleotide primers containing a Sal I restriction site together with an IgG 3' constant region oligonucleotide containing an Nhe I site, both shown in FIG. 7-1. Similarly, five PCR reactions, utilizing one of five 5' lambda leader sequence oligonucleotide primers containing a Bgl II site and a 3' lambda constant region prime containing an Avr II site, were run. Reaction conditions were as described above. Each PCR reaction was run in triplicate. The products of each of the heavy chain and light chain amplification reactions were run on 1.2% agarose gels. The VH4 heavy chain primer (SEQ ID NO: 23: 5' ACTAAGTCGACATGAAACACCTGTGGT-TCTT 3') and lambda primer (SEQ ID NO: 43: (5' ATCA-CAGATCTCTCACCATGACCTGCTCCCCTCTCCTCC 3') gave strong bands on agarose gel electrophoresis. The products of these reactions were used for cloning into the vector TCAE 6, which contains human IgG1 and human lambda constant region sequences.

Cloning of the two variable region genes into the expression vector TCAE 6 was done sequentially. First, the heavy chain PCR product and the vector TCAE 6 were digested with the restriction enzymes Sal I and Nhe I, the products extracted with phenol/chloroform, and passed through a SEPHADEX G-25 spin column. The PCR product was ligated to the cut vector overnight at 14° C. in the presence of T4 DNA ligase. Approximately 500 ng total DNA was ligated in a volume of 10 μl with an insert/vector molar ratio of 10:1. Ligated material was used to transform XL-1 Blue competent cells (Stratagene) and the transformed cells plated onto LB agar plates containing 50 μg/ml ampicillin. Colonies of ampicillin resistant bacteria were picked and grown as 5 ml minicultures. Plasmid DNA was extracted from each of these cultures by a standard alkaline lysis method cut with the restriction enzymes Sal I and Nhe I and the products run on a 1.2% agarose gel. Plasmids with inserts of approximately 450 bp were used as templates for the subsequent cloning of light chain variable regions. The products of the light chain PCR reaction as well the plasmid containing the heavy chain insert were cut with the restriction enzymes Bgl II and Avr II and ligated together. Plasmid minicultures were screened by cutting with Bgl II and Avr II. Digests giving an insert of approximately 400–450 bp were scored positive. Plasmids containing both Sal I/Nhe I and Bgl II/Avr II inserts were grown up in larger quantities for DNA sequencing.

The tandem chimeric antibody expression vectors TCAE 5.2 and TCAE 6 were derived from the vector CLDN, which itself is a derivative of the vector RLDN10b (253 *Science* 77–79.1991). RLDN10b in turn is a derivative of the expression vector TND (7 *DNA* 651–661, 1988)

RLDN10b differs from the vector TND in the following ways. The dihydrofolate reductase (DHFR) transcriptional cassette (promoter, cDNA, and polyadenylation region) was placed inbetween the tissue plasminogen activator cassette (t-PA expression cassette) and the neomycin phosphotransferase (NEO) cassette so that all three cassettes are in tandem and in the same transcriptional orientation. In addition, the DHFR gene promoter in CLDN has been replaced by the mouse beta globin major promoter (3 *Mol. Cell Biol.* 1246–54, 1983) and the t-PA cDNA replaced by a polylinker. All three eukaryotic transcriptional cassettes (Expression, DHFR, NEO) can be separated from the bacterial plasmid DNA (pUC9 derivative) by digestion with the restriction endonuclease NotI.

CLDN differs from RLDN10b because the Rous LTR in front of the polylinker has been replaced by the human cytomegalovirus immediate early gene promoter enhancer (41 *Cell*, 521, 1985).

The expression vectors TCAE 5.2 and TCAE 6 differ from CLDN in that:

1) They contain four transcriptional cassettes (instead of three), in tandem order:

(a) A human immunoglobulin light chain constant region derived via amplification of cDNA by a polymerase chain reaction. In TCAE 5.2 this is the human immunoglobulin light chain kappa constant region (Kabat numbering amino acids 108-214, allotype Km3), and in TCAE 6 the human immunoglobulin light chain lambda constant region (Kabat numbering amino acids 108-215, genotype Oz minus, Mcg minus, Ke minus allotype)

(b) A human immunoglobulin heavy chain constant region; in both constructs the human immunoglobulin heavy chain was a gamma 1 constant region (Kabat numbering amino acids 114-478 allotype Gm1a, Gm1z), which was derived via amplification of cDNA by a polymerase chain reaction.

(c) DHFR; containing its own eukaryotic promoter and polyadenylation region.

(d) NEO; also containing its own eukaryotic promoter and polyadenylation region.

3) The human immunoglobulin light and heavy chain cassettes contain synthetic signal sequences for secretion of the immunoglobulin chains 4) The human immunoglobulin light and heavy chain cassettes contain specific DNA linkers which allow for insertion of light and heavy immunoglobulin variable regions which maintain the translational reading frame and do not alter the amino acids normally found in immunoglobulin chains. The incorporation of the changes described, led to the construction of the vectors TCAE 5.2 and TCAE 6. The cloning of the immunoglobulin light and heavy variable region genes, from the anti-CD4 heterohybridoma cell line E9.1, into TCAE 6 led to the construct which is deposited in the ATCC. The construct, which has been deposited, contains the cynomolgus monkey immunoglobulin heavy chain variable region and cynomolgus monkey immunoglobulin light chain variable region, whose sequences are shown in FIGS. 13 and 14 respectively (SEQ ID NOS: 107–110), cloned from the anti-CD4 hybridoma cell line E9.1. The heavy chain constant region is of human origin of the gamma 1 isotype and Gm1a, Gm1z allotype. The lambda light chain constant region is also of human origin, of the Oz minus, mcg minus genotype and Ke minus allotype. The immunoglobulin genes are cloned into the mammalian expression vector TCAE 6, shown in FIG. 6, which, when electroporated into the mammalian cell line CHO produced a monkey/human anti-CD4 chimeric antibody. The DNA construct described herein, has been used to transform the bacterial strain XL-1 Blue, selected in the antibiotic ampicillin and deposited as a bacterial cell suspension in sterile LB medium containing 15% glycerol.

Another useful expression system is one in which the gene encoding a selective marker is modified to enhance yield of recombinant systems encoding a desired sequence. For example, translation initiation impairment of a dominant selectable marker results in fewer drug resistant colonies compared to a non-impaired vector, but each individual colony expresses significantly higher levels of colinked gene product than in the unimpaired vector. For example, translation initiation is the first step in protein synthesis. The translation initiation site of the neomycin phosphotransferase gene (G418 resistance gene) was changed from a consensus Kozak (sequence—ccAccATGG) to a poor Kozak (sequence—ccTccATGC). Translational initiation impairment of the G418 resistance gene resulted in: 1) a significant (5 fold) reduction in the number of G418 resistant colonies obtained from a same amount of plasmid DNA transfected per cell, and 2) a significant increase in the amount of colinked product gene expressed in each clone. In the clones containing the consensus Kozak 73% of the colonies screened produced less than 25 ng/ml, with only 3% producing greater than 100 ng/ml. For clones with the altered, poorer Kozak, 8% of the colonies screened produced less than 25 ng/ml, compared with 63% of colonies producing greater than 100 ng/ml. Specifically, referring to FIG. 16 (where TCAE 5.2 has a consensus Kozak, and TCAE 12 has a poorer Kozak), 258 colonies were derived from 2 electroporations of 25 µg of DNA which contains a neomycin phosphotransferase gene with a consensus (unchanged) translation start site. 201 of these colonies (78%) did not express any detectable gene product (i.e., <25 ng/ml of chimeric immunoglobulin), and only 8 colonies (3%) expressed more than 100 ng/ml. 98 colonies were derived from 6 electroporations of 25 µg of DNA which contains the neomycin phosphotransferase gene with an altered translation start site. 63% of these colonies were expressing more than 100 ng/ml, and only 8% of these colonies expressed less than 25 ng/ml.

DNA Sequencing

Plasmid DNA was prepared from 100 ml cultures. It was further purified by precipitating (1 volume) with a mixture of 2.5M sodium chloride and 20% polyethylene glycol (6 volumes) on ice for 15 minutes. After centrifugation at 10,000×g for 20 minutes, the pellet was washed with 70% ethanol, recentrifuged and dried in a Speedivac (Savant). The pellet of DNA was resuspended in deionized water at a concentration of 150–250 µg/ml. Sequencing was carried out on 5 µg of double stranded DNA using the technique of Sanger. Sequencing primers which were homologous to sequences within the expression vector upstream and downstream of either the light chain or heavy chain inserts were used. The inserts were sequenced in both 5' to 3' and 3' to 5' directions. Two clones of anti-CD4 light chain and two clones of anti-CD4 heavy chain each generated from separate PCR reactions were sequenced in parallel in order to determine whether any nucleotide changes had been introduced during the PCR reaction. Both of the chosen heavy chain and both light chain clones were found to be identical over their entire length, confirming that no errors had been introduced during the amplification process. The sequence of the anti-CD4 heavy and light chains are shown in FIGS. 13 and 14 and SEQ ID NOS: 107–110.

Expression of Monkey/Human Chimeric Anti-CD4

The expression vector TCAE 5.2 and TCAE 6 are not only able to be used for stable integrated expression into the cell lines Sp2/0 and CHO but, because it includes the SV40 origin, is also able to be expressed transiently in the cell line COS. COS cell expression was performed as follows: COS cells were seeded one day before the transfection so that they would be 50–70% confluent the following day. Culture medium was removed and the cells washed twice with Transfection Buffer (TB—140 mM NaCl, 25 mM Tris, 5 mM KCl, 0.5 mM $Na_2HPO_4$, 1 mM $MgCl_2$, 1 mM $CaCl_2$). 30 µg of cesium chloride purified TCAE 6 plasmid containing the anti-CD4 monkey/human chimeric heavy and light immunoglobulin chains were mixed with 3 ml of DEAE dextran per dish (1 mg/ml in TB). The DNA was allowed to incubate with the cells for 1 hour at 37° C. DNA solution was removed and replaced with 3 ml of 20% glycerol for 1.5–2.5 minutes, after which the cells were twice washed with TB. Cells were incubated in 5 ml of fresh medium containing 100 uM chloroquine for 3–5 hours at 37° C., after which they were washed twice with medium and incubated with normal DMEM for 72 hours. Supernatant (100 µl) from the transfected COS cells was assayed at various dilutions for the presence of antibody by an ELISA-based technique. Goat anti-human lambda was used to coat 96 well assay plates and a peroxidase-labeled goat anti-human IgG as the detection antibody, under standard ELISA conditions. COS cells were found to produce between 10 and 40 ng/ml of monkey/human chimeric antibody. Larger volumes of supernatant were concentrated 10 fold and used in a direct binding RIA to CD4 positive supT1 cells. The parental whole monkey antibody and an irrelevant human immunoglobulin were used as a positive and negative controls respectively (FIG. 11). Furthermore, the monkey anti-CD4 and the monkey/human chimeric anti-CD4 were used to inhibit the binding of a high affinity mouse anti-CD4 (1F3) antibody (FIG. 12). It can be seen that the monkey/human recombinant antibody (ATCC No. 69030) not only binds to CD4 positive cells but is able to inhibit the binding of 1F3 to CD4 positive cells in approximately the same concentrations of wholly monkey antibody or 1F3 itself.

The following is an example of the methods and antibodies of this invention.

EXAMPLE 4

Generation of Monkey Antibodies Against Human Lymphocyte Antigens

An adult cynomolgus monkey (White Sands New Mexico Primate Center) was immunized intramuscularly, at multiple sites, with $5 \times 10^8$ whole CD54 positive human lymphocytes. Cells used were alternately, SB cells (human B lymphoid line) and activated peripheral human lymphocytes, activated by pre-incubation with a mixture of pokeweed mitogen (2.5 mg/ml), phorbol monoacetate (40 nM) and phytohemagglutinin (4 mg/well) with the inclusion of a standard adjuvant. Immunization was repeated every 2–3 weeks over a period of 8 months. Sera from the immunized animals were screened at various times by inhibition of binding of a murine antibody, 84H10, known to bind to ICAM-1. A saturating amount of 84H10 was bound to chinese hamster ovary cells (CHO), previously transfected with an expression vector containing human CD54 c-DNA and selected for high expression of cell surface CD54, together with increasing dilutions of monkey serum. The inhibition of 84H10 binding is shown in FIG. 15.

Other murine monoclonal antibodies which recognize other human lymphocyte antigens were tested by inhibition using monkey sera obtained by the same immunization methods.

Use

Antibodies produced in the manner described above, or by equivalent techniques, can be purified by a combination of affinity and size exclusion chromatography for characterization in functional biological assays. These assays include determination of specificity and binding affinity as well as effector function associated with the expressed isotype, e.g., ADCC, or complement fixation. Such antibodies may be used as passive or active therapeutic agents against a number of human diseases, including B cell lymphoma, infectious diseases including AIDS, autoimmune and inflammatory diseases, and transplantation. The antibodies can be used either in their native form, or as part of an antibody/chelate, antibody/drug or antibody/toxin complex. Additionally, whole antibodies or antibody fragments ($Fab_2$, Fab, Fv) may be used as imaging reagents or as potential vaccines or immunogens in active immunotherapy for the generation of anti-idiotypic responses.

The amount of antibody useful to produce a therapeutic effect can be determined by standard techniques well known to those of ordinary skill in the art. The antibodies will generally be provided by standard technique within a pharmaceutically acceptable buffer, and may be administered by any desired route. Because of the efficacy of the presently claimed antibodies and their tolerance by humans it is possible to administer these antibodies repetitively in order to combat various diseases or disease states within a human.

The anti-CD4 recombinant antibodies (or fragments thereof) of this invention are also useful for inducing immunosuppression, i.e., inducing a suppression of a human's or animal's immune system. This invention therefore relates to a method of prophylactically or therapeutically inducing immunosuppression in a human or other animal in need thereof by administering an effective, non-toxic amount of such an antibody of this invention to such human or other animal.

The ability of the compounds of this invention to induce immunosuppression may be demonstrated in standard tests used for this purpose, for example, a mixed lymphocyte reaction test or a test measuring inhibition of T-cell proliferation measured by thymidine uptake.

The fact that the antibodies of this invention have utility in inducing immunosuppression means that they are useful in the treatment or prevention of resistance to or rejection of transplanted organs or tissues (e.g., kidney, heart, lung, bone marrow, skin, cornea, etc.); the treatment or prevention of autoimmune, inflammatory, proliferative and hyperproliferative diseases, and of cutaneous manifestations of immunologically medicated diseases (e.g., rheumatoid arthritis, lupus erythematosus, systemic lupus erythematosus, Hashimotos thyroiditis, multiple sclerosis, myasthenia gravis, type 1 diabetes, uveitis, nephrotic syndrome, psoriasis, atopical dermatitis, contact dermatitis and further eczematous dermatitides, seborrheic dermatitis, Lichen planus, Pemplugus, bullous pemphigus, Epidermolysis bullosa, urticaria, angioedemas, vasculitides, erythema, cutaneous eosinophilias, Alopecia areata, etc.); the treatment of reversible obstructive airways disease, intestinal inflammations and allergies (e.g., Coeliac disease, proctitis, eosinophilia gastroenteritis, mastocytosis, Crohn's disease and ulcerative colitis) and food-related allergies (e.g., migraine, rhinitis and eczema).

One skilled in the art would be able, by routine experimentation, to determine what an effective, non-toxic amount of antibody would be for the purpose of inducing immunosuppression. Generally, however, an effective dosage will be in the range of about 0.05 to 100 milligrams per kilogram body weight per day.

The antibodies (or fragments thereof) of this invention should also be useful for treating tumors in a mammal. More specifically, they should be useful for reducing tumor size, inhibiting tumor growth and/or prolonging the survival time of tumor-bearing animals. Accordingly, this invention also relates to a method of treating tumors in a human or other animal by administering to such human or animal an effective, non-toxic amount of an antibody. One skilled in the art would be able, by routine experimentation, to determine what an effective, non-toxic amount of antibody would be for the purpose of treating carcinogenic tumors. Generally, however, an effective dosage is expected to be in the range of about 0.05 to 100 milligrams per kilogram body weight per day.

The antibodies of the invention may be administered to a human or other animal in accordance with the aforementioned methods of treatment in an amount sufficient to produce such effect to a therapeutic or prophylactic degree. Such antibodies of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The route of administration of the antibody (or fragment thereof) of the invention may be oral, parenteral, by inhalation or topical. The term parenteral as used herein includes intravenous, intramuscular, subcutaneous, rectal, vaginal or intraperitoneal administration. The subcutaneous and intramuscular forms of parenteral administration are generally preferred.

The daily parenteral and oral dosage regimens for employing compounds of the invention to prophylactically or therapeutically induce immunosuppression, or to therapeutically treat carcinogenic tumors will generally be in the range of about 0.05 to 100, but preferably about 0.5 to 10, milligrams per kilogram body weight per day.

The antibody of the invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 10 to 100 milligrams.

The antibody of the invention may also be administered topically. By topical administration is meant non-systemic administration and includes the application of an antibody (or fragment thereof) compound of the invention externally to the epidermis, to the buccal cavity and instillation of such an antibody into the ear, eye and nose, and where it does not significantly enter the blood stream. By systemic administration is meant oral, intravenous, intraperitoneal and intramuscular administration. The amount of an antibody required for therapeutic or prophylactic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

Formulations

While it is possible for an antibody or fragment thereof to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation.

The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 90°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

It will be recognized by one of skill in the art that the optimal quantity and spacing of individual dosages of an antibody or fragment thereof of the invention will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of an antibody or fragment thereof of the invention given per day for a defined number of days, can be ascertained by those skilled in the art using conventional course of treatment determination tests.

Without further elaboration, it is believed that one skilled in the art can, using the preceding description, utilize the present invention to its fullest extent. The following are, therefore, to be construed as merely illustrative examples and not a limitation of the scope of the present invention in any way.

Capsule Composition

A pharmaceutical composition of this invention in the form of a capsule is prepared by filling a standard two-piece hard gelatin capsule with 50 mg. of an antibody or fragment thereof of the invention, in powdered form, 100 mg. of lactose, 32 mg. of talc and 8 mg. of magnesium stearate.

Injectable Parenteral Composition

A pharmaceutical composition of this invention in a form suitable for administration by injection is prepared by stirring 1.5% by weight of an antibody or fragment thereof of the invention in 10% by volume propylene glycol and water. The solution is sterilized by filtration.

Ointment Composition

Antibody or fragment thereof of the invention 1.0 g.

White soft paraffin to 100.0 g.

The antibody or fragment thereof of the invention is dispersed in a small volume of the vehicle to produce a smooth, homogeneous product. Collapsible metal tubes are then filled with the dispersion.

Topical Cream Composition

Antibody or fragment thereof of the invention 1.0 g.

Polawax GP 200 20.0 g.

Lanolin Anhydrous 2.0 g.

White Beeswax 2.5 g.

Methyl hydroxybenzoate 0.1 g.

Distilled Water to 100.0 g.

The polawax, beeswax and lanolin are heated together at 60° C. A solution of methyl hydroxybenzoate is added and homogenization is achieved using high speed stirring. The temperature is then allowed to fall to 50° C. The antibody or fragment thereof of the invention is then added and dispersed throughout, and the composition is allowed to cool with slow speed stirring.

Topical Lotion Composition

Antibody or fragment thereof of the invention 1.0 g.

Sorbitan Monolaurate 0.6 g.

Polysorbate 20 0.6 g.

Cetostearyl Alcohol 1.2 g.

Glycerin 6.0 g.

Methyl Hydroxybenzoate 0.2 g.

Purified Water B.P. to 100.00 ml. (B.P.=British Pharmacopeia)

The methyl hydroxybenzoate and glycerin are dissolved in 70 ml. of the water at 75° C. The sorbitan monolaurate, polysorbate 20 and cetostearyl alcohol are melted together at 75° C. and added to the aqueous solution. The resulting emulsion is homogenized, allowed to cool with continuous stirring and the antibody or fragment thereof of the invention is added as a suspension in the remaining water. The whole suspension is stirred until homogenized.

Eye Drop Composition

Antibody or fragment thereof of the invention 0.5 g.

Methyl Hydroxybenzoate 0.01 g.

Propyl Hydroxybenzoate 0.04 g.

Purified Water B.P. to 100.00 ml.

The methyl and propyl hydroxybenzoates are dissolved in 70 ml. purified water at 75° C. and the resulting solution is allowed to cool. The antibody or fragment thereof of the invention is then added, and the solution is sterilized by filtration through a membrane filter (0.022 μm pore size), and packed aseptically into suitable sterile containers.

Composition for Administration by Inhalation

For an aerosol container with a capacity of 15–20 ml: mix 10 mg. of an antibody or fragment thereof of the invention with 0.2–0.5% of a lubricating agent, such as polysorbate 85 or oleic acid, and disperse such mixture in a propellant, such as freon, preferably in a combination of (1,2 dichlorotetrafluoroethane) and difluorochloromethane and put into an appropriate aerosol container adapted for either intranasal or oral inhalation administration.

Composition for Adminstration by Inhalation

For an aerosol container with a capacity of 15–20 ml: dissolve 10 mg. of an antibody or fragment thereof of the invention in ethanol (6–8 ml.), add 0.1–0.2% of a lubricating agent, such as polysorbate 85 or oleic acid; and disperse such in a propellant, such as freon, preferably in combination of (1.2 dichlorotetrafluoroethane) and difluorochloromethane, and put into an appropriate aerosol container adapted for either intranasal or oral inhalation administration.

The antibodies and pharmaceutical compositions of the invention are particularly useful for parenteral administration, i.e., subcutaneously, intramuscularly or intravenously. The compositions for parenteral administration will commonly comprise a solution of an antibody or fragment thereof of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well-known sterilization techniques. The compositions may contain pharmaceutically acceptable auxiliary substances as required to approximate physiological conditions such as pH adjusting and buffering agents, etc. The concentration of the antibody or fragment thereof of the invention in such pharmaceutical formulation can vary widely, i.e., from less than about 0.5%, usually at or at least about 1% to as much as 15 or 20% by weight, and will be selected primarily based on fluid volumes, viscosities, etc., according to the particular mode of administration selected.

Thus, a pharmaceutical composition of the invention for intramuscular injection could be prepared to contain 1 mL sterile buffered water, and 50 mg. of an antibody or fragment thereof of the invention. Similarly, a pharmaceutical composition of the invention for intravenous infusion could be made up to contain 250 ml. of sterile Ringer's solution, and 150 mg. of an antibody or fragment thereof of the invention. Actual methods for preparing parenterally administrable compositions are well-known or will be apparent to those skilled in the art, and are described in more detail in, for example, Remington's Pharmaceutical Science, 15th ed., Mack Publishing Company, Easton, Pa., hereby incorporated by reference herein.

The antibodies (or fragments thereof) of the invention can be lyophilized for storage and reconstituted in a suitable carrier prior to use. This technique has been shown to be effective with conventional immune globulins and art-known lyophilization and reconstitution techniques can be employed.

Depending on the intended result, the pharmaceutical composition of the invention can be administered for prophylactic and/or therapeutic treatments. In therapeutic application, compositions are administered to a patient already suffering from a disease, in an amount sufficient to cure or at least partially arrest the disease and its complications. In prophylactic applications, compositions containing the present antibodies or a cocktail thereof are administered to a patient not already in a disease state to enhance the patient's resistance.

Single or multiple administrations of the pharmaceutical compositions can be carried out with dose levels and pattern being selected by the treating physician. In any event, the pharmaceutical composition of the invention should provide a quantity of the altered antibodies (or fragments thereof) of the invention sufficient to effectively treat the patient.

It should also be noted that the antibodies of this invention may be used for the design and synthesis of either peptide or non-peptide compounds (mimetics) which would be useful in the same therapy as the antibody. See, e.g., Saragovi et al., Science, 253, 792–795 (1991).

Deposit

Strain E. coli XL-1 Blue TCAE-6 plasmid has been deposited with the ATCC and assigned number 69030. This deposit was made on Jul. 9, 1992.

Applicants' and their assignees acknowledge their responsibility to replace these cultures should they die before the end of the term of a patent issued hereon, 5 years after the last request for a culture, or 30 years, whichever is the longer, and its responsibility to notify the depository of the issuance of such a patent, at which time the deposit will be made irrevocably available to the public. Until that time the deposit will be made available to the Commissioner of Patents under the terms of 37 C.F.R. Section 1-14 and 35 U.S.C. Section 112.

Other embodiments are within the following claims.

We claim:

1. An improved method for treatment of a subject which comprises the administration of an antibody to a subject in need for such treatment, wherein the improvement comprises the administration of a therapeutically or prophylactically effective amount of an antibody which comprises an Old World monkey variable region which binds to an antigen, or antigen-binding portion thereof, and a human constant domain.

2. The method of claim 1, wherein said antibody binds to a tumor antigen and the treatment comprises treatment of cancer.

3. The method of claim 1, wherein said antibody binds to an antigen involved in autoimmune response and the treatment comprises treatment of an autoimmune disorder.

4. The method of claim 1, wherein said antibody binds to an antigen wherein said antigen is a receptor expressed by a cell of the treated subject.

5. The method of claim 1, wherein said antigen is selected from the group consisting of CD58, VCAM, VLA4, CD2, LFA3, ELAM, LAM, CD25, CD4, CD19, CD20, CD23, CD41, CD44, CD54, TNFα, TNFβ, Tn antigen, IL-1, IL-8, human T-cell receptor, CD3, CD28, CD8, CD18, CD11a, CD11b, CD11c, CD5a, CD45, neu oncogene product, MDR-1, TGFα, TGFα-receptor, PDGF, and CD71.

6. The method of claim 1, wherein said antigen-binding portion comprises one or more CDR regions of an Old World monkey variable region.

7. The method of claim 1, wherein said antibody comprises an entire variable region of an Old World monkey antibody.

8. The method of claim 1, wherein the treatment comprises treatment of a disease selected from the group consisting of rheumatoid arthritis, eczema, and immunomodulated diseases, and the antigen bound by the antibody is CD4.

9. The method of claim 8, wherein the antibody comprises the variable domain sequence as set forth in Sequence ID NO. 108 or Sequence ID NO. 110.

10. The method of claim 9, wherein the therapy is for the treatment of rheumatoid arthritis.

* * * * *

SEQUENCE LISTING ( 1 ) GENERAL INFORMATION:

( i i i ) NUMBER OF SEQUENCES: 114

( 2 ) INFORMATION FOR SEQ ID NO:1:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Monkey ( v i i i ) POSITION IN GENOME:
        ( A ) CHROMOSOME/SEGMENT: Ig heavy chain leader ( x i ) SEQUENCE DESCRIPTION: SEQ ID NO:1:

```
ATGGACTGGA CCTGGAGGCT CCTCTTTNNN GTGGTGGCAG CAGCTACAGG TGCCAAGTCC        60
```

( 2 ) INFORMATION FOR SEQ ID NO:2:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Monkey ( v i i i ) POSITION IN GENOME:
        ( A ) CHROMOSOME/SEGMENT: Ig heavy chain leader ( x i ) SEQUENCE DESCRIPTION: SEQ ID NO:2:

```
TGTTCCACGC TCCTGNNNCT GCTGACCGTC CCGTCCTGGG TTTTGTCC                     48
```

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Monkey ( v i i i ) POSITION IN GENOME:
        ( A ) CHROMOSOME/SEGMENT: Ig heavy chain leader ( x i ) SEQUENCE DESCRIPTION: SEQ ID NO:3:

```
TTGNNNCTAC TGACCGTCCC GTCCTGGGTC TTGTCC                                  36
```

( 2 ) INFORMATION FOR SEQ ID NO:4:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Monkey ( v i i i ) POSITION IN GENOME:
        ( A ) CHROMOSOME/SEGMENT: Ig heavy chain leader ( x i ) SEQUENCE DESCRIPTION: SEQ ID NO:4:

TGTTCCACAC TCTTGNNNCT ACTGACCGTC CCGTCCTGGG TCTTGTCC 48

( 2 ) INFORMATION FOR SEQ ID NO:5:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Monkey ( v i i i ) POSITION IN GENOME:
        ( A ) CHROMOSOME/SEGMENT: Ig heavy chain leader ( x i ) SEQUENCE DESCRIPTION: SEQ ID NO:5:

ATGGAGTTTG GGCTGAGCTG GGTTTTCNNN CTTGTTGCTA TTTTCAAAGG TGTCCAGTGT 60

( 2 ) INFORMATION FOR SEQ ID NO:6:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Monkey ( v i i i ) POSITION IN GENOME:
        ( A ) CHROMOSOME/SEGMENT: Ig heavy chain leader ( x i ) SEQUENCE DESCRIPTION: SEQ ID NO:6:

ATGGAGTTTG GGCTGAGCTG GGTTTTCNNN CTTGTTGCTC TTTTAAAGGG CGTCCAGTGT 60

( 2 ) INFORMATION FOR SEQ ID NO:7:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Monkey ( v i i i ) POSITION IN GENOME:
        ( A ) CHROMOSOME/SEGMENT: Ig heavy chain leader ( x i ) SEQUENCE DESCRIPTION: SEQ ID NO:7:

ATGGAGTTTG GGCTGAGCTG GGTTTTCNNN CTTGTTGCTA TTTTAAGAGG CGTCCAGTGT 60

( 2 ) INFORMATION FOR SEQ ID NO:8:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Monkey (v i i i) POSITION IN GENOME:
        (A) CHROMOSOME/SEGMENT: Ig heavy chain leader (x i) SEQUENCE DESCRIPTION: SEQ ID NO:8:

ATGAAACACC TGTGGTTCTT CCTCCTCNNN CTGGTGGCGG CTCCCAGATG GGTCCTGTCC    60

(2) INFORMATION FOR SEQ ID NO:9:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Monkey (v i i i) POSITION IN GENOME:
        (A) CHROMOSOME/SEGMENT: Ig heavy chain leader (x i) SEQUENCE DESCRIPTION: SEQ ID NO:9:

ATGAAACACC TGTGGTTCTT CCTCCTCNNN CTGCTGGCAG CTCCCAGATG GGTCCTGTCC    60

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Monkey (v i i i) POSITION IN GENOME:
        (A) CHROMOSOME/SEGMENT: Ig heavy chain leader (x i) SEQUENCE DESCRIPTION: SEQ ID NO:10:

TGGCTGTTCT CCAAGGAGTC TGTTCC    26

(2) INFORMATION FOR SEQ ID NO:11:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (i i) MOLECULE TYPE: cDNA (v i) ORIGINAL SOURCE:
        (A) ORGANISM: Homo sapiens (v i i i) POSITION IN GENOME:
        (A) CHROMOSOME/SEGMENT: Ig heavy chain leader (x i) SEQUENCE DESCRIPTION: SEQ ID NO:11:

ATGGACTGGA CCTGGAGGGT CTTCTGCNNN TTGCTGGCTG TAGCACCAGG TGCCCACTCC    60

(2) INFORMATION FOR SEQ ID NO:12:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (i i) MOLECULE TYPE: cDNA 5,750,105

33

34

-continued ( v i ) ORIGINAL SOURCE:
    ( A ) ORGANISM: Homo sapiens ( v i i i ) POSITION IN GENOME:
    ( A ) CHROMOSOME/SEGMENT: Ig heavy chain leader ( x i ) SEQUENCE DESCRIPTION: SEQ ID NO:12:

ATGGACTGGA CCTGGNNNAT CCTCTTCNNN TTGGTGGCAG CAGCCACGCG AGTCCACTCC    60

( 2 ) INFORMATION FOR SEQ ID NO:13:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( v i i i ) POSITION IN GENOME:
    ( A ) CHROMOSOME/SEGMENT: Ig heavy chain leader ( x i ) SEQUENCE DESCRIPTION: SEQ ID NO:13:

ATGGACATAC TTTGTTCCAC GCTCCTGNNN CTACTGACTG TCCCGTCCTG GGTCTTATCC    60

( 2 ) INFORMATION FOR SEQ ID NO:14:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( v i i i ) POSITION IN GENOME:
    ( A ) CHROMOSOME/SEGMENT: Ig heavy chain leader ( x i ) SEQUENCE DESCRIPTION: SEQ ID NO:14:

ATGGAGTTTG GGCTGAGCTG GCTTTTTNNN CTTGTGGCTA TTTTAAAAGG TGTCCAGTGT    60

( 2 ) INFORMATION FOR SEQ ID NO:15:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( v i i i ) POSITION IN GENOME:
    ( A ) CHROMOSOME/SEGMENT: Ig heavy chain leader ( x i ) SEQUENCE DESCRIPTION: SEQ ID NO:15:

ATGGAGTTTG GGCTGAGCTG GGTTTTCNNN CTTGTTGCTA TTTTAAAAGG TGTCCAGTGT    60

( 2 ) INFORMATION FOR SEQ ID NO:16:

( i ) SEQUENCE CHARACTERISTICS:
    ( A ) LENGTH: 60 base pairs
    ( B ) TYPE: nucleic acid ( C ) STRANDEDNESS: single
( D ) TOPOLOGY: linear ( i i ) MOLECULE TYPE: cDNA ( v i ) ORIGINAL SOURCE:
    ( A ) ORGANISM: Homo sapiens ( v i i i ) POSITION IN GENOME:
    ( A ) CHROMOSOME/SEGMENT: Ig heavy chain leader ( x i ) SEQUENCE DESCRIPTION: SEQ ID NO:16:

ATGGAGCTTG GGCTGACCTG GGTTTTCNNN CTTGTTGCTC TTTTAAAAGG TGTCCAGTGT    60

( 2 ) INFORMATION FOR SEQ ID NO:17:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i i ) POSITION IN GENOME:
        ( A ) CHROMOSOME/SEGMENT: Ig heavy chain leader ( x i ) SEQUENCE DESCRIPTION: SEQ ID NO:17:

ATGGAGCTTG GGCTGACCTG GGTTTTCNNN CTTGTTGCTC TTTTAAAAGG TGTCCAGTGT    60

( 2 ) INFORMATION FOR SEQ ID NO:18:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i i ) POSITION IN GENOME:
        ( A ) CHROMOSOME/SEGMENT: Ig heavy chain leader ( x i ) SEQUENCE DESCRIPTION: SEQ ID NO:18:

ATGAAACACC TGTGGTTCCT CCTCCTCTGG TGTCAGCTCC CAGATGTGAG GGTCCTGTCC    60

( 2 ) INFORMATION FOR SEQ ID NO:19:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( v i i i ) POSITION IN GENOME:
        ( A ) CHROMOSOME/SEGMENT: Ig heavy chain leader ( x i ) SEQUENCE DESCRIPTION: SEQ ID NO:19:

ATGAAACANC TGTGGTTCTT CCTTCTCNNN CTGGTGGCAG CTCCCAGATG GGTCCTGTCC    60

( 2 ) INFORMATION FOR SEQ ID NO:20:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: cDNA ( i v ) ANTI-SENSE: NO ( v i ) ORIGINAL SOURCE:
    ( A ) ORGANISM: Homo sapiens or Monkey ( v i i i ) POSITION IN GENOME:
    ( A ) CHROMOSOME/SEGMENT: heavy chain primers with SalI site ( x i ) SEQUENCE DESCRIPTION: SEQ ID NO:20:

ACTAAGTCGA CATGGACTGG ACCTGG 26

( 2 ) INFORMATION FOR SEQ ID NO:21:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: cDNA ( i v ) ANTI-SENSE: NO ( v i ) ORIGINAL SOURCE:
    ( A ) ORGANISM: Homo sapiens or Monkey ( v i i i ) POSITION IN GENOME:
    ( A ) CHROMOSOME/SEGMENT: heavy chain primers with SalI site ( x i ) SEQUENCE DESCRIPTION: SEQ ID NO:21:

ACTAAGTCGA CATGGACATA CTTTGTTCCA C 31

( 2 ) INFORMATION FOR SEQ ID NO:22:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: cDNA ( i v ) ANTI-SENSE: NO ( v i ) ORIGINAL SOURCE:
    ( A ) ORGANISM: Homo sapiens or Monkey ( v i i i ) POSITION IN GENOME:
    ( A ) CHROMOSOME/SEGMENT: heavy chain primer with SalI site ( x i ) SEQUENCE DESCRIPTION: SEQ ID NO:22:

ACTAAGTCGA CATGGAGTTT GGGCTGAGC 29

( 2 ) INFORMATION FOR SEQ ID NO:23:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: cDNA ( i v ) ANTI-SENSE: NO (  v i  ) ORIGINAL SOURCE:
    ( A ) ORGANISM: Homo sapiens or Monkey (  v i i i  ) POSITION IN GENOME:
    ( A ) CHROMOSOME/SEGMENT: heavy chain primer with SalI site (  x i  ) SEQUENCE DESCRIPTION: SEQ ID NO:23:

ACTAAGTCGA CATGAAACAC CTGTGGTTCT T  31

( 2 ) INFORMATION FOR SEQ ID NO:24:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: NO ( v i ) ORIGINAL SOURCE:
        ( A ) ORGANISM: Homo sapiens or Monkey ( v i i i ) POSITION IN GENOME:
        ( A ) CHROMOSOME/SEGMENT: heavy chain primer with SalI site ( x i ) SEQUENCE DESCRIPTION: SEQ ID NO:24:

ACTAAGTCGA CATGGGGTCA ACCGCCATCC T  31

( 2 ) INFORMATION FOR SEQ ID NO:25:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: NO ( v i ) ORIGINAL SOURCE:
        ( A ) ORGANISM: Homo sapiens or Monkey ( v i i i ) POSITION IN GENOME:
        ( A ) CHROMOSOME/SEGMENT: heavy chain primer with SalI site ( x i ) SEQUENCE DESCRIPTION: SEQ ID NO:25:

ACTAAGTCGA CATGTCTGTC TCCTTCCTCA T  31

( 2 ) INFORMATION FOR SEQ ID NO:26:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens or Monkey ( v i i i ) POSITION IN GENOME:
        ( A ) CHROMOSOME/SEGMENT: heavy chain primer with MluI site ( x i ) SEQUENCE DESCRIPTION: SEQ ID NO:26:

GGCAGCAGC Y ACGCGTGCCC ACTCCGAGGT  30

( 2 ) INFORMATION FOR SEQ ID NO:27:

( i ) SEQUENCE CHARACTERISTICS:
   ( A ) LENGTH: 30 base pairs
   ( B ) TYPE: nucleic acid
   ( C ) STRANDEDNESS: single
   ( D ) TOPOLOGY: linear ( i i ) MOLECULE TYPE: cDNA ( v i ) ORIGINAL SOURCE:
   ( A ) ORGANISM: Homo sapiens or Monkey ( v i i i ) POSITION IN GENOME:
   ( A ) CHROMOSOME/SEGMENT: heavy chain primer with MluI site ( x i ) SEQUENCE DESCRIPTION: SEQ ID NO:27:

GACCGTCCCG ACGCGTGT Y T TGTCCCAGGT    30

( 2 ) INFORMATION FOR SEQ ID NO:28:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: cDNA ( v i ) ORIGINAL SOURCE:
      ( A ) ORGANISM: Homo sapiens or Monkey ( v i i i ) POSITION IN GENOME:
      ( A ) CHROMOSOME/SEGMENT: heavy chain primer with MluI site ( x i ) SEQUENCE DESCRIPTION: SEQ ID NO:28:

GCTATTTTCA CGCGTGTCCA GTGTGAG    27

( 2 ) INFORMATION FOR SEQ ID NO:29:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: cDNA ( v i ) ORIGINAL SOURCE:
      ( A ) ORGANISM: Homo sapiens or Monkey ( v i i i ) POSITION IN GENOME:
      ( A ) CHROMOSOME/SEGMENT: heavy chain primer with MluI site ( x i ) SEQUENCE DESCRIPTION: SEQ ID NO:29:

GCGGCTCCCA CGCGTGTCCT GTCCCAG    27

( 2 ) INFORMATION FOR SEQ ID NO:30:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: cDNA ( v i ) ORIGINAL SOURCE:
      ( A ) ORGANISM: Homo sapiens or Monkey ( v i i i ) POSITION IN GENOME:
      ( A ) CHROMOSOME/SEGMENT: heavy chain primer with MluI site ( x i ) SEQUENCE DESCRIPTION: SEQ ID NO:30:

GGCTGTTCTC ACGCGTGTCT GTGCCGAGGT    30

( 2 ) INFORMATION FOR SEQ ID NO:31:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens or Monkey ( v i i i ) POSITION IN GENOME:
        ( A ) CHROMOSOME/SEGMENT: primer with XhoI site ( x i ) SEQUENCE DESCRIPTION: SEQ ID NO:31:

CAGGTGCAGC TGCTCGAGTC TGG     23

( 2 ) INFORMATION FOR SEQ ID NO:32:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens or Monkey ( v i i i ) POSITION IN GENOME:
        ( A ) CHROMOSOME/SEGMENT: primer with XhoI site ( x i ) SEQUENCE DESCRIPTION: SEQ ID NO:32:

CAGGTCAACT TACTCGAGTC TGG     23

( 2 ) INFORMATION FOR SEQ ID NO:33:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens or Monkey ( v i i i ) POSITION IN GENOME:
        ( A ) CHROMOSOME/SEGMENT: primer with XhoI site ( x i ) SEQUENCE DESCRIPTION: SEQ ID NO:33:

GAGGTGCAGC TGCTCGAGTC TGG     23

( 2 ) INFORMATION FOR SEQ ID NO:34:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens or Monkey ( v i i i ) POSITION IN GENOME:
        ( A ) CHROMOSOME/SEGMENT: primer with XhoI site ( x i ) SEQUENCE DESCRIPTION: SEQ ID NO:34:

CAGGTGCAGC TGCTCGAGTC GGG   23

( 2 ) INFORMATION FOR SEQ ID NO:35:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens or Monkey ( v i i i ) POSITION IN GENOME:
        ( A ) CHROMOSOME/SEGMENT: primer with XhoI site ( x i ) SEQUENCE DESCRIPTION: SEQ ID NO:35:

CAGGTACAGC TGCTCGAGTC AGG   23

( 2 ) INFORMATION FOR SEQ ID NO:36:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: YES ( v i ) ORIGINAL SOURCE:
        ( A ) ORGANISM: Homo sapiens or Monkey ( v i i i ) POSITION IN GENOME:
        ( A ) CHROMOSOME/SEGMENT: heavy chain constant region primer wi
        NheI site ( x i ) SEQUENCE DESCRIPTION: SEQ ID NO:36:

GGCGGATGCG CTAGCTGAGG AGACGG   26

( 2 ) INFORMATION FOR SEQ ID NO:37:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: NO ( v i ) ORIGINAL SOURCE:
        ( A ) ORGANISM: Homo sapiens or Monkey ( v i i i ) POSITION IN GENOME:
        ( A ) CHROMOSOME/SEGMENT: kappa light chain primer with BglII si ( x i ) SEQUENCE DESCRIPTION: SEQ ID NO:37:

ATCACAGATC TCTCACCATG GTGTTGCAGA CCCAGGTC   38

( 2 ) INFORMATION FOR SEQ ID NO:38:

( i ) SEQUENCE CHARACTERISTICS:
        ( A ) LENGTH: 37 base pairs
        ( B ) TYPE: nucleic acid
        ( C ) STRANDEDNESS: single

```
            ( D ) TOPOLOGY: linear ( i i ) MOLECULE TYPE: cDNA ( i v ) ANTI-SENSE: NO ( v i ) ORIGINAL SOURCE:
            ( A ) ORGANISM: Homo sapiens or Monkey ( v i i i ) POSITION IN GENOME:
            ( A ) CHROMOSOME/SEGMENT: kappa light chain primer with BglII si ( x i ) SEQUENCE DESCRIPTION: SEQ ID NO:38:

ATCACAGATC  TCTCACCATG  GRGWCCCCWG  CKCAGCT                                        3 7

( 2 ) INFORMATION FOR SEQ ID NO:39:

( i ) SEQUENCE CHARACTERISTICS:
            ( A ) LENGTH: 41 base pairs
            ( B ) TYPE: nucleic acid
            ( C ) STRANDEDNESS: single
            ( D ) TOPOLOGY: linear ( i i ) MOLECULE TYPE: cDNA ( i v ) ANTI-SENSE: NO ( v i ) ORIGINAL SOURCE:
            ( A ) ORGANISM: Homo sapiens and Monkey ( v i i i ) POSITION IN GENOME:
            ( A ) CHROMOSOME/SEGMENT: kappa light chain primer with BglII si ( x i ) SEQUENCE DESCRIPTION: SEQ ID NO:39:

ATCACAGATC  TCTCACCATG  GACATGAGGG  TCCCCGCTCA  G                                  4 1

( 2 ) INFORMATION FOR SEQ ID NO:40:

( i ) SEQUENCE CHARACTERISTICS:
            ( A ) LENGTH: 41 base pairs
            ( B ) TYPE: nucleic acid
            ( C ) STRANDEDNESS: single
            ( D ) TOPOLOGY: linear ( i i ) MOLECULE TYPE: cDNA ( i v ) ANTI-SENSE: NO ( v i ) ORIGINAL SOURCE:
            ( A ) ORGANISM: Homo sapiens or Monkey ( v i i i ) POSITION IN GENOME:
            ( A ) CHROMOSOME/SEGMENT: kappa light chain primer with BglII si ( x i ) SEQUENCE DESCRIPTION: SEQ ID NO:40:

ATCACAGATC  TCTCACCATG  GACACVAGGG  CCCCCACTCA  G                                  4 1

( 2 ) INFORMATION FOR SEQ ID NO:41:

( i ) SEQUENCE CHARACTERISTICS:
            ( A ) LENGTH: 39 base pairs
            ( B ) TYPE: nucleic acid
            ( C ) STRANDEDNESS: single
            ( D ) TOPOLOGY: linear ( i i ) MOLECULE TYPE: cDNA ( i v ) ANTI-SENSE: NO ( v i ) ORIGINAL SOURCE:
            ( A ) ORGANISM: Homo sapiens or Monkey ( v i i i ) POSITION IN GENOME:
            ( A ) CHROMOSOME/SEGMENT: lambda light chain primer with BglII s
```

( x i ) SEQUENCE DESCRIPTION: SEQ ID NO:41:

ATCACAGATC TCTCACCATG GCCTGGGCTC TGCTGCTCC 39

( 2 ) INFORMATION FOR SEQ ID NO:42:

( i ) SEQUENCE CHARACTERISTICS:
      ( A ) LENGTH: 39 base pairs
      ( B ) TYPE: nucleic acid
      ( C ) STRANDEDNESS: single
      ( D ) TOPOLOGY: linear ( i i ) MOLECULE TYPE: cDNA ( i v ) ANTI-SENSE: NO ( v i ) ORIGINAL SOURCE:
      ( A ) ORGANISM: Homo sapiens or Monkey ( v i i i ) POSITION IN GENOME:
      ( A ) CHROMOSOME/SEGMENT: lambda light chain primer with BglII s ( x i ) SEQUENCE DESCRIPTION: SEQ ID NO:42:

ATCACAGATC TCTCACCATG GCCTGGGCTC CACTACTTC 39

( 2 ) INFORMATION FOR SEQ ID NO:43:

( i ) SEQUENCE CHARACTERISTICS:
      ( A ) LENGTH: 39 base pairs
      ( B ) TYPE: nucleic acid
      ( C ) STRANDEDNESS: single
      ( D ) TOPOLOGY: linear ( i i ) MOLECULE TYPE: cDNA ( i v ) ANTI-SENSE: NO ( v i ) ORIGINAL SOURCE:
      ( A ) ORGANISM: Homo sapiens or Monkey ( v i i i ) POSITION IN GENOME:
      ( A ) CHROMOSOME/SEGMENT: lambda light chain primer with BglII s ( x i ) SEQUENCE DESCRIPTION: SEQ ID NO:43:

ATCACAGATC TCTCACCATG ACCTGCTCCC CTCTCCTCC 39

( 2 ) INFORMATION FOR SEQ ID NO:44:

( i ) SEQUENCE CHARACTERISTICS:
      ( A ) LENGTH: 39 base pairs
      ( B ) TYPE: nucleic acid
      ( C ) STRANDEDNESS: single
      ( D ) TOPOLOGY: linear ( i i ) MOLECULE TYPE: cDNA ( i v ) ANTI-SENSE: NO ( v i ) ORIGINAL SOURCE:
      ( A ) ORGANISM: Homo sapiens or Monkey ( v i i i ) POSITION IN GENOME:
      ( A ) CHROMOSOME/SEGMENT: lambda light chain primer with BglII s ( x i ) SEQUENCE DESCRIPTION: SEQ ID NO:44:

ATCACAGATC TCTCACCATG GCCTGGACTC CTCTCTTTC 39

( 2 ) INFORMATION FOR SEQ ID NO:45:

( i ) SEQUENCE CHARACTERISTICS:
      ( A ) LENGTH: 38 base pairs
      ( B ) TYPE: nucleic acid ( C ) STRANDEDNESS: single
                        ( D ) TOPOLOGY: linear ( i i ) MOLECULE TYPE: cDNA ( i v ) ANTI-SENSE: NO ( v i ) ORIGINAL SOURCE:
                        ( A ) ORGANISM: Homo sapiens or Monkey ( v i i i ) POSITION IN GENOME:
                        ( A ) CHROMOSOME/SEGMENT: lambda light chain primer with BglII s ( x i ) SEQUENCE DESCRIPTION: SEQ ID NO:45:

ATCACAGATC TCTCACCATG ACTTGGACCC CACTCCTC                                    3 8

( 2 ) INFORMATION FOR SEQ ID NO:46:

( i ) SEQUENCE CHARACTERISTICS:
                        ( A ) LENGTH: 36 base pairs
                        ( B ) TYPE: nucleic acid
                        ( C ) STRANDEDNESS: single
                        ( D ) TOPOLOGY: linear ( i i ) MOLECULE TYPE: cDNA ( i v ) ANTI-SENSE: YES ( v i ) ORIGINAL SOURCE:
                        ( A ) ORGANISM: Homo sapiens or Monkey ( v i i i ) POSITION IN GENOME:
                        ( A ) CHROMOSOME/SEGMENT: kappa light chain primer with KpnI sit ( x i ) SEQUENCE DESCRIPTION: SEQ ID NO:46:

CCGTTTGATT TCCAGCTTGG TACCTCCACC GAACGT                                      3 6

( 2 ) INFORMATION FOR SEQ ID NO:47:

( i ) SEQUENCE CHARACTERISTICS:
                        ( A ) LENGTH: 30 base pairs
                        ( B ) TYPE: nucleic acid
                        ( C ) STRANDEDNESS: single
                        ( D ) TOPOLOGY: linear ( i i ) MOLECULE TYPE: cDNA ( i v ) ANTI-SENSE: YES ( v i ) ORIGINAL SOURCE:
                        ( A ) ORGANISM: Homo sapiens or Monkey ( v i i i ) POSITION IN GENOME:
                        ( A ) CHROMOSOME/SEGMENT: kappa light chain primer with BsiWI si ( x i ) SEQUENCE DESCRIPTION: SEQ ID NO:47:

TGCAGCATCC GTACGTTTGA TTTCCAGCTT                                             3 0

( 2 ) INFORMATION FOR SEQ ID NO:48:

( i ) SEQUENCE CHARACTERISTICS:
                        ( A ) LENGTH: 30 base pairs
                        ( B ) TYPE: nucleic acid
                        ( C ) STRANDEDNESS: single
                        ( D ) TOPOLOGY: linear ( i i ) MOLECULE TYPE: cDNA ( i v ) ANTI-SENSE: YES ( v i ) ORIGINAL SOURCE:
                        ( A ) ORGANISM: Homo sapiens or Monkey ( v i i i ) POSITION IN GENOME:

(A) CHROMOSOME/SEGMENT: lambda light chain primer with HindII
                        and Kpn1 sites ( x i ) SEQUENCE DESCRIPTION: SEQ ID NO:48:

ACCTAGGACG GTAAGCTTGG TACCTCCGCC                                              30

( 2 ) INFORMATION FOR SEQ ID NO:49:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: cDNA ( i v ) ANTI-SENSE: YES ( v i ) ORIGINAL SOURCE:
    ( A ) ORGANISM: Homo sapiens or Monkey ( v i i i ) POSITION IN GENOME:
    ( A ) CHROMOSOME/SEGMENT: lambda light chain primer with Kpn1 si ( x i ) SEQUENCE DESCRIPTION: SEQ ID NO:49:

ACCTAGGACG GTCASSTTGG TACCTCCGCC GAACAC                                       36

( 2 ) INFORMATION FOR SEQ ID NO:50:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( i v ) ANTI-SENSE: YES ( v i ) ORIGINAL SOURCE:
    ( A ) ORGANISM: Homo sapiens or Monkey ( v i i i ) POSITION IN GENOME:
    ( A ) CHROMOSOME/SEGMENT: lambda light chain primer with AvrII s ( x i ) SEQUENCE DESCRIPTION: SEQ ID NO:50:

CTTGGGCTGA CCTAGGACGG TCAGCCG                                                 27

( 2 ) INFORMATION FOR SEQ ID NO:51:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( i v ) ANTI-SENSE: NO ( v i i i ) POSITION IN GENOME:
    ( A ) CHROMOSOME/SEGMENT: heavy chain variable region ( x i ) SEQUENCE DESCRIPTION: SEQ ID NO:51:

CCATGGACTG GACCTGG                                                            17

( 2 ) INFORMATION FOR SEQ ID NO:52:

( i ) SEQUENCE CHARACTERISTICS:
    ( A ) LENGTH: 20 base pairs
    ( B ) TYPE: nucleic acid
    ( C ) STRANDEDNESS: single (D) TOPOLOGY: linear (i i) MOLECULE TYPE: cDNA (i v) ANTI-SENSE: NO (v i i i) POSITION IN GENOME:
    (A) CHROMOSOME/SEGMENT: heavy chain variable region (x i) SEQUENCE DESCRIPTION: SEQ ID NO:52:

ATGGACATAC TTTGTTCCAC      20

(2) INFORMATION FOR SEQ ID NO:53:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: cDNA (i v) ANTI-SENSE: NO (v i i i) POSITION IN GENOME:
    (A) CHROMOSOME/SEGMENT: heavy chain variable region (x i) SEQUENCE DESCRIPTION: SEQ ID NO:53:

CCATGGAGTT TGGGCTGAGC      20

(2) INFORMATION FOR SEQ ID NO:54:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: cDNA (i v) ANTI-SENSE: NO (v i i i) POSITION IN GENOME:
    (A) CHROMOSOME/SEGMENT: heavy chain variable region (x i) SEQUENCE DESCRIPTION: SEQ ID NO:54:

ATGAAACACC TGTGGTTCTT      20

(2) INFORMATION FOR SEQ ID NO:55:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: cDNA (i v) ANTI-SENSE: NO (v i i i) POSITION IN GENOME:
    (A) CHROMOSOME/SEGMENT: heavy chain variable region (x i) SEQUENCE DESCRIPTION: SEQ ID NO:55:

ATGGGGTCAA CCGCCATCCT      20

(2) INFORMATION FOR SEQ ID NO:56:

(i) SEQUENCE CHARACTERISTICS:
    (A) LENGTH: 20 base pairs
    (B) TYPE: nucleic acid
    (C) STRANDEDNESS: single

```
                    ( D ) TOPOLOGY: linear ( i i ) MOLECULE TYPE: cDNA ( i v ) ANTI-SENSE: NO ( v i i i ) POSITION IN GENOME:
                    ( A ) CHROMOSOME/SEGMENT: heavy chain variable region ( x i ) SEQUENCE DESCRIPTION: SEQ ID NO:56:

ATGTCTGTCT CCTTCCTCAT                                                                            20

( 2 ) INFORMATION FOR SEQ ID NO:57:

( i ) SEQUENCE CHARACTERISTICS:
                    ( A ) LENGTH: 16 base pairs
                    ( B ) TYPE: nucleic acid
                    ( C ) STRANDEDNESS: single
                    ( D ) TOPOLOGY: linear ( i i ) MOLECULE TYPE: cDNA ( i v ) ANTI-SENSE: YES ( v i i i ) POSITION IN GENOME:
                    ( A ) CHROMOSOME/SEGMENT: heavy chain constant region ( x i ) SEQUENCE DESCRIPTION: SEQ ID NO:57:

TTGGGGCGGA TGCACT                                                                                16

( 2 ) INFORMATION FOR SEQ ID NO:58:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( i i ) MOLECULE TYPE: cDNA ( i v ) ANTI-SENSE: YES ( v i i i ) POSITION IN GENOME:
                    ( A ) CHROMOSOME/SEGMENT: heavy chain constant region ( x i ) SEQUENCE DESCRIPTION: SEQ ID NO:58:

GATGGGCCCT TGGTGGA                                                                               17

( 2 ) INFORMATION FOR SEQ ID NO:59:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: cDNA ( v i i i ) POSITION IN GENOME:
                    ( A ) CHROMOSOME/SEGMENT: light chain variable region ( x i ) SEQUENCE DESCRIPTION: SEQ ID NO:59:

GATGACCCAG TCTCCAKCCT C                                                                          21

( 2 ) INFORMATION FOR SEQ ID NO:60:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear
```

( i i ) MOLECULE TYPE: cDNA ( v i i i ) POSITION IN GENOME:
    ( A ) CHROMOSOME/SEGMENT: lambda light chain variable region ( x i ) SEQUENCE DESCRIPTION: SEQ ID NO:60:

CTCAYTYRCT GCMCAGGGTC C 21

( 2 ) INFORMATION FOR SEQ ID NO:61:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: YES ( v i i i ) POSITION IN GENOME:
        ( A ) CHROMOSOME/SEGMENT: kappa light chain constant region ( x i ) SEQUENCE DESCRIPTION: SEQ ID NO:61:

AAGACAGATG GTGCAGCCA 19

( 2 ) INFORMATION FOR SEQ ID NO:62:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: YES ( v i i i ) POSITION IN GENOME:
        ( A ) CHROMOSOME/SEGMENT: lambda light chain constant region ( x i ) SEQUENCE DESCRIPTION: SEQ ID NO:62:

GGAACAGAGT GACCGAGGGG 20

( 2 ) INFORMATION FOR SEQ ID NO:63:

( i ) SEQUENCE CHARACTERISTICS:
        ( A ) LENGTH: 128 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Homo sapiens ( v i i i ) POSITION IN GENOME:
        ( A ) CHROMOSOME/SEGMENT: VH1 consensus ( x i ) SEQUENCE DESCRIPTION: SEQ ID NO:63:

Xaa Val Gln Leu Val Gln Ser Gly Ala Glu Val Lys Lys Pro Gly Xaa
1               5                   10                  15

Ser Val Xaa Val Ser Cys Lys Ala Ser Gly Tyr Thr Phe Ser Asp Tyr
            20                  25                  30

Xaa Ile His Trp Val Arg Gln Ala Pro Gly Xaa Gly Leu Glu Trp Xaa
        35                  40                  45

Gly Xaa Ile Asn Pro Ser Xaa Gly Xaa Thr Asn Tyr Ala Pro Xaa Phe
    50              55              60

| Gln | Gly | Arg | Val | Thr | Xaa | Thr | Xaa | Asp | Xaa | Ser | Xaa | Asn | Thr | Ala | Tyr |
| 65 | | | | | 70 | | | | | 75 | | | | | 80 |

| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |

| Ala | Arg | Xaa | Tyr | Gly | Phe | Tyr | Ser | Asn | Asp | Tyr | Xaa | Xaa | Xaa | Xaa | Xaa |
| | | | 100 | | | | | 105 | | | | | 110 | | |

| Tyr | Thr | Xaa | Asp | Tyr | Trp | Gly | Gln | Gly | Thr | Leu | Val | Thr | Val | Ser | Ser |
| | | 115 | | | | | 120 | | | | | 125 | | | |

( 2 ) INFORMATION FOR SEQ ID NO:64:

( i ) SEQUENCE CHARACTERISTICS:
        ( A ) LENGTH: 121 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: clone 1- 2

( x i ) SEQUENCE DESCRIPTION: SEQ ID NO:64:

| Xaa | Val | Gln | Leu | Val | Gln | Ser | Gly | Ala | Glu | Val | Lys | Lys | Pro | Gly | Xaa |
| 1 | | | | 5 | | | | | 10 | | | | | 15 | |

| Ser | Val | Xaa | Val | Ser | Cys | Lys | Ala | Ser | Gly | Phe | Asn | Phe | Gly | Asn | Tyr |
| | | | 20 | | | | | 25 | | | | | 30 | | |

| Ala | Ile | Ser | Trp | Val | Arg | Gln | Ala | Pro | Gly | Xaa | Gly | Leu | Glu | Trp | Xaa |
| | | 35 | | | | | 40 | | | | | 45 | | | |

| Gly | Trp | Ile | Asn | Thr | Asp | Thr | Gly | Asn | Pro | Thr | Tyr | Ala | Gln | Gly | Phe |
| | 50 | | | | | 55 | | | | | 60 | | | | |

| Lys | Glu | Arg | Val | Thr | Phe | Thr | Met | Asp | Xaa | Ser | Xaa | Asn | Thr | Ala | Tyr |
| 65 | | | | | 70 | | | | | 75 | | | | | 80 |

| Met | Lys | Ile | Ser | Leu | Leu | Lys | Ser | Glu | Asp | Thr | Ala | Val | Tyr | Tyr | Cys |
| | | | | 85 | | | | | 90 | | | | | 95 | |

| Ala | Arg | Val | Val | Gly | Thr | Thr | Tyr | Ala | Glu | Tyr | Phe | Glu | Phe | Trp | Gly |
| | | | 100 | | | | | 105 | | | | | 110 | | |

| Gln | Gly | Ala | Leu | Val | Thr | Val | Ser | Ser |
| | | 115 | | | | | 120 | |

( 2 ) INFORMATION FOR SEQ ID NO:65:

( i ) SEQUENCE CHARACTERISTICS:
        ( A ) LENGTH: 119 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: clone 1- 14

( x i ) SEQUENCE DESCRIPTION: SEQ ID NO:65:

| Xaa | Val | Gln | Gln | Val | Gln | Ser | Gly | Ala | Glu | Val | Lys | Lys | Pro | Gly | Thr |
| 1 | | | | 5 | | | | | 10 | | | | | 15 | |

| Ser | Val | Xaa | Val | Ser | Cys | Lys | Ala | Ser | Gly | Tyr | Thr | Phe | Thr | Ser | Tyr |
| | | | 20 | | | | | 25 | | | | | 30 | | |

```
Tyr Ile Asn Trp Val Arg Gln Ala Pro Gly Xaa Val Leu Glu Trp Ser
         35                  40                  45

Gly Trp Ile Asn Pro Ser Asn Gly Asn Thr Gly Tyr Ala Gln Lys Phe
     50                  55                  60

Gln Gly Arg Val Thr Xaa Thr Xaa Asp Xaa Ser Xaa Asn Thr Ala Tyr
 65              70              75                          80

Met Glu Leu Asn Ser Leu Arg Ser Glu Asp Thr Ala Val Tyr Tyr Cys
             85                  90                      95

Ala Arg Met Tyr Ser Trp Lys Gly Thr Phe Asp Tyr Trp Gly Gln Gly
             100                 105                 110

Thr Leu Val Thr Val Ser Ser
             115
```

(2) INFORMATION FOR SEQ ID NO:66:

(i) SEQUENCE CHARACTERISTICS:
        (A) LENGTH: 130 amino acids
        (B) TYPE: amino acid
        (C) STRANDEDNESS: Not Relevant
        (D) TOPOLOGY: Not Relevant (ii) MOLECULE TYPE: peptide (vi) ORIGINAL SOURCE:
        (A) ORGANISM: Homo sapiens (viii) POSITION IN GENOME:
        (A) CHROMOSOME/SEGMENT: VH2 consensus (xi) SEQUENCE DESCRIPTION: SEQ ID NO:66:

```
Xaa Val Thr Leu Arg Glu Ser Gly Pro Xaa Leu Val Lys Pro Thr Glu
 1               5                  10                  15

Thr Leu Thr Leu Thr Cys Thr Val Ser Gly Phe Ser Leu Ser Thr Xaa
             20                  25                  30

Gly Met Xaa Val Gly Trp Ile Arg Gln Pro Pro Gly Lys Xaa Leu Glu
         35                  40                  45

Trp Leu Ala Arg Ile Asn Xaa Trp Asp Asp Asp Lys Tyr Tyr Ser Thr
     50                  55                  60

Ser Leu Arg Ser Arg Leu Thr Ile Ser Lys Asp Thr Ser Lys Asn Gln
 65              70                  75                      80

Val Val Leu Xaa Xaa Xaa Xaa Xaa Asp Pro Xaa Asp Thr Ala Thr Tyr
             85                  90                      95

Tyr Cys Ala Arg Arg Xaa Pro Arg Xaa Xaa Xaa Gly Asp Xaa Gly Xaa
             100                 105                 110

Tyr Xaa Xaa Ala Phe Asp Val Trp Gly Gln Gly Thr Thr Val Thr Val
     115                 120                 125

Ser Ser
 130
```

(2) INFORMATION FOR SEQ ID NO:67:

(i) SEQUENCE CHARACTERISTICS:
        (A) LENGTH: 116 amino acids
        (B) TYPE: amino acid
        (C) STRANDEDNESS: Not Relevant
        (D) TOPOLOGY: Not Relevant (ii) MOLECULE TYPE: peptide (vi) ORIGINAL SOURCE:
        (A) ORGANISM: Monkey (viii) POSITION IN GENOME:
        (A) CHROMOSOME/SEGMENT: VH2 clone 2-3

( x i ) SEQUENCE DESCRIPTION: SEQ ID NO:67:

| | | | | | | | | | | | | | | | |
|---|---|---|---|---|---|---|---|---|---|---|---|---|---|---|---|
| Xaa<br>1 | Val | Thr | Leu | Arg<br>5 | Glu | Ser | Gly | Pro | Xaa<br>10 | Leu | Val | Lys | Pro | Thr<br>15 | Glu |
| Thr | Leu | Thr | Leu<br>20 | Thr | Cys | Thr | Val | Ser<br>25 | Gly | Phe | Ser | Leu | Ser<br>30 | Thr | Ser |
| Gly | Thr | Gly<br>35 | Tyr | Ser | Trp | Ile | Arg<br>40 | Gln | Pro | Pro | Gly | Lys<br>45 | Xaa | Leu | Glu |
| Trp | Leu<br>50 | Ala | Arg | Ile | Asp | Trp<br>55 | Asp | Asn | Asp | Arg | Tyr<br>60 | Tyr | Ser | Thr | Ser |
| Leu<br>65 | Lys | Asn | Arg | Leu | Thr<br>70 | Ile | Ser | Lys | Asp | Thr<br>75 | Ser | Lys | Asn | Gln | Val<br>80 |
| Val | Leu | Xaa | Xaa | Xaa<br>85 | Xaa | Xaa | Asp | Pro | Leu<br>90 | Asp | Thr | Ala | Thr | Tyr<br>95 | Tyr |
| Cys | Ala | Arg | Gly<br>100 | Gly | Ser | Ile | Asp | Tyr<br>105 | Trp | Gly | Gln | Gly | Val<br>110 | Thr | Val |
| Thr | Val | Ser<br>115 | Ser | | | | | | | | | | | | |

( 2 ) INFORMATION FOR SEQ ID NO:68:

( i ) SEQUENCE CHARACTERISTICS:
        ( A ) LENGTH: 121 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: VH2 clone 2- 13

( x i ) SEQUENCE DESCRIPTION: SEQ ID NO:68:

| | | | | | | | | | | | | | | | |
|---|---|---|---|---|---|---|---|---|---|---|---|---|---|---|---|
| Xaa<br>1 | Val | Thr | Leu | Arg<br>5 | Glu | Ser | Gly | Pro | Xaa<br>10 | Leu | Val | Lys | Pro | Thr<br>15 | Glu |
| Thr | Leu | Thr | Leu<br>20 | Thr | Cys | Thr | Val | Ser<br>25 | Gly | Phe | Ser | Leu | Ser<br>30 | Ala | Ser |
| Gly | Thr | Gly<br>35 | Val | Ala | Trp | Ile | Arg<br>40 | Gln | Ser | Pro | Gly | Lys<br>45 | Xaa | Leu | Glu |
| Trp | Leu<br>50 | Thr | Ser | Ile | Phe | Trp<br>55 | Thr | Gly | Val | Lys | Tyr<br>60 | Tyr | Asn | Thr | Ser |
| Leu<br>65 | Lys | Asn | Arg | Leu | Thr<br>70 | Ile | Ser | Ser | Asp | Thr<br>75 | Ser | Lys | Asp | Gln | Val<br>80 |
| Val | Leu | Ala | Xaa | Xaa<br>85 | Xaa | Xaa | Asp | Pro | Ile<br>90 | Asp | Thr | Ala | Thr | Tyr<br>95 | Tyr |
| Cys | Gly | Arg | Gly<br>100 | Val | Tyr | Trp | Ser | Gly<br>105 | Tyr | Ser | Phe | Asp | Tyr<br>110 | Trp | Gly |
| Gln | Gly | Ala | Thr<br>115 | Val | Thr | Val | Ser<br>120 | Ser | | | | | | | |

( 2 ) INFORMATION FOR SEQ ID NO:69:

( i ) SEQUENCE CHARACTERISTICS:
        ( A ) LENGTH: 125 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
    ( A ) ORGANISM: Monkey ( v i i i ) POSITION IN GENOME:
    ( A ) CHROMOSOME/SEGMENT: VH2 clone 2-10

( x i ) SEQUENCE DESCRIPTION: SEQ ID NO:69:

```
Xaa Val Thr Leu Arg Glu Ser Gly Pro Xaa Leu Val Lys Pro Thr Glu
 1               5                  10                  15

Thr Leu Thr Leu Thr Cys Thr Val Ser Gly Phe Ser Leu Ser Thr Ser
            20                  25                  30

Glu Thr Gly Val Gly Trp Ile Arg Gln Pro Pro Gly Lys Xaa Leu Glu
        35                  40                  45

Trp Leu Ala Ser Ile Tyr Trp Asn Asp Val Lys Tyr Tyr Ile Thr Phe
    50                  55                  60

Leu Lys Ser Arg Leu Thr Ile Ser Arg Asp Thr Ser Lys Asn Gln Val
65                  70                  75                  80

Val Leu Xaa Xaa Xaa Xaa Xaa Asp Pro Xaa Asp Thr Ala Thr Tyr Tyr
                85                  90                  95

Cys Ala Arg Ile Pro Gly Thr Ala Gly Thr Val Pro Tyr Tyr Thr Leu
            100                 105                 110

Asp Ser Trp Gly Gln Gly Ala Val Val Thr Val Ser Ser
            115                 120                 125
```

( 2 ) INFORMATION FOR SEQ ID NO:70:

( i ) SEQUENCE CHARACTERISTICS:
        ( A ) LENGTH: 130 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Homo sapiens ( v i i i ) POSITION IN GENOME:
        ( A ) CHROMOSOME/SEGMENT: VH3 consensus ( x i ) SEQUENCE DESCRIPTION: SEQ ID NO:70:

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Ala Met His Trp Val Arg Gln Ala Pro Gly Lys Gly Leu Glu Trp Val
        35                  40                  45

Xaa His Ile Glu Glu Lys Xaa Asn Gly Ser Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Pro Glu Val Glu Ser Leu Xaa Xaa Xaa Phe Xaa
            100                 105                 110

Tyr Xaa Xaa Phe Phe Asp Ser Trp Gly Gln Gly Thr Leu Val Thr Val
            115                 120                 125

Ser Ser
    130
```

5,750,105

69

-continued ( 2 ) INFORMATION FOR SEQ ID NO:71:

( i ) SEQUENCE CHARACTERISTICS:
        ( A ) LENGTH: 123 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: VH3 clone 3- 34

( x i ) SEQUENCE DESCRIPTION: SEQ ID NO:71:

```
Glu Val Gln Leu Glu Glu Ser Gly Gly Gly Leu Val Gln Phe Gly Gly
  1               5                  10                  15

Ser Leu Arg Leu Ser Cys Ala Ala Ser Gly Phe Thr Phe Ser Thr Tyr
             20                  25                  30

Asp Met Thr Trp Val Arg Gln Ala Pro Gly Lys Gly Leu Glu Trp Val
         35                  40                  45

Xaa Arg Ile Ser Trp Asn Ser Gly Thr Ile Tyr Tyr Ala Ser Ser Val
     50                  55                  60

Lys Gly Arg Phe Thr Ile Ser Arg Asp Asp Ser Lys Asn Thr Leu Tyr
 65                  70                  75                  80

Leu Gln Met Asn Ser Arg Arg Ala Glu Asp Thr Ala Val Tyr Tyr Cys
                 85                  90                  95

Ala Arg Gly Thr Ala Leu Cys Ser Asp Ser Gly Cys Ser Ser Asp Val
             100                 105                 110

Trp Gly Gln Gly Thr Leu Val Thr Val Ser Ser
             115                 120
```

( 2 ) INFORMATION FOR SEQ ID NO:72:

( i ) SEQUENCE CHARACTERISTICS:
        ( A ) LENGTH: 122 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: VH3 clone 3- 36

( x i ) SEQUENCE DESCRIPTION: SEQ ID NO:72:

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Glu Tyr
             20                  25                  30

Ser Ile His Trp Val Arg Gln Ala Gln Gly Lys Gly Leu Arg Trp Val
         35                  40                  45

Xaa Leu Ala Gly Lys Lys Ala Asp Arg Tyr Lys Thr Glu Tyr Ala Thr
     50                  55                  60

Ala Val Lys Gly Arg Phe Thr Ile Ser Arg Asp Asp Ser Lys Ser Thr
 65                  70                  75                  80

Leu Tyr Leu Gln Met Thr Ser Leu Arg Ala Glu Asp Thr Ala Val Tyr
                 85                  90                  95

Tyr Cys Ala Arg Pro Val Leu Gly Asp Arg Trp Phe Phe Asp Leu Trp
```

```
                    100                    105                       110
      Gly  Gln  Gly  Thr  Pro  Ile  Thr  Val  Ser  Ser
                    115                    120
```

( 2 ) INFORMATION FOR SEQ ID NO:73:

( i ) SEQUENCE CHARACTERISTICS:
        ( A ) LENGTH: 128 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: VH3 clone 3- 40

( x i ) SEQUENCE DESCRIPTION: SEQ ID NO:73:

```
      Glu  Val  Gln  Leu  Val  Glu  Ser  Gly  Gly  Gly  Leu  Val  Gln  Pro  Gly  Gly
      1                  5                         10                        15

Ser  Leu  Arg  Leu  Ser  Cys  Ala  Ala  Ser  Gly  Phe  Thr  Phe  Ser  Ser  Tyr
                         20                        25                       30

Asp  Met  Asn  Trp  Val  Arg  Gln  Ala  Pro  Gly  Lys  Gly  Leu  Glu  Trp  Val
                35                       40                        45

Xaa  Tyr  Ile  Ser  Ser  Ala  Ser  Gly  Tyr  Ile  Tyr  Tyr  Ala  Asp  Ser  Val
           50                             55                        60

Lys  Gly  Arg  Phe  Thr  Ile  Ser  Arg  Asp  Phe  Ser  Lys  Asn  Thr  Leu  Ser
      65                            70                        75                      80

Leu  Gln  Met  Asn  Ser  Leu  Arg  Ala  Glu  Asp  Thr  Ala  Val  Tyr  Tyr  Cys
                          85                        90                       95

Ala  Arg  Gly  Gln  Pro  Val  Leu  Gln  Phe  Leu  Glu  Trp  Leu  Leu  Pro  Thr
                          100                       105                      110

Thr  Gly  Ser  Asp  Val  Trp  Gly  Pro  Gly  Val  Leu  Val  Thr  Val  Ser  Ser
                          115                      120                       125
```

( 2 ) INFORMATION FOR SEQ ID NO:74:

( i ) SEQUENCE CHARACTERISTICS:
        ( A ) LENGTH: 116 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: VH3 clone 3- 9

( x i ) SEQUENCE DESCRIPTION: SEQ ID NO:74:

```
      Glu  Val  Gln  Leu  Val  Glu  Ser  Gly  Gly  Gly  Leu  Val  Gln  Pro  Gly  Gly
      1                  5                         10                        15

Ser  Leu  Ser  Leu  Ser  Cys  Ala  Ala  Ser  Gly  Phe  Thr  Phe  Ser  Asn  Tyr
                         20                        25                       30

Asn  Met  Asp  Trp  Val  Arg  Gln  Ser  Pro  Gly  Lys  Gly  Leu  Glu  Trp  Val
                35                       40                        45

Xaa  Arg  Val  Ile  Arg  Lys  Gly  Ala  Arg  Thr  Lys  Tyr  Ala  Ala  Ser  Val
           50                             55                        60

Lys  Gly  Arg  Phe  Thr  Ile  Ser  Arg  Asp  Asp  Ser  Lys  Asn  Thr  Leu  Tyr
```

```
     65                         70                         75                          80
     Leu   Gln   Met   Asn   Ser   Leu   Arg   Ala   Glu   Asp   Thr   Ala   Val   Tyr   Tyr   Cys
                             85                          90                          95

Ala   Arg   Asp   Val   Ala   Ala   Ala   Gly   Thr   Gly   Gly   Gln   Gly   Val   Leu   Val
                       100                         105                         110

Thr   Val   Ser   Ser
                       115
```

( 2 ) INFORMATION FOR SEQ ID NO:75:

( i ) SEQUENCE CHARACTERISTICS:
        ( A ) LENGTH: 98 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Homo sapiens ( v i i i ) POSITION IN GENOME:
        ( A ) CHROMOSOME/SEGMENT: VH4 consensus ( x i ) SEQUENCE DESCRIPTION: SEQ ID NO:75:

```
     Gln   Val   Gln   Leu   Gln   Glu   Ser   Gly   Pro   Gly   Leu   Val   Lys   Pro   Ser   Glu
     1                       5                          10                           15

Thr   Leu   Ser   Leu   Thr   Cys   Ala   Val   Ser   Gly   Gly   Ser   Ile   Ser   Ser   Ser
                       20                          25                          30

Tyr   Tyr   Trp   Ser   Trp   Ile   Arg   Gln   Pro   Pro   Gly   Lys   Gly   Leu   Glu   Trp
                       35                          40                          45

Ile   Gly   Tyr   Ile   Tyr   Tyr   Ser   Gly   Ser   Thr   Tyr   Tyr   Asn   Pro   Ser   Leu
           50                          55                          60

Lys   Ser   Arg   Val   Thr   Ile   Ser   Val   Asp   Thr   Ser   Lys   Asn   Gln   Phe   Ser
     65                          70                          75                           80

Leu   Lys   Leu   Ser   Ser   Val   Thr   Ala   Ala   Asp   Thr   Ala   Val   Tyr   Tyr   Cys
                             85                          90                          95

Ala   Arg
```

( 2 ) INFORMATION FOR SEQ ID NO:76:

( i ) SEQUENCE CHARACTERISTICS:
        ( A ) LENGTH: 125 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: VH4 clone 4-14

( x i ) SEQUENCE DESCRIPTION: SEQ ID NO:76:

```
     Gln   Met   Gln   Leu   Gln   Glu   Ser   Gly   Pro   Gly   Leu   Val   Lys   Pro   Ser   Glu
     1                       5                          10                           15

Thr   Leu   Ser   Leu   Thr   Cys   Ala   Val   Ser   Gly   Gly   Ser   Ile   Ser   Ser   Ser
                       20                          25                          30

Tyr   Asp   Trp   Thr   Trp   Ile   Arg   Gln   Pro   Pro   Gly   Met   Gly   Leu   Glu   Trp
                       35                          40                          45

Ile   Ala   Val   Ile   Ser   Gly   Asn   Ser   Gly   Ser   Ala   Asp   Tyr   Asn   Pro   Ser
           50                          55                          60
```

-continued

```
Leu Lys Asn Arg Val Thr Ile Ser Val Asp Thr Ser Asn Asn Gln Phe
 65              70              75                      80

Ser Leu Lys Met Thr Ser Val Thr Ala Ala Asp Thr Ala Ile Tyr Tyr
                 85              90              95

Cys Ala Arg Gly Asp Val Thr Ser Gly Trp Tyr Arg Gly Tyr Phe Asp
            100             105             110

Ser Trp Gly Gln Gly Cys Leu Val Thr Val Ser Ser Gly
        115             120             125
```

(2) INFORMATION FOR SEQ ID NO:77:

(i) SEQUENCE CHARACTERISTICS:
        (A) LENGTH: 119 amino acids
        (B) TYPE: amino acid
        (C) STRANDEDNESS: Not Relevant
        (D) TOPOLOGY: Not Relevant (ii) MOLECULE TYPE: peptide (vi) ORIGINAL SOURCE:
        (A) ORGANISM: Monkey (viii) POSITION IN GENOME:
        (A) CHROMOSOME/SEGMENT: VH4 clone 4-14

(xi) SEQUENCE DESCRIPTION: SEQ ID NO:77:

```
Gln Val Gln Leu Gln Glu Ser Gly Pro Gly Leu Val Lys Pro Ser Glu
 1               5              10                      15

Thr Leu Ser Leu Thr Cys Ala Val Ser Gly Gly Ser Ile Ser Ser Gly
                 20              25              30

Tyr Tyr Trp Gly Trp Ile Arg Gln Thr Pro Gly Lys Gly Leu Glu Trp
             35              40              45

Ile Gly Ser Leu Gln Gly Arg Gly Gly Asn Lys Tyr Leu Asn Leu Cys
    50              55              60

Leu Lys Ser Arg Val Thr Leu Ser Ala Asp Thr Ser Lys Asn Gln Phe
 65              70              75                      80

Ser Leu Lys Leu Ser Ser Val Thr Ala Ala Asp Thr Ala Val Tyr Tyr
                 85              90              95

Cys Ala Arg Val Gly Asp Asn Arg Phe Asp Val Trp Gly Pro Gly Val
            100             105             110

Leu Val Thr Val Ser Ser Gly
            115
```

(2) INFORMATION FOR SEQ ID NO:78:

(i) SEQUENCE CHARACTERISTICS:
        (A) LENGTH: 124 amino acids
        (B) TYPE: amino acid
        (C) STRANDEDNESS: Not Relevant
        (D) TOPOLOGY: Not Relevant (ii) MOLECULE TYPE: peptide (vi) ORIGINAL SOURCE:
        (A) ORGANISM: Monkey (viii) POSITION IN GENOME:
        (A) CHROMOSOME/SEGMENT: VH4 clone 4-16

(xi) SEQUENCE DESCRIPTION: SEQ ID NO:78:

```
Gln Val His Leu Gln Glu Ser Gly Pro Gly Leu Val Lys Pro Ser Glu
 1               5              10                      15

Thr Leu Ser Leu Thr Cys Ser Val Ser Gly Gly Ser Ile Ser Ser Ser
                 20              25              30
```

```
Gly Tyr Tyr Trp Gly Trp Ile Arg Gln Pro Pro Gly Lys Gly Leu Glu
         35                  40                    45

Trp Ile Gly Ser Ile His Gly Ser Gly Gly Ser Asn Ser Leu Asn Pro
     50              55                  60

Ser Leu Lys Ser Arg Val Thr Leu Ser Val Asp Thr Ser Gly Asn Lys
 65              70                  75                      80

Phe Ser Leu Lys Leu Ser Ser Val Thr Ala Ala Asp Thr Ala Val Tyr
             85                      90                  95

Phe Cys Ala Arg Glu Leu Tyr Ser Ser Ser Pro Tyr Tyr Phe Asp Phe
             100             105                 110

Trp Gly Gln Gly Val Arg Val Thr Val Ser Ser Gly
         115             120
```

(2) INFORMATION FOR SEQ ID NO:79:

(i) SEQUENCE CHARACTERISTICS:
      (A) LENGTH: 116 amino acids
      (B) TYPE: amino acid
      (C) STRANDEDNESS: Not Relevant
      (D) TOPOLOGY: Not Relevant (ii) MOLECULE TYPE: peptide (vi) ORIGINAL SOURCE:
      (A) ORGANISM: Monkey (viii) POSITION IN GENOME:
      (A) CHROMOSOME/SEGMENT: VH4 clone SC CHIM (xi) SEQUENCE DESCRIPTION: SEQ ID NO:79:

```
Gln Val Gln Leu Gln Glu Ser Gly Pro Gly Leu Val Lys Pro Ser Glu
 1               5                  10                  15

Thr Leu Ser Leu Thr Cys Ala Val Ser Gly Gly Ser Ile Ser Gly Tyr
             20                  25                  30

Tyr Trp Gly Trp Ile Arg Gln Thr Pro Gly Lys Gly Leu Glu Trp Ile
         35                  40                  45

Gly Ser Leu Gln Gly Arg Gly Gly Asn Lys Tyr Leu Asn Leu Ser Leu
     50              55                  60

Lys Ser Arg Val Thr Leu Ser Ala Asp Thr Ser Lys Asn Gln Phe Ser
 65              70                  75                      80

Leu Lys Leu Ser Ser Val Thr Ala Ala Asp Thr Ala Val Tyr Tyr Cys
             85                      90                  95

Ala Arg Gly Asp Asn Arg Phe Asp Val Trp Gly Pro Gly Val Leu Val
             100             105                 110

Thr Val Ser Ser
         115
```

(2) INFORMATION FOR SEQ ID NO:80:

(i) SEQUENCE CHARACTERISTICS:
      (A) LENGTH: 121 amino acids
      (B) TYPE: amino acid
      (C) STRANDEDNESS: Not Relevant
      (D) TOPOLOGY: Not Relevant (ii) MOLECULE TYPE: peptide (vi) ORIGINAL SOURCE:
      (A) ORGANISM: Monkey (viii) POSITION IN GENOME:
      (A) CHROMOSOME/SEGMENT: VH4 anti-CD4 CHIM (xi) SEQUENCE DESCRIPTION: SEQ ID NO:80:

Gln Val Gln Leu Gln Glu Ala Gly Pro Gly Leu Val Lys Pro Ser Glu
1               5                   10                  15

Thr Leu Ser Leu Thr Cys Ser Val Ser Gly Gly Ser Ile Ser Gly Asp
            20              25                  30

Tyr Tyr Trp Phe Trp Ile Arg Gln Pro Pro Gly Lys Gly Leu Glu Trp
        35                  40                  45

Ile Gly Tyr Ile Tyr Gly Ser Gly Gly Gly Thr Asn Tyr Asn Pro Ser
    50                  55                      60

Leu Asn Asn Arg Val Ser Ile Ser Ile Asp Thr Ser Lys Asn Leu Phe
65                  70              75                      80

Ser Leu Lys Leu Arg Ser Val Thr Ala Ala Asp Thr Ala Val Tyr Tyr
                85              90                      95

Cys Ala Ser Asn Ile Leu Lys Tyr Leu His Trp Leu Leu Tyr Trp Gly
            100             105                     110

Gln Gly Val Leu Val Thr Val Ser Ser
            115             120

(2) INFORMATION FOR SEQ ID NO:81:

(i) SEQUENCE CHARACTERISTICS:
  (A) LENGTH: 98 amino acids
  (B) TYPE: amino acid
  (C) STRANDEDNESS: Not Relevant
  (D) TOPOLOGY: Not Relevant (ii) MOLECULE TYPE: peptide (vi) ORIGINAL SOURCE:
  (A) ORGANISM: Homo sapiens (viii) POSITION IN GENOME:
  (A) CHROMOSOME/SEGMENT: VH5 consensus (xi) SEQUENCE DESCRIPTION: SEQ ID NO:81:

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20              25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                      60

Gln Gly His Val Thr Ile Ser Ala Asp Lys Ser Ile Ser Thr Ala Tyr
65                  70              75                      80

Leu Gln Trp Ser Ser Leu Lys Ala Ser Asp Thr Ala Met Tyr Tyr Cys
                85              90                      95

Ala Arg (2) INFORMATION FOR SEQ ID NO:82:

(i) SEQUENCE CHARACTERISTICS:
  (A) LENGTH: 123 amino acids
  (B) TYPE: amino acid
  (C) STRANDEDNESS: Not Relevant
  (D) TOPOLOGY: Not Relevant (ii) MOLECULE TYPE: peptide (vi) ORIGINAL SOURCE:
  (A) ORGANISM: Monkey (viii) POSITION IN GENOME:
  (A) CHROMOSOME/SEGMENT: VH5 clone 5-11

( x i ) SEQUENCE DESCRIPTION: SEQ ID NO:82:

| Glu | Val | Gln | Leu | Val | Gln | Ser | Gly | Gly | Glu | Val | Lys | Arg | Pro | Gly | Glu |
| 1 | | | | 5 | | | | | 10 | | | | | 15 | |

| Ser | Leu | Arg | Ile | Ser | Cys | Lys | Thr | Cys | Gly | Phe | Ser | Phe | Thr | Gly | Phe |
| | | | 20 | | | | | 25 | | | | | 30 | | |

| Trp | Ile | Ser | Trp | Val | Arg | Gln | Val | Pro | Gly | Gln | Gly | Leu | Glu | Trp | Val |
| | | 35 | | | | | 40 | | | | | 45 | | | |

| Gly | Arg | Val | Ser | Pro | Gly | Asp | Ser | Ile | Thr | Arg | Tyr | Asn | Pro | Ser | Phe |
| | 50 | | | | | 55 | | | | | 60 | | | | |

| Gln | Gly | His | Val | Thr | Ile | Ser | Ala | Asp | Lys | Ser | Ile | Thr | Thr | Thr | Phe |
| 65 | | | | | 70 | | | | | 75 | | | | | 80 |

| Leu | Gln | Trp | Asn | Ser | Leu | Lys | Ala | Ser | Asp | Thr | Ala | Met | Tyr | Tyr | Cys |
| | | | | 85 | | | | | 90 | | | | | 95 | |

| Ala | Gln | Arg | Ala | Gly | Asn | Gly | Asn | Tyr | Tyr | Gln | Asp | Phe | Tyr | Tyr | Trp |
| | | | | 100 | | | | | 105 | | | | | 110 | |

| Gly | His | Gly | Val | Leu | Val | Thr | Val | Ser | Ser | Gly | | | | | |
| | | 115 | | | | | 120 | | | | | | | | |

( 2 ) INFORMATION FOR SEQ ID NO:83:

( i ) SEQUENCE CHARACTERISTICS:
( A ) LENGTH: 116 amino acids
( B ) TYPE: amino acid
( C ) STRANDEDNESS: Not Relevant
( D ) TOPOLOGY: Not Relevant ( i i ) MOLECULE TYPE: peptide ( v i ) ORIGINAL SOURCE:
( A ) ORGANISM: Homo sapiens ( v i i i ) POSITION IN GENOME:
( A ) CHROMOSOME/SEGMENT: VK1 consensus ( x i ) SEQUENCE DESCRIPTION: SEQ ID NO:83:

| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |

| Asp | Arg | Val | Thr | Ile | Thr | Cys | Arg | Ala | Ser | Gln | Ser | Val | Xaa | Xaa | Ser |
| | | | 20 | | | | | 25 | | | | | 30 | | |

| Asp | Ile | Ser | Ser | Tyr | Leu | Asn | Trp | Tyr | Gln | Gln | Lys | Pro | Gly | Lys | Ala |
| | | 35 | | | | | 40 | | | | | 45 | | | |

| Pro | Lys | Leu | Leu | Ile | Tyr | Xaa | Ala | Ser | Ser | Leu | Glu | Ser | Gly | Val | Pro |
| | 50 | | | | | 55 | | | | | 60 | | | | |

| Ser | Arg | Phe | Ser | Gly | Ser | Gly | Ser | Gly | Thr | Asp | Phe | Thr | Leu | Thr | Ile |
| 65 | | | | | 70 | | | | | 75 | | | | | 80 |

| Ser | Ser | Leu | Gln | Pro | Glu | Asp | Phe | Ala | Thr | Tyr | Tyr | Cys | Gln | Gln | Tyr |
| | | | | 85 | | | | | 90 | | | | | 95 | |

| Asn | Ser | Leu | Pro | Xaa | Xaa | Tyr | Asp | Tyr | Thr | Phe | Gly | Gln | Gly | Thr | Lys |
| | | | 100 | | | | | 105 | | | | | 110 | | |

| Val | Glu | Ile | Lys | | | | | | | | | | | | |
| | | 115 | | | | | | | | | | | | | |

( 2 ) INFORMATION FOR SEQ ID NO:84:

( i ) SEQUENCE CHARACTERISTICS:
( A ) LENGTH: 108 amino acids
( B ) TYPE: amino acid
( C ) STRANDEDNESS: Not Relevant
( D ) TOPOLOGY: Not Relevant ( i i ) MOLECULE TYPE: peptide ( v i ) ORIGINAL SOURCE:
    ( A ) ORGANISM: Monkey ( v i i i ) POSITION IN GENOME:
    ( A ) CHROMOSOME/SEGMENT: VK1 clone K1-7

( x i ) SEQUENCE DESCRIPTION: SEQ ID NO:84:

```
Asp Ile Gln Met Thr Gln Ser Pro Ala Ser Leu Ser Ala Ser Val Gly
 1               5                  10                  15
Asp Lys Val Thr Ile Thr Cys Arg Ala Ser Gln Ser Phe Ser Ser Ser
                20                  25                  30
Leu Ala Trp Tyr Gln Gln Lys Pro Gly Lys Ala Pro Lys Leu Leu Ile
            35                  40                  45
Asp Ser Ala Ser Ser Leu Gln Ser Gly Val Pro Ser Arg Phe Ser Gly
        50              55                  60
Ser Lys Ser Gly Thr Asp Phe Thr Leu Thr Ile Ser Ser Leu Gln Pro
 65             70                  75                      80
Glu Asp Phe Ala Ser Tyr Tyr Cys Gln Gln Tyr Tyr Ser Tyr Pro Arg
                85                  90                  95
Leu Thr Phe Gly Gln Gly Thr Lys Val Glu Ile Lys
                100                 105
```

( 2 ) INFORMATION FOR SEQ ID NO:85:

( i ) SEQUENCE CHARACTERISTICS:
        ( A ) LENGTH: 108 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: VK1 clone K1-3

( x i ) SEQUENCE DESCRIPTION: SEQ ID NO:85:

```
Asp Ile Gln Met Thr Gln Ser Pro Ala Ser Leu Ser Ala Ser Val Gly
 1               5                  10                  15
Asp Arg Val Thr Ile Thr Cys Gln Ala Ser Gln Ser Val Ser Asn Leu
                20                  25                  30
Leu Ala Trp Tyr Gln Gln Lys Pro Gly Lys Ala Pro Lys Pro Leu Leu
            35                  40                  45
Ile Tyr Lys Ala Ser Ser Leu Glu Ser Gly Val Pro Ser Arg Phe Thr
        50              55                  60
Arg Ser Gly Ser Gly Thr Asp Phe Thr Leu Thr Ile Asn Ser Leu Glu
 65             70                  75                      80
Pro Glu Asp Phe Ala Thr Tyr Phe Cys Gln Gln Gly Asn Ser Tyr Pro
                85                  90                  95
Leu Thr Phe Gly Gly Gly Thr Lys Val Glu Ile Lys
                100                 105
```

( 2 ) INFORMATION FOR SEQ ID NO:86:

( i ) SEQUENCE CHARACTERISTICS:
        ( A ) LENGTH: 107 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
 ( A ) ORGANISM: Monkey ( v i i i ) POSITION IN GENOME:
 ( A ) CHROMOSOME/SEGMENT: VK1 clone K1- 14

( x i ) SEQUENCE DESCRIPTION: SEQ ID NO:86:

```
Asp Ile Gln Met Thr Gln Ser Pro Ala Ser Leu Ser Ala Ser Val Gly
1               5                   10                  15

Asp Arg Val Thr Val Thr Cys Arg Ala Ser Gln Gly Ile Asn Gln Glu
                20              25                  30

Leu Ser Trp Tyr Gln Gln Lys Pro Gly Lys Ala Pro Thr Leu Leu Ile
            35              40                  45

Tyr Ala Ala Ser Ser Leu Gln Thr Gly Val Pro Ser Arg Phe Ser Gly
    50                  55                  60

Ser Gly Ser Gly Thr Asp Phe Thr Leu Thr Ser Ser Ser Pro Glu Pro
65                  70                  75                  80

Glu Asp Val Ala Thr Glu Asp Cys Leu Gln Asp Tyr Met Ser Pro Trp
                85                  90                  95

Thr Phe Gly Gln Gly Thr Lys Val Glu Ile Lys
                100                 105
```

( 2 ) INFORMATION FOR SEQ ID NO:87:

( i ) SEQUENCE CHARACTERISTICS:
  ( A ) LENGTH: 49 amino acids
  ( B ) TYPE: amino acid
  ( C ) STRANDEDNESS: Not Relevant
  ( D ) TOPOLOGY: Not Relevant ( i i ) MOLECULE TYPE: peptide ( v i ) ORIGINAL SOURCE:
  ( A ) ORGANISM: Monkey ( x i ) SEQUENCE DESCRIPTION: SEQ ID NO:87:

```
Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Gly Ile Ser Ser Tyr
                20              25                  30

Leu Asn Trp Tyr Gln Gln Lys Pro Gly Lys Ala Pro Lys Leu Leu Ile
            35              40                  45

Leu
```

( 2 ) INFORMATION FOR SEQ ID NO:88:

( i ) SEQUENCE CHARACTERISTICS:
  ( A ) LENGTH: 112 amino acids
  ( B ) TYPE: amino acid
  ( C ) STRANDEDNESS: Not Relevant
  ( D ) TOPOLOGY: Not Relevant ( i i ) MOLECULE TYPE: peptide ( v i ) ORIGINAL SOURCE:
  ( A ) ORGANISM: Homo sapiens ( v i i i ) POSITION IN GENOME:
  ( A ) CHROMOSOME/SEGMENT: VK2 consensus ( x i ) SEQUENCE DESCRIPTION: SEQ ID NO:88:

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
```

|  |  |  |  |  | 20 |  |  |  |  | 25 |  |  |  |  | 30 |  |
|---|---|---|---|---|---|---|---|---|---|---|---|---|---|---|---|---|
| Asn | Gly | Asn<br>35 | Thr | Tyr | Leu | Asn | Trp<br>40 | Tyr | Leu | Gln | Lys | Pro<br>45 | Gly | Gln | Ser |
| Pro | Gln<br>50 | Leu | Leu | Ile | Tyr | Lys<br>55 | Val | Ser | Asn | Arg | Phe<br>60 | Ser | Gly | Val | Pro |
| Asp<br>65 | Arg | Phe | Ser | Gly | Ser<br>70 | Gly | Ser | Gly | Thr | Asp<br>75 | Phe | Thr | Leu | Lys | Ile<br>80 |
| Ser | Arg | Val | Glu | Ala<br>85 | Glu | Asp | Val | Gly | Val<br>90 | Tyr | Tyr | Cys | Met | Gln<br>95 | Ala |
| Leu | Gln | Ser | Pro<br>100 | Tyr | Thr | Phe | Gly | Gln<br>105 | Gly | Thr | Lys | Asn | Glu<br>110 | Ile | Lys |

( 2 ) INFORMATION FOR SEQ ID NO:89:

( i ) SEQUENCE CHARACTERISTICS:
       ( A ) LENGTH: 112 amino acids
       ( B ) TYPE: amino acid
       ( C ) STRANDEDNESS: Not Relevant
       ( D ) TOPOLOGY: Not Relevant ( i i ) MOLECULE TYPE: peptide ( v i ) ORIGINAL SOURCE:
       ( A ) ORGANISM: Monkey ( v i i i ) POSITION IN GENOME:
       ( A ) CHROMOSOME/SEGMENT: VKII clone K2-8

( x i ) SEQUENCE DESCRIPTION: SEQ ID NO:89:

| Asp<br>1 | Ile | Val | Met | Thr<br>5 | Gln | Ser | Pro | Ala | Ser<br>10 | Leu | Pro | Val | Thr | Leu<br>15 | Gly |
|---|---|---|---|---|---|---|---|---|---|---|---|---|---|---|---|
| Gly | Pro | Ala | Ser<br>20 | Ile | Ser | Cys | Thr | Ser<br>25 | Thr | Gln | Ser | Leu | Leu<br>30 | Ser | Gly |
| Asn | Gly | Tyr<br>35 | Ser | Tyr | Leu | Asn | Trp<br>40 | Tyr | Leu | Gln | Lys | Pro<br>45 | Gly | Gln | Ser |
| Pro | His<br>50 | Leu | Leu | Ile | Tyr | Tyr<br>55 | Asp | Ser | Tyr | Arg | Ala<br>60 | Ser | Gly | Val | Pro |
| Thr<br>65 | Arg | Phe | Ser | Gly | Ser<br>70 | Gly | Ser | Gly | Thr | Asp<br>75 | Phe | Thr | Leu | Lys | Ile<br>80 |
| Ser | Arg | Val | Glu | Ala<br>85 | Glu | Asp | Val | Gly | Val<br>90 | Tyr | Tyr | Cys | Met | Gln<br>95 | Thr |
| Leu | Gln | Ser | Pro<br>100 | Phe | Thr | Phe | Gly | Pro<br>105 | Gly | Thr | Lys | Asn | Asp<br>110 | Ile | Lys |

( 2 ) INFORMATION FOR SEQ ID NO:90:

( i ) SEQUENCE CHARACTERISTICS:
       ( A ) LENGTH: 109 amino acids
       ( B ) TYPE: amino acid
       ( C ) STRANDEDNESS: Not Relevant
       ( D ) TOPOLOGY: Not Relevant ( i i ) MOLECULE TYPE: peptide ( v i ) ORIGINAL SOURCE:
       ( A ) ORGANISM: Monkey ( v i i i ) POSITION IN GENOME:
       ( A ) CHROMOSOME/SEGMENT: VKII clone CHIM ( x i ) SEQUENCE DESCRIPTION: SEQ ID NO:90:

| Asp<br>1 | Leu | Ala | Met | Pro<br>5 | Gln | Ser | Pro | Ala | Ser<br>10 | Leu | Ala | Val | Thr | Pro<br>15 | Gly |
|---|---|---|---|---|---|---|---|---|---|---|---|---|---|---|---|
| Gln | Pro | Ala | Ser | Ile | Ser | Cys | Arg | Ala | Ser | Glu | Ser | Val | Ser | Phe | Phe |

-continued

```
                        20                      25                         30
        Gly Val Asn Leu Ile His Trp Tyr Leu Gln Lys Pro Gly Gln Pro Pro
                 35              40                  45
        Gln Leu Leu Ile Tyr Gln Ala Ser Asn Lys Asp Thr Gly Val Pro Ala
             50                  55                  60
        Arg Phe Ser Gly Ser Gly Ser Gly Thr Asp Phe Thr Leu Lys Phe Asn
        65                  70                  75                      80
        Pro Val Glu Ala Asp Asp Ala Gly Asp Tyr Tyr Cys Leu Gln Ser Lys
                         85                  90                      95
        Asn Ser Pro Arg Thr Phe Gly Gly Gly Thr Lys Asn Glu
                     100                 105
```

( 2 ) INFORMATION FOR SEQ ID NO:91:

( i ) SEQUENCE CHARACTERISTICS:
        ( A ) LENGTH: 109 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Homo sapiens ( v i i i ) POSITION IN GENOME:
        ( A ) CHROMOSOME/SEGMENT: Lambda VIII consensus ( x i ) SEQUENCE DESCRIPTION: SEQ ID NO:91:

```
        Ser Tyr Glu Leu Thr Gln Pro Pro Ser Val Ser Val Ser Pro Gly Gln
        1               5                   10                  15
        Thr Ala Arg Ile Thr Cys Ser Gly Asp Ala Leu Gly Gln Lys Tyr Val
                     20                  25                  30
        Tyr Trp Tyr Gln Gln Lys Pro Gly Gln Ala Pro Val Leu Val Ile Tyr
                 35                  40                  45
        Glu Asp Ser Lys Arg Pro Ser Gly Ile Pro Glu Arg Phe Ser Gly Ser
             50                  55                  60
        Asn Ser Gly Thr Thr Ala Thr Leu Thr Ile Ser Gly Val Glu Ala Xaa
        65                  70                  75                      80
        Asp Glu Ala Asp Tyr Tyr Cys Gln Ala Trp Asp Ser Xaa Thr Xaa Xaa
                         85                  90                      95
        Val Val Phe Gly Gly Gly Thr Lys Leu Thr Val Leu Gly
                     100                 105
```

( 2 ) INFORMATION FOR SEQ ID NO:92:

( i ) SEQUENCE CHARACTERISTICS:
        ( A ) LENGTH: 109 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: Lambda VIII anti-CD4

( x i ) SEQUENCE DESCRIPTION: SEQ ID NO:92:

```
        Ser Tyr Glu Leu Ser Gln Pro Arg Ser Val Ser Val Ser Pro Gly Gln
        1               5                   10                  15
        Thr Ala Gly Phe Thr Cys Gly Gly Asp Asn Val Gly Arg Lys Ser Val
```

-continued

```
                              20                        25                         30
        Gln  Trp  Tyr  Gln  Gln  Lys  Pro  Pro  Gln  Ala  Pro  Val  Leu  Val  Ile  Tyr
                  35                      40                      45

Ala  Asp  Ser  Glu  Arg  Pro  Ser  Gly  Ile  Pro  Ala  Arg  Phe  Ser  Gly  Ser
             50                      55                      60

Asn  Ser  Gly  Thr  Thr  Ala  Thr  Leu  Thr  Ile  Ser  Gly  Val  Glu  Ala  Xaa
        65                       70                      75                           80

Asp  Glu  Ala  Asp  Tyr  Tyr  Cys  Gln  Val  Trp  Asp  Ser  Thr  Ala  Asp  His
                            85                      90                      95

Trp  Val  Phe  Gly  Gly  Gly  Thr  Arg  Leu  Thr  Val  Leu  Gly
                       100                     105
```

( 2 ) INFORMATION FOR SEQ ID NO:93:

( i ) SEQUENCE CHARACTERISTICS:
        ( A ) LENGTH: 130 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Homo sapiens ( v i i i ) POSITION IN GENOME:
        ( A ) CHROMOSOME/SEGMENT: VH3 consensus ( x i ) SEQUENCE DESCRIPTION: SEQ ID NO:93:

```
        Glu  Val  Gln  Leu  Val  Glu  Ser  Gly  Gly  Gly  Leu  Val  Gln  Pro  Gly  Gly
        1               5                       10                      15

Ser  Leu  Arg  Leu  Ser  Cys  Ala  Ala  Ser  Gly  Phe  Thr  Phe  Ser  Asp  Tyr
                       20                      25                      30

Ala  Met  His  Trp  Val  Arg  Gln  Ala  Pro  Gly  Lys  Gly  Leu  Glu  Trp  Val
                  35                      40                      45

Xaa  His  Ile  Glu  Glu  Lys  Xaa  Asn  Gly  Ser  Ala  Thr  Tyr  Tyr  Ala  Asp
             50                      55                      60

Ser  Val  Lys  Gly  Arg  Phe  Thr  Ile  Ser  Arg  Asp  Asp  Ser  Lys  Asn  Thr
        65                       70                      75                           80

Leu  Tyr  Leu  Gln  Met  Asn  Ser  Leu  Arg  Ala  Glu  Asp  Thr  Ala  Val  Tyr
                            85                      90                      95

Tyr  Cys  Ala  Arg  Asp  Pro  Glu  Val  Glu  Ser  Leu  Xaa  Xaa  Xaa  Phe  Xaa
                       100                     105                     110

Tyr  Xaa  Xaa  Phe  Phe  Asp  Ser  Trp  Gly  Gln  Gly  Thr  Leu  Val  Thr  Val
                  115                     120                     125

Ser  Ser
        130
```

( 2 ) INFORMATION FOR SEQ ID NO:94:

( i ) SEQUENCE CHARACTERISTICS:
        ( A ) LENGTH: 123 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i i i ) POSITION IN GENOME:
        ( A ) CHROMOSOME/SEGMENT: RF TS2

( x i ) SEQUENCE DESCRIPTION: SEQ ID NO:94:

```
        Gln  Val  Gln  Leu  Val  Glu  Ser  Gly  Gly  Gly  Val  Val  Gln  Pro  Gly  Arg
```

|  |  |  |  |  |  |  |  |  |  |  |  |  |  |  |
|---|---|---|---|---|---|---|---|---|---|---|---|---|---|---|
| 1 |  |  |  | 5 |  |  |  |  | 10 |  |  |  |  | 15 |

Ser Leu Arg Leu Ser Cys Ala Ala Ser Gly Phe Thr Phe Ser Ser Tyr
        20                  25                  30

Gly Met His Trp Val Arg Gln Ala Pro Gly Lys Gly Leu Glu Trp Val
        35                  40                  45

Xaa Val Ile Ser Tyr Asp Gly Ser Asn Glu Tyr Phe Ala Asp Ser Val
    50              55                  60

Lys Gly Arg Phe Thr Ile Ser Arg Asp Asp Ser Asn Asn Thr Leu Tyr
65                  70              75                      80

Met Gly Met Asn Ser Leu Arg Ala Glu Asp Thr Ala Val Tyr Tyr Cys
            85                  90                  95

Ala Arg Asp Arg Val Ala Val Tyr Ala Ser Val Phe Phe Ile Asp Ser
            100             105                 110

Phe Asp Ile Trp Gly Gln Gly Thr Gly Val Thr
        115             120

( 2 ) INFORMATION FOR SEQ ID NO:95:

( i ) SEQUENCE CHARACTERISTICS:
    ( A ) LENGTH: 126 amino acids
    ( B ) TYPE: amino acid
    ( C ) STRANDEDNESS: Not Relevant
    ( D ) TOPOLOGY: Not Relevant ( i i ) MOLECULE TYPE: peptide ( v i i i ) POSITION IN GENOME:
    ( A ) CHROMOSOME/SEGMENT: RF SJ1

( x i ) SEQUENCE DESCRIPTION: SEQ ID NO:95:

Gln Val Gln Leu Val Glu Ser Gly Gly Gly Val Val Gly Pro Gly Arg
1               5                   10                  15

Ser Leu Arg Leu Ser Cys Ala Ala Ser Gly Phe Ser Phe Ser Ser Tyr
        20                  25                  30

Gly Met His Trp Val Arg Gln Cys Pro Gly Lys Gly Leu Glu Trp Val
        35                  40                  45

Xaa Val Ile Ser Asp Asp Gly Ser Asn Lys Tyr Tyr Ala Asp Ser Val
    50              55                  60

Lys Gly Arg Phe Thr Ile Ser Arg Asp Asp Ser Lys Lys Thr Leu Tyr
65                  70              75                      80

Leu Gln Met Asn Ser Leu Arg Asp Glu Asp Thr Ala Val Tyr Tyr Cys
            85                  90                  95

Ala Lys Gly Val Tyr Cys Ser Ser Ser Ser Cys Tyr Ser Tyr Tyr Tyr
            100             105                 110

Tyr His Tyr Met Asp Val Trp Gly Lys Gly Thr Thr Val Thr
        115             120                 125

( 2 ) INFORMATION FOR SEQ ID NO:96:

( i ) SEQUENCE CHARACTERISTICS:
    ( A ) LENGTH: 128 amino acids
    ( B ) TYPE: amino acid
    ( C ) STRANDEDNESS: Not Relevant
    ( D ) TOPOLOGY: Not Relevant ( i i ) MOLECULE TYPE: peptide ( v i i i ) POSITION IN GENOME:
    ( A ) CHROMOSOME/SEGMENT: RF SJ2

( x i ) SEQUENCE DESCRIPTION: SEQ ID NO:96:

Gln Val Gln Leu Val Glu Ser Gly Gly Gly Val Val Gln Pro Ser Arg

```
          1                    5                              10                            15
     Ser  Leu  Arg  Leu  Ser  Cys  Ala  Ala  Ser  Gly  Phe  Thr  Phe  Ser  Ser  Tyr
                    20                     25                     30

Ala  Met  His  Trp  Val  Arg  Gly  Ala  Pro  Gly  Lys  Gly  Leu  Glu  Trp  Val
               35                          40                     45

Xaa  Val  Ile  Ser  Tyr  Asp  Gly  Ser  Asn  Lys  Tyr  Tyr  Ala  Asp  Ser  Val
               50                     55                          60

Lys  Gly  Arg  Phe  Thr  Ile  Ser  Arg  Asp  Asp  Ser  Lys  Asn  Thr  Leu  Ser
     65                        70                          75                         80

Leu  Gln  Met  Asn  Ser  Leu  Arg  Ala  Glu  Asp  Thr  Ala  Val  Tyr  Tyr  Cys
                         85                     90                          95

Ala  Arg  Gly  Arg  Phe  Cys  Ser  Gly  Gln  Ser  Cys  Tyr  Ser  Tyr  Tyr  Tyr
                    100                    105                         110

Tyr  Tyr  Tyr  Met  Asp  Val  Gly  Lys  Gly  Thr  Thr  Val  Thr  Val  Ser  Ser
                    115                    120                         125
```

( 2 ) INFORMATION FOR SEQ ID NO:97:

( i ) SEQUENCE CHARACTERISTICS:
        ( A ) LENGTH: 117 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i i i ) POSITION IN GENOME:
        ( A ) CHROMOSOME/SEGMENT: BE ( x i ) SEQUENCE DESCRIPTION: SEQ ID NO:97:

```
     Glu  Val  Gln  Leu  Leu  Glu  Ser  Gly  Gly  Gly  Leu  Val  Gln  Pro  Gly  Gly
     1                    5                              10                          15

Ser  Leu  Arg  Leu  Ser  Cys  Ala  Val  Ser  Gly  Phe  Asn  Phe  Ser  Ser  Cys
                    20                     25                          30

Thr  Met  Thr  Trp  Val  Arg  Gln  Ala  Pro  Gly  Lys  Gly  Leu  Glu  Trp  Val
                    35                     40                          45

Xaa  Thr  Ile  Ser  Ala  Ser  Gly  Tyr  Ala  Thr  Tyr  Tyr  Ala  Asp  Ser  Val
               50                     55                               60

Lys  Gly  Arg  Ile  Thr  Ile  Ser  Arg  Asp  Asp  Ser  Lys  Asn  Thr  Leu  Tyr
     65                        70                               75                    80

Leu  Gln  Met  Asn  Ser  Leu  Arg  Ala  Glu  Asp  Ala  Ala  Val  Tyr  Tyr  Cys
                         85                          90                          95

Ala  Asn  Asn  Ile  Ser  Glu  Thr  Leu  Asp  Ser  Trp  Gly  Gln  Gly  Thr  Leu
                    100                    105                         110

Val  Thr  Val  Ser  Ser
                    115
```

( 2 ) INFORMATION FOR SEQ ID NO:98:

( i ) SEQUENCE CHARACTERISTICS:
        ( A ) LENGTH: 120 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i i i ) POSITION IN GENOME:
        ( A ) CHROMOSOME/SEGMENT: CHERRI ( x i ) SEQUENCE DESCRIPTION: SEQ ID NO:98:

```
          Glu  Val  Gln  Leu  Val  Glu  Ser  Gly  Gly  Gly  Leu  Val  Gln  Pro  Gly  Arg
```

```
           1               5                    10                   15

Ser   Leu   Arg   Leu   Ser   Cys   Ala   Ala   Ser   Gly   Phe   Asn   Phe   Gly   Asp   Tyr
                            20                      25                      30

Ser   Met   Thr   Trp   Val   Arg   Gln   Ala   Pro   Gly   Lys   Gly   Leu   Glu   Trp   Val
                      35                            40                            45

Xaa   Ser   Ile   Arg   Ser   Lys   Asp   Tyr   Gly   Gly   Thr   Thr   Glu   Tyr   Ala   Ala
                50                            55                      60

Ser   Val   Lys   Gly   Arg   Phe   Thr   Ile   Ser   Arg   Asp   Asp   Ser   Lys   Ser   Ile
          65                            70                      75                                  80

Leu   Tyr   Leu   Gln   Met   Asn   Ser   Leu   Arg   Ala   Glu   Asp   Thr   Ala   Val   Tyr
                                  85                      90                            95

Tyr   Cys   Ser   Arg   Asn   Asn   Thr   Ser   Pro   Tyr   Phe   Asp   Tyr   Trp   Gly   Glu
                            100                           105                           110

Gly   Thr   Leu   Val   Thr   Val   Ser   Ser
                      115                           120
```

( 2 ) INFORMATION FOR SEQ ID NO:99:

( i ) SEQUENCE CHARACTERISTICS:
    ( A ) LENGTH: 125 amino acids
    ( B ) TYPE: amino acid
    ( C ) STRANDEDNESS: Not Relevant
    ( D ) TOPOLOGY: Not Relevant ( i i ) MOLECULE TYPE: peptide ( v i i i ) POSITION IN GENOME:
    ( A ) CHROMOSOME/SEGMENT: 18/2

( x i ) SEQUENCE DESCRIPTION: SEQ ID NO:99:

```
          Glu   Val   Gln   Leu   Val   Glu   Ser   Gly   Gly   Gly   Leu   Val   Gln   Pro   Gly   Arg
          1                       5                             10                            15

Ser   Leu   Arg   Leu   Ser   Cys   Ala   Ala   Ser   Gly   Phe   Thr   Phe   Ser   Ser   Tyr
                            20                            25                            30

Ala   Met   Ser   Trp   Val   Arg   Gln   Ala   Pro   Gly   Lys   Gly   Leu   Glu   Trp   Val
                      35                            40                            45

Xaa   Ala   Ile   Ser   Gly   Ser   Gly   Gly   Ser   Thr   Tyr   Tyr   Ala   Asp   Ser   Val
                50                            55                      60

Lys   Gly   Arg   Phe   Thr   Ile   Ser   Arg   Asp   Asp   Ser   Lys   Asn   Thr   Leu   Tyr
          65                            70                      75                                  80

Leu   Gln   Met   Asn   Ser   Leu   Arg   Ala   Glu   Asp   Thr   Ala   Val   Tyr   Tyr   Cys
                            85                            90                            95

Ala   Lys   Gly   Gln   Val   Leu   Tyr   Tyr   Gly   Ser   Gly   Ser   Tyr   His   Trp   Phe
                            100                           105                           110

Asp   Pro   Trp   Gly   Gln   Gly   Thr   Leu   Val   Thr   Val   Ser   Ser
                      115                           120                           125
```

( 2 ) INFORMATION FOR SEQ ID NO:100:

( i ) SEQUENCE CHARACTERISTICS:
    ( A ) LENGTH: 119 amino acids
    ( B ) TYPE: amino acid
    ( C ) STRANDEDNESS: Not Relevant
    ( D ) TOPOLOGY: Not Relevant ( i i ) MOLECULE TYPE: peptide ( v i i i ) POSITION IN GENOME:
    ( A ) CHROMOSOME/SEGMENT: K6H6

( x i ) SEQUENCE DESCRIPTION: SEQ ID NO:100:

```
          Glu   Val   Arg   Leu   Val   Glu   Ser   Gly   Gly   Asp   Leu   Val   Glu   Pro   Gly   Gly
```

```
                    1                    5                              10                          15
        Ser    Leu    Arg    Val    Ser    Cys    Glu    Val    Ser    Gly    Phe    Ile    Phe    Ser    Lys    Ala
                             20                                 25                          30

Trp    Met    Asn    Trp    Val    Arg    Gln    Ala    Pro    Gly    Lys    Gly    Leu    Gln    Trp    Val
                      35                                 40                                 45

Xaa    Gln    Ile    Lys    Asn    Lys    Val    Asp    Gly    Gly    Thr    Ile    Asp    Tyr    Ala    Ala
               50                                 55                                 60

Pro    Val    Lys    Gly    Arg    Phe    Ile    Ile    Ser    Arg    Asp    Asp    Ser    Lys    Ser    Thr
        65                                 70                                 75                                 80

Leu    Tyr    Leu    Gln    Met    Asn    Ser    Leu    Lys    Ile    Glu    Asp    Thr    Ala    Val    Tyr
                                    85                                 90                                 95

Tyr    Cys    Val    Gly    Asn    Tyr    Thr    Gly    Thr    Val    Asp    Tyr    Trp    Gly    Gln    Gly
                             100                                105                                110

Thr    Leu    Val    Thr    Val    Ser    Ser
                             115
```

( 2 ) INFORMATION FOR SEQ ID NO:101:

( i ) SEQUENCE CHARACTERISTICS:
        ( A ) LENGTH: 120 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i i i ) POSITION IN GENOME:
        ( A ) CHROMOSOME/SEGMENT: 1B11

( x i ) SEQUENCE DESCRIPTION: SEQ ID NO:101:

```
        Glu    Met    Gln    Leu    Val    Glu    Ser    Gly    Gly    Ala    Phe    Val    Gln    Pro    Gly    Gly
        1                           5                                 10                                 15

Ser    Leu    Lys    Leu    Ser    Cys    Ala    Ala    Ser    Gly    Phe    Asn    Phe    Ser    Asp    Ser
                             20                                 25                                 30

Thr    Ile    His    Trp    Val    Arg    Gln    Ala    Ser    Gly    Lys    Ser    Leu    Glu    Trp    Val
                      35                                 40                                 45

Xaa    His    Ile    Glu    Asn    Lys    Thr    Lys    Asn    Tyr    Ala    Thr    Ile    Tyr    Arg    Ala
               50                                 55                                 60

Ser    Val    Lys    Gly    Arg    Phe    Thr    Ile    Ser    Arg    Asp    Asp    Ser    Lys    Asn    Thr
        65                                 70                                 75                                 80

Ala    Phe    Leu    Gln    Met    Asp    Ser    Leu    Arg    Pro    Asp    Asp    Thr    Ala    Leu    Tyr
                                    85                                 90                                 95

Tyr    Cys    Ala    Pro    Pro    Pro    Glu    Val    Glu    Ser    Leu    Arg    Ser    Trp    Gly    Arg
                             100                                105                                110

Gly    Thr    Leu    Val    Thr    Val    Ser    Ser
                             115                                120
```

( 2 ) INFORMATION FOR SEQ ID NO:102:

( i ) SEQUENCE CHARACTERISTICS:
        ( A ) LENGTH: 128 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: #40

( x i ) SEQUENCE DESCRIPTION: SEQ ID NO:102:

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Asp | Met | Asn | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | 40 | | | | | | 45 | | | |

| Xaa | Tyr | Ile | Ser | Ser | Ala | Ser | Gly | Tyr | Ile | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Phe | Ala | Lys | Asn | Ser | Leu | Ser |
|---|---|---|---|---|---|---|---|---|---|---|---|---|---|---|---|
| 65 | | | | | 70 | | | | | 75 | | | | | 80 |

| Leu | Gln | Met | Ser | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Gln | Pro | Val | Leu | Gln | Phe | Leu | Glu | Trp | Leu | Leu | Pro | Thr |
|---|---|---|---|---|---|---|---|---|---|---|---|---|---|---|---|
| | | | 100 | | | | | 105 | | | | | 110 | | |

| Thr | Gly | Ser | Asp | Val | Trp | Gly | Pro | Gly | Val | Leu | Val | Thr | Val | Ser | Ser |
|---|---|---|---|---|---|---|---|---|---|---|---|---|---|---|---|
| | | 115 | | | | | 120 | | | | | 125 | | | |

( 2 ) INFORMATION FOR SEQ ID NO:103:

( i ) SEQUENCE CHARACTERISTICS:
        ( A ) LENGTH: 116 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: #9

( x i ) SEQUENCE DESCRIPTION: SEQ ID NO:103:

| Glu | Val | Gln | Leu | Val | Glu | Ser | Gly | Gly | Gly | Leu | Ala | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Ser | Leu | Ser | Cys | Val | Ala | Ser | Gly | Phe | Thr | Phe | Ser | Asn | Tyr |
|---|---|---|---|---|---|---|---|---|---|---|---|---|---|---|---|
| | | | 20 | | | | | 25 | | | | | 30 | | |

| Asn | Met | Asp | Trp | Val | Arg | Gln | Ser | Pro | Gly | Lys | Gly | Leu | Glu | Trp | Val |
|---|---|---|---|---|---|---|---|---|---|---|---|---|---|---|---|
| | | 35 | | | | 40 | | | | | | 45 | | | |

| Xaa | Arg | Val | Ile | Arg | Lys | Gly | Ala | Arg | Thr | Lys | Tyr | Ala | Ala | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asp | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Ser | Ser | Leu | Lys | Thr | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Val | Ala | Ala | Ala | Gly | Thr | Gly | Gly | Gln | Gly | Val | Leu | Val |
|---|---|---|---|---|---|---|---|---|---|---|---|---|---|---|---|
| | | | 100 | | | | | 105 | | | | | 110 | | |

| Thr | Val | Ser | Ser |
|---|---|---|---|
| | | 115 | |

( 2 ) INFORMATION FOR SEQ ID NO:104:

( i ) SEQUENCE CHARACTERISTICS:
        ( A ) LENGTH: 123 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i ) ORIGINAL SOURCE:
    ( A ) ORGANISM: Monkey ( v i i i ) POSITION IN GENOME:
    ( A ) CHROMOSOME/SEGMENT: #34

( x i ) SEQUENCE DESCRIPTION: SEQ ID NO:104:

```
Glu Val Gln Leu Glu Glu Ser Gly Gly Gly Leu Val Gln Phe Gly Gly
 1               5                  10                  15
Ser Leu Arg Leu Ser Cys Ala Ala Ser Gly Phe Thr Phe Ser Thr Tyr
            20                  25                  30
Asp Met Thr Trp Val Arg Gln Ala Pro Gly Lys Gly Leu Glu Trp Val
        35                  40                  45
Xaa Arg Ile Ser Trp Asn Ser Gly Thr Ile Tyr Tyr Ala Ser Ser Val
    50                  55                  60
Lys Gly Arg Phe Thr Ile Ser Arg Asp Asp Ser Lys Asn Thr Leu Tyr
65                  70                  75                  80
Leu Gln Met Asn Arg Leu Arg Ala Glu Asp Thr Ala Val Tyr Tyr Cys
                85                  90                  95
Ala Arg Gly Thr Ala Leu Cys Ser Asp Ser Gly Cys Ser Ser Asp Val
            100                 105                 110
Trp Gly Gln Gly Thr Leu Val Thr Val Ser Ser
            115                 120
```

( 2 ) INFORMATION FOR SEQ ID NO:105:

( i ) SEQUENCE CHARACTERISTICS:
    ( A ) LENGTH: 122 amino acids
    ( B ) TYPE: amino acid
    ( C ) STRANDEDNESS: Not Relevant
    ( D ) TOPOLOGY: Not Relevant ( i i ) MOLECULE TYPE: peptide ( v i ) ORIGINAL SOURCE:
    ( A ) ORGANISM: Monkey ( v i i i ) POSITION IN GENOME:
    ( A ) CHROMOSOME/SEGMENT: #36

( x i ) SEQUENCE DESCRIPTION: SEQ ID NO:105:

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Ser Phe Ser Glu Tyr
            20                  25                  30
Ser Ile His Trp Val Arg Gln Ala Gln Gly Lys Gly Leu Arg Trp Val
        35                  40                  45
Xaa Leu Ala Gly Lys Lys Ala Asp Arg Tyr Lys Thr Glu Tyr Ala Thr
    50                  55                  60
Ala Val Lys Gly Arg Phe Thr Ile Ser Arg Asp Asp Ser Lys Ser Thr
65                  70                  75                  80
Leu Tyr Leu Gln Met Asn Thr Leu Arg Ala Glu Asp Thr Ala Val Tyr
                85                  90                  95
Tyr Cys Ala Arg Pro Val Leu Gly Asp Arg Trp Phe Phe Asp Leu Trp
            100                 105                 110
Gly Gln Gly Thr Pro Ile Thr Ile Ser Ser
            115                 120
```

( 2 ) INFORMATION FOR SEQ ID NO:106:

( i ) SEQUENCE CHARACTERISTICS:
    ( A ) LENGTH: 130 amino acids ( B ) TYPE: amino acid
( C ) STRANDEDNESS: Not Relevant
( D ) TOPOLOGY: Not Relevant ( i i ) MOLECULE TYPE: peptide ( v i ) ORIGINAL SOURCE:
    ( A ) ORGANISM: Homo sapiens ( v i i i ) POSITION IN GENOME:
    ( A ) CHROMOSOME/SEGMENT: VH2

( x i ) SEQUENCE DESCRIPTION: SEQ ID NO:106:

```
Xaa Val Thr Leu Arg Glu Ser Gly Pro Xaa Leu Val Lys Pro Thr Glu
 1           5                   10                  15

Thr Leu Thr Leu Thr Cys Thr Val Ser Gly Phe Ser Leu Ser Thr Xaa
            20                  25                  30

Gly Met Xaa Val Gly Trp Ile Arg Gln Pro Pro Gly Lys Xaa Leu Glu
        35                  40                  45

Trp Leu Xaa Arg Ile Asn Xaa Trp Asp Asp Asp Lys Tyr Tyr Ser Thr
        50              55                  60

Ser Leu Arg Ser Arg Leu Thr Ile Ser Lys Asp Thr Ser Lys Asn Gln
65                      70                  75                  80

Val Val Leu Xaa Xaa Xaa Xaa Xaa Asp Pro Xaa Asp Thr Ala Thr Tyr
                85                  90                  95

Tyr Cys Ala Arg Arg Xaa Pro Arg Xaa Xaa Xaa Gly Asp Xaa Gly Xaa
            100                 105                 110

Tyr Xaa Xaa Ala Phe Asp Val Trp Gly Gln Gly Thr Thr Val Thr Val
    115                 120                 125

Ser Ser
130
```

( 2 ) INFORMATION FOR SEQ ID NO:107:

( i ) SEQUENCE CHARACTERISTICS:
        ( A ) LENGTH: 420 base pairs
        ( B ) TYPE: nucleic acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: Anti-CD4 VH ( i x ) FEATURE:
        ( A ) NAME/KEY: CDS
        ( B ) LOCATION: 4..420

( i x ) FEATURE:
        ( A ) NAME/KEY: mat_peptide
        ( B ) LOCATION: 61..420

( x i ) SEQUENCE DESCRIPTION: SEQ ID NO:107:

```
GAC ATG AAA CAC CTG TGG TTC TTC CTC CTC CTG GTG GCA GCC CCC AGA      48
    Met Lys His Leu Trp Phe Phe Leu Leu Leu Val Ala Ala Pro Arg
    -19              -15                 -10                 - 5

TGG GTC TTG TCC CAG GTG CAG CTG CAG GAG GCG GGC CCA GGA CTG GTG      96
Trp Val Leu Ser Gln Val Gln Leu Gln Glu Ala Gly Pro Gly Leu Val
                1               5                   10

AAG CCT TCG GAG ACC CTG TCC CTC ACC TGC AGT GTC TCT GGT GGC TCC     144
Lys Pro Ser Glu Thr Leu Ser Leu Thr Cys Ser Val Ser Gly Gly Ser
            15                  20                  25
```

|  |  |  |  |  |  |  |  |  |  |  |  |  |  |  |  | |
|---|---|---|---|---|---|---|---|---|---|---|---|---|---|---|---|---|
| ATC | AGC | GGT | GAC | TAT | TAT | TGG | TTC | TGG | ATC | CGC | CAG | TCC | CCA | GGG | AAG | 192 |
| Ile | Ser | Gly | Asp | Tyr | Tyr | Trp | Phe | Trp | Ile | Arg | Gln | Ser | Pro | Gly | Lys | |
|  | | 30 | | | | 35 | | | | | 40 | | | | | |
| GGA | CTG | GAG | TGG | ATC | GGC | TAC | ATC | TAT | GGC | AGT | GGT | GGG | GGC | ACC | AAT | 240 |
| Gly | Leu | Glu | Trp | Ile | Gly | Tyr | Ile | Tyr | Gly | Ser | Gly | Gly | Gly | Thr | Asn | |
| 45 | | | | | 50 | | | | | 55 | | | | | 60 | |
| TAC | AAT | CCC | TCC | CTC | AAC | AAT | CGA | GTC | TCC | ATT | TCA | ATA | GAC | ACG | TCC | 288 |
| Tyr | Asn | Pro | Ser | Leu | Asn | Asn | Arg | Val | Ser | Ile | Ser | Ile | Asp | Thr | Ser | |
|  | | | | 65 | | | | | 70 | | | | | 75 | | |
| AAG | AAC | CTC | TTC | TCC | CTG | AAA | CTG | AGG | TCT | GTG | ACC | GCC | GCG | GAC | ACG | 336 |
| Lys | Asn | Leu | Phe | Ser | Leu | Lys | Leu | Arg | Ser | Val | Thr | Ala | Ala | Asp | Thr | |
|  | | | 80 | | | | | 85 | | | | | 90 | | | |
| GCC | GTC | TAT | TAC | TGT | GCG | AGT | AAT | ATA | TTG | AAA | TAT | CTT | CAC | TGG | TTA | 384 |
| Ala | Val | Tyr | Tyr | Cys | Ala | Ser | Asn | Ile | Leu | Lys | Tyr | Leu | His | Trp | Leu | |
|  | | 95 | | | | | 100 | | | | | 105 | | | | |
| TTA | TAC | TGG | GGC | CAG | GGA | GTC | CTG | GTC | ACC | GTC | TCC | | | | | 420 |
| Leu | Tyr | Trp | Gly | Gln | Gly | Val | Leu | Val | Thr | Val | Ser | | | | | |
|  | 110 | | | | 115 | | | | | 120 | | | | | | |

( 2 ) INFORMATION FOR SEQ ID NO:108:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: protein ( x i ) SEQUENCE DESCRIPTION: SEQ ID NO:108:

| Met | Lys | His | Leu | Trp | Phe | Phe | Leu | Leu | Leu | Val | Ala | Ala | Pro | Arg | Trp |
|---|---|---|---|---|---|---|---|---|---|---|---|---|---|---|---|
| -19 | | | | -15 | | | | | -10 | | | | | -5 | |
| Val | Leu | Ser | Gln | Val | Gln | Leu | Gln | Glu | Ala | Gly | Pro | Gly | Leu | Val | Lys |
| | | | 1 | | | 5 | | | | | | 10 | | | |
| Pro | Ser | Glu | Thr | Leu | Ser | Leu | Thr | Cys | Ser | Val | Ser | Gly | Gly | Ser | Ile |
| | 15 | | | | | 20 | | | | | 25 | | | | |
| Ser | Gly | Asp | Tyr | Tyr | Trp | Phe | Trp | Ile | Arg | Gln | Ser | Pro | Gly | Lys | Gly |
| 30 | | | | | 35 | | | | | 40 | | | | | 45 |
| Leu | Glu | Trp | Ile | Gly | Tyr | Ile | Tyr | Gly | Ser | Gly | Gly | Gly | Thr | Asn | Tyr |
| | | | | 50 | | | | | 55 | | | | | 60 | |
| Asn | Pro | Ser | Leu | Asn | Asn | Arg | Val | Ser | Ile | Ser | Ile | Asp | Thr | Ser | Lys |
| | | | 65 | | | | | 70 | | | | | 75 | | |
| Asn | Leu | Phe | Ser | Leu | Lys | Leu | Arg | Ser | Val | Thr | Ala | Ala | Asp | Thr | Ala |
| | | | 80 | | | | | 85 | | | | | 90 | | |
| Val | Tyr | Tyr | Cys | Ala | Ser | Asn | Ile | Leu | Lys | Tyr | Leu | His | Trp | Leu | Leu |
| | 95 | | | | | 100 | | | | | 105 | | | | |
| Tyr | Trp | Gly | Gln | Gly | Val | Leu | Val | Thr | Val | Ser | | | | | |
| 110 | | | | | 115 | | | | | 120 | | | | | |

( 2 ) INFORMATION FOR SEQ ID NO:109:

( i ) SEQUENCE CHARACTERISTICS:
        ( A ) LENGTH: 387 base pairs
        ( B ) TYPE: nucleic acid
        ( C ) STRANDEDNESS: Not Relevant
        ( D ) TOPOLOGY: Not Relevant ( i i ) MOLECULE TYPE: peptide ( v i ) ORIGINAL SOURCE:
        ( A ) ORGANISM: Monkey ( v i i i ) POSITION IN GENOME:
        ( A ) CHROMOSOME/SEGMENT: Anti-CD4 Vlambda ( i x ) FEATURE:
(A) NAME/KEY: CDS
(B) LOCATION: 4..387

( i x ) FEATURE:
(A) NAME/KEY: mat_peptide
(B) LOCATION: 61..387

( x i ) SEQUENCE DESCRIPTION: SEQ ID NO:109:

| ACC | ATG | GCC | TGG | GCT | CTG | CTG | CTC | CTC | GGC | CTC | CTT | GCT | CAC | TTT | ACA | 48 |
| | Met | Ala | Trp | Ala | Leu | Leu | Leu | Leu | Gly | Leu | Leu | Ala | His | Phe | Thr | |
| | -19 | | | | -15 | | | | | -10 | | | | | -5 | |

| GAC | TCT | GCG | GCC | TCC | TAT | GAG | TTG | AGT | CAG | CCT | CGC | TCA | GTG | TCC | GTG | 96 |
| Asp | Ser | Ala | Ala | Ser | Tyr | Glu | Leu | Ser | Gln | Pro | Arg | Ser | Val | Ser | Val | |
| | | | | | 1 | | | | 5 | | | | | 10 | | |

| TCC | CCA | GGA | CAG | ACG | GCC | GGG | TTC | ACC | TGT | GGG | GGA | GAC | AAC | GTT | GGA | 144 |
| Ser | Pro | Gly | Gln | Thr | Ala | Gly | Phe | Thr | Cys | Gly | Gly | Asp | Asn | Val | Gly | |
| | | 15 | | | | | 20 | | | | | 25 | | | | |

| AGG | AAA | AGT | GTA | CAG | TGG | TAC | CAG | CAG | AAG | CCA | CCG | CAG | GCC | CCT | GTG | 192 |
| Arg | Lys | Ser | Val | Gln | Trp | Tyr | Gln | Gln | Lys | Pro | Pro | Gln | Ala | Pro | Val | |
| | 30 | | | | | 35 | | | | | | 40 | | | | |

| CTG | GTC | ATC | TAT | GCT | GAC | AGC | GAA | CGG | CCC | TCA | GGG | ATC | CCT | GCG | CGA | 240 |
| Leu | Val | Ile | Tyr | Ala | Asp | Ser | Glu | Arg | Pro | Ser | Gly | Ile | Pro | Ala | Arg | |
| 45 | | | | | 50 | | | | | 55 | | | | | 60 | |

| TTC | TCT | GGC | TCC | AAC | TCA | GGG | AAC | ACC | GCC | ACC | CTG | ACC | ATC | AGC | GGG | 288 |
| Phe | Ser | Gly | Ser | Asn | Ser | Gly | Asn | Thr | Ala | Thr | Leu | Thr | Ile | Ser | Gly | |
| | | | | 65 | | | | | 70 | | | | | 75 | | |

| GTC | GAG | GCC | GGG | GAT | GAG | GCT | GAC | TAT | TAC | TGT | CAG | GTG | TGG | GAC | AGT | 336 |
| Val | Glu | Ala | Gly | Asp | Glu | Ala | Asp | Tyr | Tyr | Cys | Gln | Val | Trp | Asp | Ser | |
| | | | 80 | | | | | 85 | | | | | 90 | | | |

| ACT | GCT | GAT | CAT | TGG | GTC | TTC | GGC | GGA | GGG | ACC | CGG | CTG | ACC | GTC | CTA | 384 |
| Thr | Ala | Asp | His | Trp | Val | Phe | Gly | Gly | Gly | Thr | Arg | Leu | Thr | Val | Leu | |
| | | 95 | | | | | 100 | | | | | 105 | | | | |

| GGT | | | | | | | | | | | | | | | | 387 |
| Gly | | | | | | | | | | | | | | | | |

( 2 ) INFORMATION FOR SEQ ID NO:110:

( i ) SEQUENCE CHARACTERISTICS:
(A) LENGTH: 128 amino acids
(B) TYPE: amino acid
(D) TOPOLOGY: linear ( i i ) MOLECULE TYPE: protein ( x i ) SEQUENCE DESCRIPTION: SEQ ID NO:110:

| Met | Ala | Trp | Ala | Leu | Leu | Leu | Leu | Gly | Leu | Leu | Ala | His | Phe | Thr | Asp |
| -19 | | | | -15 | | | | | -10 | | | | | -5 | |

| Ser | Ala | Ala | Ser | Tyr | Glu | Leu | Ser | Gln | Pro | Arg | Ser | Val | Ser | Val | Ser |
| | | | 1 | | | | 5 | | | | | 10 | | | |

| Pro | Gly | Gln | Thr | Ala | Gly | Phe | Thr | Cys | Gly | Gly | Asp | Asn | Val | Gly | Arg |
| | 15 | | | | | 20 | | | | | 25 | | | | |

| Lys | Ser | Val | Gln | Trp | Tyr | Gln | Gln | Lys | Pro | Pro | Gln | Ala | Pro | Val | Leu |
| 30 | | | | | 35 | | | | | 40 | | | | | 45 |

| Val | Ile | Tyr | Ala | Asp | Ser | Glu | Arg | Pro | Ser | Gly | Ile | Pro | Ala | Arg | Phe |
| | | | | 50 | | | | | 55 | | | | | 60 | |

| Ser | Gly | Ser | Asn | Ser | Gly | Asn | Thr | Ala | Thr | Leu | Thr | Ile | Ser | Gly | Val |
| | | | | 65 | | | | | 70 | | | | | 75 | |

| Glu | Ala | Gly | Asp | Glu | Ala | Asp | Tyr | Tyr | Cys | Gln | Val | Trp | Asp | Ser | Thr |
| | | 80 | | | | | 85 | | | | | 90 | | | |

| Ala | Asp | His | Trp | Val | Phe | Gly | Gly | Gly | Thr | Arg | Leu | Thr | Val | Leu | Gly |
| | | 95 | | | | | 100 | | | | | 105 | | | |

(2) INFORMATION FOR SEQ ID NO:111:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (viii) POSITION IN GENOME:
(A) CHROMOSOME/SEGMENT: IgG heavy chain variable region primer (xi) SEQUENCE DESCRIPTION: SEQ ID NO:111:

CAGAGCTGGG TACGTCCTCA  20

(2) INFORMATION FOR SEQ ID NO:112:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (viii) POSITION IN GENOME:
(A) CHROMOSOME/SEGMENT: IgG heavy chain variable region primer (xi) SEQUENCE DESCRIPTION: SEQ ID NO:112:

GCCCCCAGAG GTGCTCTTGG  20

(2) INFORMATION FOR SEQ ID NO:113:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (viii) POSITION IN GENOME:
(A) CHROMOSOME/SEGMENT: Ig lambda light chain variable region (xi) SEQUENCE DESCRIPTION: SEQ ID NO:113:

CAGAGCTGGG TACGTGAACC  20

(2) INFORMATION FOR SEQ ID NO:114:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (viii) POSITION IN GENOME:
(A) CHROMOSOME/SEGMENT: Ig lambda light chain variable region (xi) SEQUENCE DESCRIPTION: SEQ ID NO:114:

GGCTTGAAGC TCCTCAGAGG  20